United States Patent [19]
Devlin et al.

[11] Patent Number: 5,846,703
[45] Date of Patent: Dec. 8, 1998

[54] FLUORESCENCE IMMUNOASSAYS USING FLUORESCENT DYES FREE OF AGGREGATION AND SERUM BINDING

[75] Inventors: Robert F. Devlin, San Diego; Walter B. Dandliker, La Jolla; Peter O. G. Arrhenius, San Diego, all of Calif.

[73] Assignee: Diatron Corporation, San Diego, Calif.

[21] Appl. No.: 35,633

[22] Filed: Mar. 23, 1993

Related U.S. Application Data

[63] Continuation-in-part of Ser. No. 856,176, Mar. 23, 1992, abandoned, which is a continuation-in-part of Ser. No. 701,449, May 15, 1991, Pat. No. 5,403,928, which is a continuation-in-part of Ser. No. 523,601, May 15, 1990, abandoned, said Ser. No. 856,176, is a continuation-in-part of Ser. No. 701,465, May 15, 1991, abandoned, which is a continuation-in-part of Ser. No. 524,212, May 15, 1990, abandoned.

[30] Foreign Application Priority Data

Mar. 23, 1993 [WO] WIPO ............. PCT/US93/02470

[51] Int. Cl.[6] .................................................. G01N 33/533
[52] U.S. Cl. ................ 435/5; 435/7.1; 436/518; 436/536; 436/537; 436/66; 436/172; 436/546; 436/800; 436/815; 436/816; 436/817
[58] Field of Search ............. 435/5, 7.92, 7.94, 435/960, 7.1; 436/546, 800, 815, 816, 817, 518, 536, 537, 66, 172

[56] References Cited

U.S. PATENT DOCUMENTS

| | | | |
|---|---|---|---|
| 4,822,877 | 4/1989 | Inada et al. | 540/145 |
| 5,403,928 | 4/1995 | Arrhenuis | 540/128 |

FOREIGN PATENT DOCUMENTS

88/04777  6/1988  WIPO .

OTHER PUBLICATIONS

Barrett et al., "Phthalocyanine and Related Compounds. Part XV. Tetrabentriazaporphin: its preparation from Phthalonitrile and a Proof of its Structure", pp. 1809–1820 in *Phthalocyanine and Related Compounds. Part XV.* (1939).

Hemmila Clin. Chem. 31/3, pp. 359–370 (1985) "Fluoroimmunoassays and Immunofluorometric Assays".

Dandliker et al., Cancer Research, vol. 38, pp. 4212–4224 (1978) "Investigation of Hormone–Receptor Interactions by Means of Fluorescence Labeling".

*Primary Examiner*—Lora M. Green
*Attorney, Agent, or Firm*—Lyon & Lyon

[57] ABSTRACT

Fluorescence immunoassays methods are provided which use fluorescent dyes which are free of aggregation and serum binding. Such immunoassay methods are thus, particularly useful for the assay of biological fluids, such as serum, plasma, whole blood and urine.

72 Claims, 32 Drawing Sheets

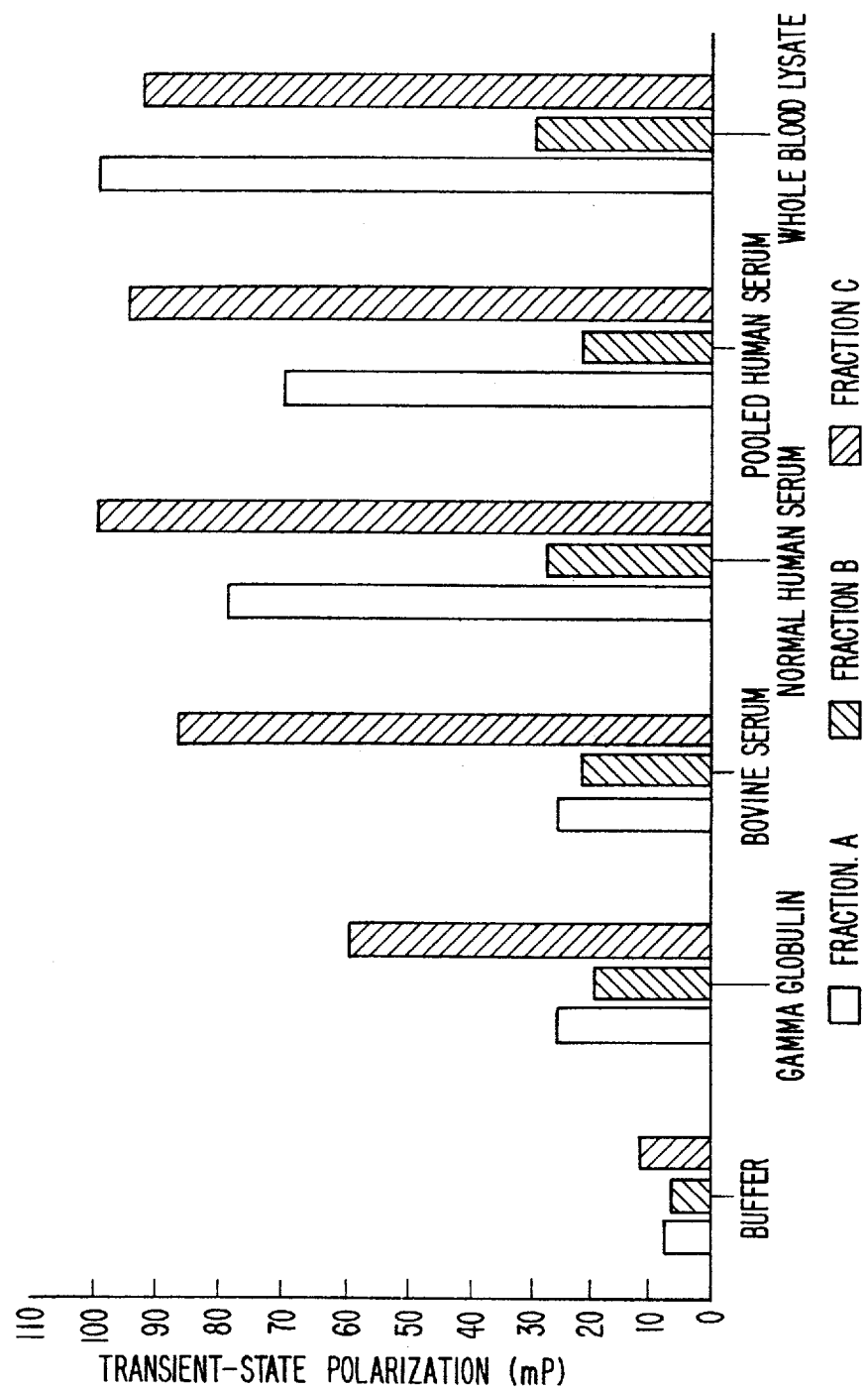

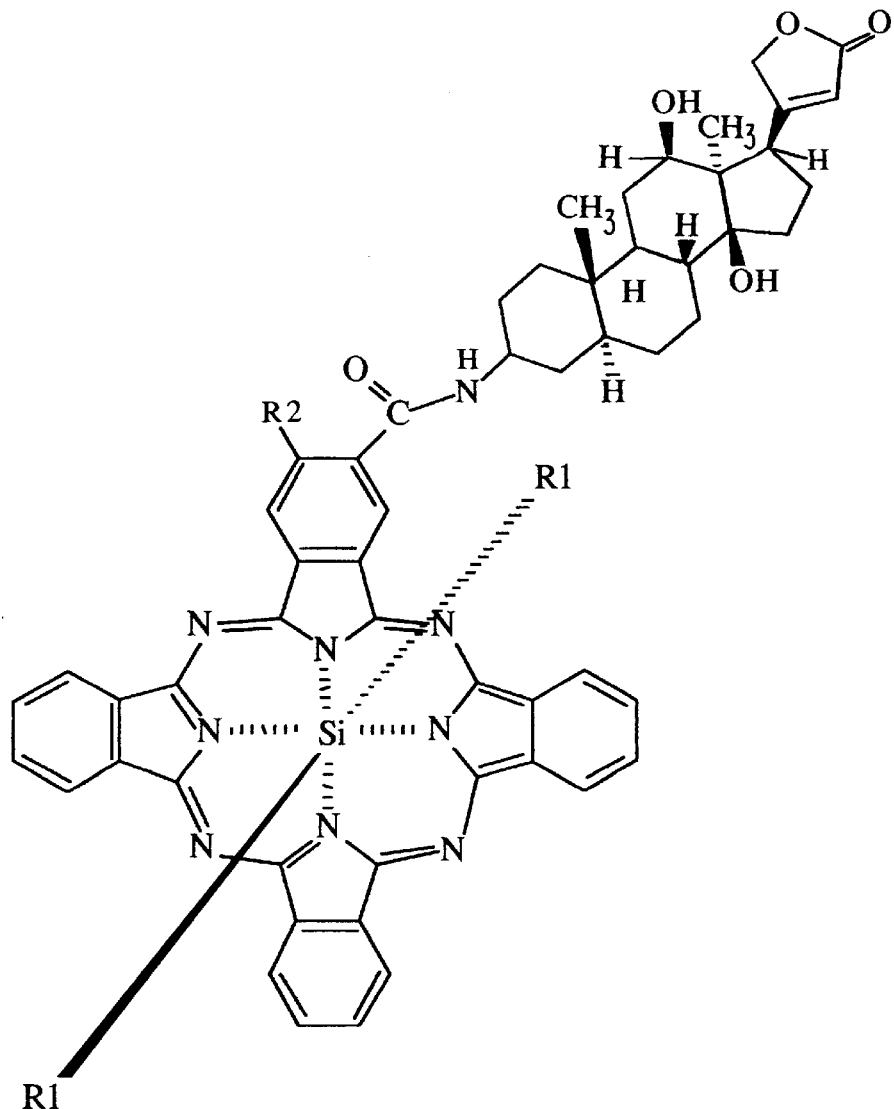
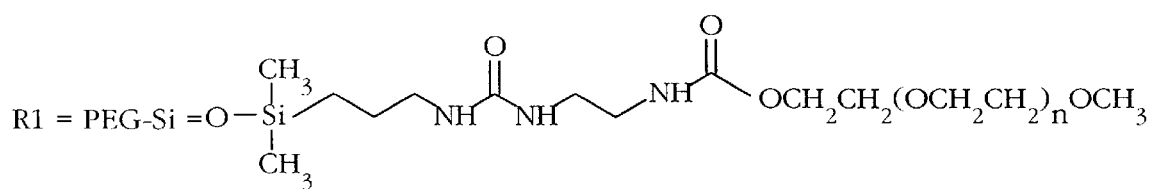
R2 - COOH
FIG. 10.

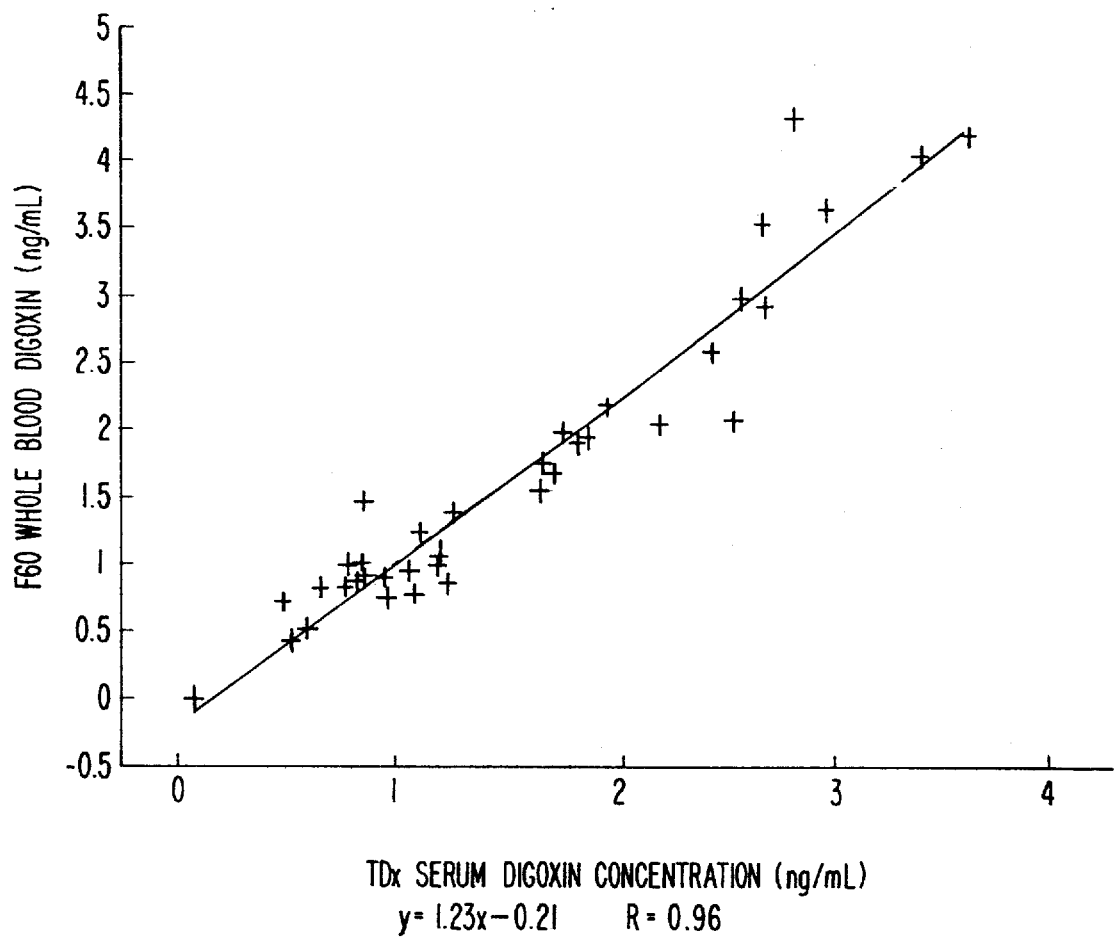

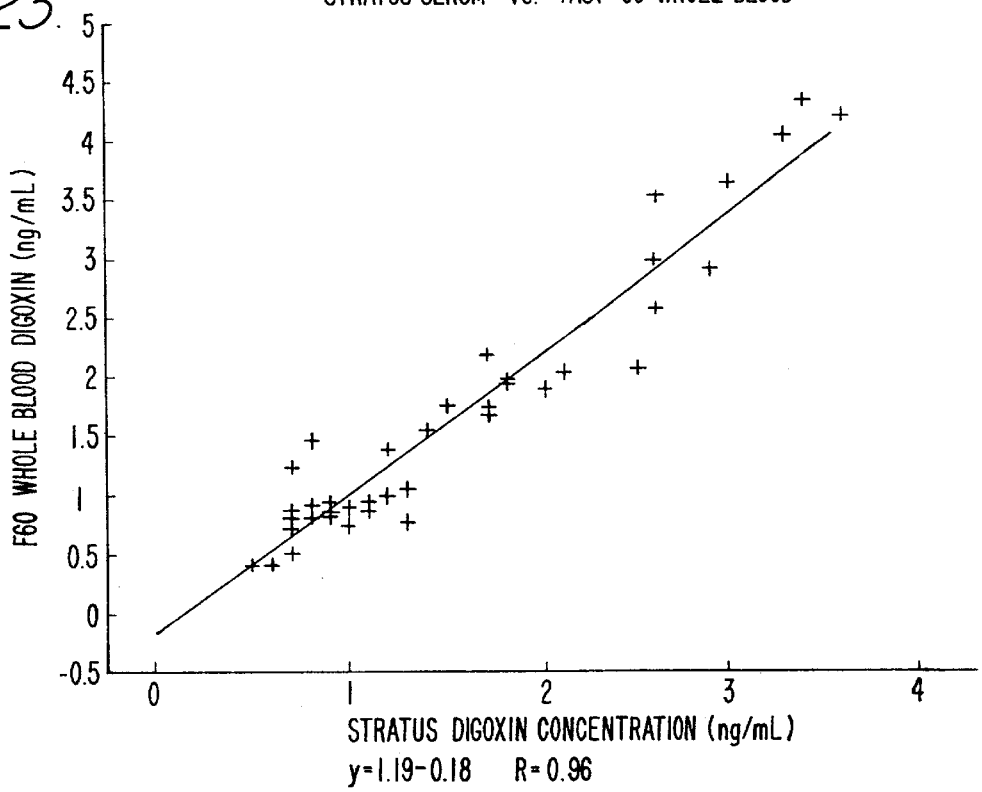
FIG. 23. STRATUS SERUM VS. FAST-60 WHOLE BLOOD
y=1.19−0.18  R=0.96
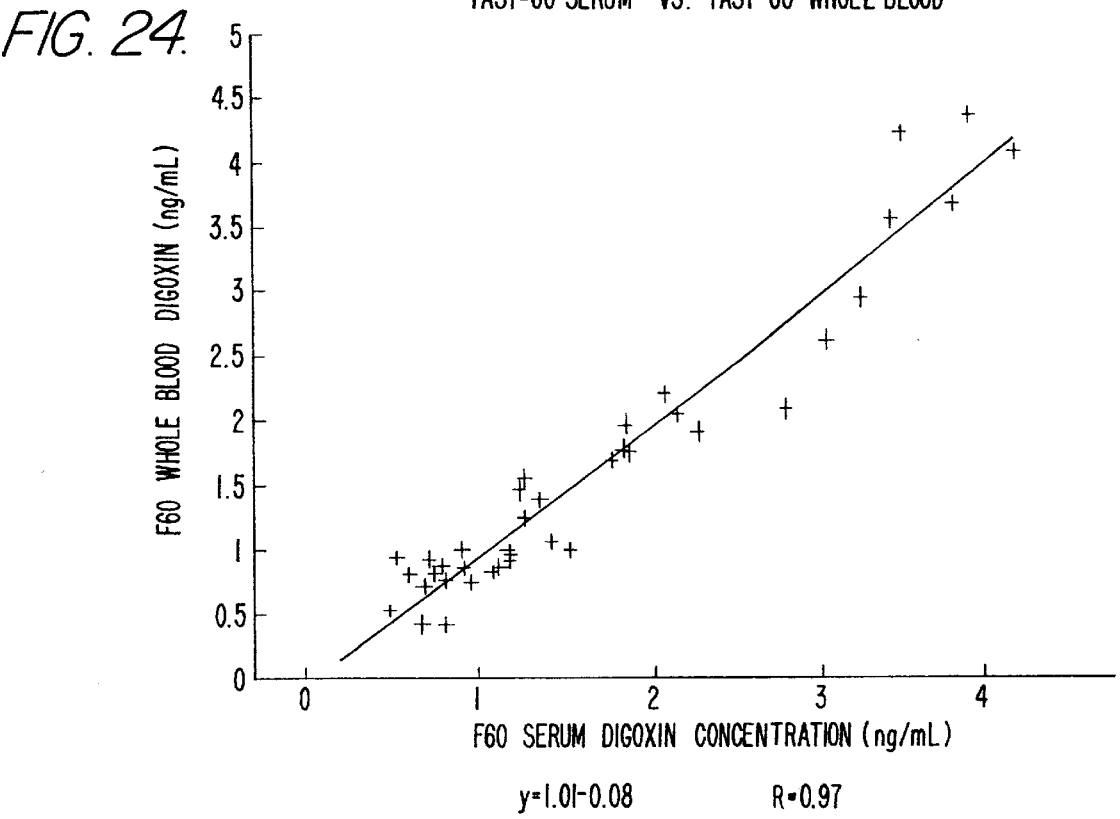
FIG. 24. FAST-60 SERUM VS. FAST-60 WHOLE BLOOD
y=1.01−0.08  R=0.97

R1 = PEG-Si

R2 = COOH

R1 = PEG-Si

R2 = COOH

R1 = PEG-Si

R2 = COOH

R1 = PEG-Si
R2 = COOH

R1 = PEG-Si

R2 = COOH

R1 = PEG-Si
R2 = COOH

R1 = PEG-Si

R2 = COOH

FLUORESCENCE IMMUNOASSAYS USING FLUORESCENT DYES FREE OF AGGREGATION AND SERUM BINDING

This application is a continuation-in-part of U.S. application Ser. No. 07/856,176, filed Mar. 23, 1992 now abandoned, which is a continuation-in-part of U.S. application Ser. No. 701,449, filed May 15, 1991 now U.S. Pat. No. 5,403,928, which is a continuation-in-part of U.S. application Ser. No. 523,601, filed May 15, 1990 now abandoned. U.S. application Ser. No. 07/856,176, filed Mar. 23, 1992 now abandoned, is also a continuation-in-part of U.S. application Ser. No. 701,465, filed May 15, 1991 now abandoned, which is a continuation-in-part of U.S. application Ser. No. 524,212, filed May 15, 1990 now abandoned.

FIELD OF THE INVENTION

The present invention relates to methods for determining the presence or amount of antigenic substances in samples. The invention is directed to fluorescence immunoassays using particular fluorescence dyes which are essentially free of aggregation and serum binding and, thus, are particularly suited for the measurement of antigenic substances in biological materials such as serum, plasma and whole blood.

BACKGROUND OF THE INVENTION

Publications and other reference materials referred to herein are incorporated herein by this reference.

The determination of the presence or amount of antigenic substances is commonly performed by immunoassay.

Immunoassay techniques are based on the binding of the antigenic substance being assayed (the "target analyte") and a receptor for the target analyte. Either the target analyte or the receptor may be labeled to permit detection. Various labels have been employed for use in immunoassays, including radioisotopes, enzymes and fluorescent compounds. Many different types of immunoassays are known in the art, including competitive inhibition assays, sequential addition assays, direct "sandwich" assays, radioallergosorbent assays, radioimmunosorbent assays and enzyme-linked immunosorbent assays.

The basic reaction underlying most immunoassays is the binding of certain substance, termed the "ligand" or "analyte", by a characteristic protein (receptor) to form a macromolecular complex. These binding processes are reversible reactions, and the extent of complex formation for particular analyte and receptor concentrations is regulated by an equilibrium constant according to the law of mass action. Thus, at equilibrium, some of the analyte always exists unbound (free).

In a competitive inhibition immunoassay, the unknown quantity of target analyte in the sample competes with a known amount of labeled target analyte for a limited number of receptor binding sites. The reagents usually consist of a labeled target analyte, such as an antigen, and a solid phase coupled receptor, such as an antibody. The antigen to be assayed competes with the labeled antigen for binding sites on the coupled antibodies. The concentration of target analyte present in the sample can be determined by measuring the amount of labeled target analyte—either "free" or "bound." This is an indirect assay method where the amount of labeled antigen bound to the antibodies is inversely correlated with the amount of antigen in the test solution. Thus, low concentrations of target analyte in the sample will result in low concentrations of "free" labeled target analyte and high concentrations of "bound" labeled target analyte, and vice versa. The amount of "free" or "bound" labeled target analyte is measured using a suitable detector. Quantitative determinations are made by comparing the measure of labeled target analyte with that obtained for calibrated samples containing known quantities of the target analyte. This method has been applied to the assay of a great number of different polypeptide hormones, enzymes and immunoglobulins. This method may also be used as a total liquid system.

It is apparent to those skilled in the art that it is not absolutely necessary that the labeled analyte be identical to the unlabeled target analyte. If there is a difference between the two, for example, if the labeled analyte is an analog of the target analyte, the reaction between labeled and unlabeled analytes may be considered to be competitive for the receptor binding sites; and the reaction will still provide quantitative answers, providing the difference in affinity of the analytes is not too great. Whether or not true competition occurs in a system consisting of labeled analyte, unlabeled analyte, and receptor depends on the nature of the labeled analyte and the specificity of the receptor.

In sequential addition assays, the reagents used are the same as in the competitive inhibition assay described above. However, instead of incubating them at the same time, the unlabeled antigen is first incubated with the antibody, then the labeled antigen is added.

Direct immunoassay systems are also known in the art. Such assays, also termed "immunometric" assays, employ a labeled receptor (antibody) rather than a labeled analyte (antigen). In these assays the amount of labeled receptor associated with the complex is proportioned to the amount of analyte in the sample. Immunometric assays are well-suited to the detection of antigenic substances which are able to complex with two or more antibodies at the same time. In such "two-site" or "sandwich" assays, the antigenic substance has two antibodies bound to its surface at different locations. In a typical "forward" sandwich assay, an antibody bound to a solid phase is first contacted with the sample being tested to form a solid phase antibody:antigen complex. After incubation, the solid support is washed to remove the residual sample, including unreacted antigen, if any. The complex is then reacted with a solution containing a known amount of labeled antibody. After a second incubation to permit the labeled antibody to complex with the antigen bound to the solid support through the unlabeled antibody, the solid support is washed to remove unreacted labeled antibody. The assay can be used as a simple "yes/no" assay to determine whether the antigen is present. Quantitative determinations can be made by comparing the measure of labeled antibody with that of calibrated samples containing known quantities of antigen. "Simultaneous" and "reverse" sandwich assays are also known in the art. A simultaneous assay involves a single incubation step, both the labeled and unlabeled antibodies being added at the same time. A reverse assay involves the addition of labeled antibody followed by addition of unlabeled antibody bound to a suitable solid support. The sandwich technique can also be used to assay antibodies rather than antigens. Such an assay uses as a first receptor an antigen coupled to a solid phase. The antibodies being tested are first bound to the solid phase-coupled antigen. The solid phase is then washed, and then labeled anti-antibody (second receptor) is added.

The radioallergosorbent technique (RAST) is a method for the determination of antigen-specific IgE. The method uses a solid phase coupled antigen and an immunoabsorbent purified antibody labeled with a radioactive isotope. The method is used to detect reaginic antibodies against various antigens which elicit allergic reactions (allergens). The reaginic antibodies react with allergen bound to a solid matrix. After washing of the solid phase, the allergen-bound reaginic antibodies are detected by their ability to bind labeled antibodies against IgE. A variant of RAST can be used for the determination of allergens. The allergen to be tested is incubated with the reaginic antibody. The mixture is then tested with RAST using the same allergen coupled to the solid matrix. The allergen in solution reacts with the reaginic antibodies and thus inhibits the binding of these antibodies to the solid phase-coupled allergen.

Another assay method for the determination of IgE is the radioimmunosorbent technique ("RIST"). In this method, the solid support is sensitized with anti-IgE and increasing amounts of labeled IgE are added to determine the maximum amount of IgE that can bind. A quantity of labeled IgE equivalent to approximately 80% of the plateau binding is chosen. In the test experiments, this amount of labeled IgE is mixed with the serum containing the IgE to be tested. The test IgE competes with the labeled IgE. The more IgE present in the test serum the less the amount of labeled IgE that binds. Thus, by producing a standard curve the amount of IgE in a sample can be determined.

The above immunoassay methods can be applied to the assay of many different biologically active substances. Among such substances are haptens, hormones, gamma globulin, allergens, viruses, virus subunits, bacteria, toxins such as those associated with tetanus and animal venom, and many drugs. Similar techniques can be used in non-immunological systems with, for example, specific binding proteins.

Although some of the immunoassay methods described above utilize radioactive labels, those skilled in the art will appreciate that the assays can be adapted to use an alternate label, for example, a fluorophore.

If the properties of the label are not altered by binding, for example, as in a radioimmunoassay, a separation step is required to separate "free" from "bound" labeled target analyte. Such assays, which require a separation step, are called "heterogeneous" assays. If the properties of the label are altered in some way when it is bound, no separation step is required, and the immunoassay is termed "homogeneous."

The measurement of target analytes in biological fluids, such as serum, plasma and whole blood, requires immunoassay methods which are both specific and sensitive. Both the specificity and sensitivity of an immunoassay depend on the characteristics of the binding interaction between the target analyte and the receptor involved. For example, the reaction must be specific for the analyte to be measured and the receptor used should not bind to any other structurally related compounds. In addition, by choosing a receptor with a high affinity for the target analyte, the sensitivity can be increased.

The label used to monitor the assay affects the sensitivity of an immunoassay. Labels currently used for immunoassay of target analytes in biological fluids include radioisotopes (radioimmunoassay, RIA), enzymes (enzyme immunoassay, EIA), fluorescent labels (fluorescence immunoassay, FIA), and chemiluminescent labels (chemiluminescent immunoassay, CIA).

RIAs are sufficiently sensitive for use in detection in low concentrations of analytes because of their low background. They are disadvantageous in that they are heterogeneous, thus requiring a separation step before measurement of the bound and/or free portions of labelled target analyte. RIAs involve the inconvenience and hazards associated with the handling and disposing of radioisotopes. In addition, they are labor intensive and have a short shelf life due to the half-lives of radiolabels and to chemical damage produced by the emitted radiation.

EIAs have the advantage of increased signal over background, longer shelf life, lack of radiation hazards, and homogeneity. They are disadvantageous in that, because they involve enzyme kinetic reactions, they are affected by the time of the kinetic measurements, as well as by variations in temperature, pH and ionic strength. The temperature of the enzyme incubation is particularly critical, and variations of more than 0.5° C. can significantly affect assay results. Thus, drifts in standard curve may result from temperature fluctuation and inconsistencies in sample handling. Enzyme activity may also be affected by constituents in biological samples, such as plasma constituents. See generally Strong, J. E. and Altman, R. E., "Enzyme Immunoassay: Application to Therapeutic Drug Measurement," in P. Moyer et al., *Applied Therapeutic Drug Monitoring*, American Association of Clinical Chemistry (1984).

Chemiluminescent immunoassays (CIAs) offer a fairly high degree of sensitivity (picomole per liter range) but lack specificity in some instances. CIAs are disadvantageous because they are heterogeneous, require expensive reagents, and are expensive to automate. See generally Boeckx, R. L., "Luminescence: A New Analytical Tool for Therapeutic Drug Monitoring," in P. Moyer et al., *Applied Therapeutic Drug Monitoring*, American Association of Clinical Chemistry (1984).

FIAs use fluorescent molecules as labels. Fluorescent molecules (fluorophores) are molecules which absorb light at one wavelength and emit light at another wavelength. See Burd, J. F., "Fluoroimmunoassay—Application to Therapeutic Drug Measurement," in P. Moyer et al., *Applied Therapeutic Drug Monitoring*, American Association of Clinical Chemistry (1984). Typically, an excitation pulse of radiation is directed onto or into a sample, followed by fluorescence of the sample, and the detection of the fluorescence radiation.

FIAs may be either heterogeneous or homogeneous. As noted above, homogeneous assays are usually simpler to perform and are thus, more amenable to automation. However, previously known homogeneous FIAs are less sensitive than heterogeneous FIAs because high background can limit sensitivity. The heterogeneous FIA procedures can detect smaller amounts of analyte than present homogenous FIAs, but only because the separation and washing steps in the assays serve to eliminate background interference from biological substances. In solid phase fluorescent assays the solid support can limit sensitivity at the wavelengths of presently used fluors. In many cases the support itself will fluoresce at wavelengths of commonly used fluors such as fluorescein (493 nm). FIAs also offer the advantage of using stable reagents.

Another assay method uses enzyme-enhanced fluorescence technology which combines microparticle capture and antigen-antibody reaction with an enzyme rate reaction using a fluorescent enzyme substrate. The rate reaction is monitored by steady state fluorometric measurement. In an enzyme-enhanced fluorescence assay, the analyte in question is "captured" by an antibody bound to a solid phase and the solid phase is washed. An enzyme is then bound to the captured analyte using an enzyme-anti analyte conjugate. Excess reactants are washed away and the amount of enzyme is measured by the addition of a non-fluorescent substrate. As the enzymatic reaction proceeds, the non-fluorescent substrate is converted to the fluorescent product. For example, an alkaline phosphatase-labeled antibody can be used to catalyze the hydrolysis of 4-methylumbelliferyl phosphate substrate to the fluorescent product methylumbelliferone. Thus, the rate at which the fluorescent product is generated is directly proportional to the concentration of analyte in the test solution. Enzyme-enhanced fluorescence assays, like EIAs, have the disadvantages associated with enzymes.

As discussed above, fluorescence is a phenomenon exhibited by certain substances, which causes them to emit light, usually in the visible range, when radiated by another light source. This is not reflection, but creation of new light. Current commercially available assay methods use fluorescein, which emits green light when radiated by a light source containing blue light.

In addition to fluorescing, fluorescein (and other fluorophores) emit polarized light. That is, the light emitted has the same direction of polarization as the incident polarized light, if the fluorescein molecule is held fixed with its transition moment parallel to the electric field of the excitation. The amount of polarization in the emission can be defined in terms of the intensity of the horizontally and vertically polarized light, as follows:

$$P=(Iv-Ih)/(Iv+Ih) \quad (1)$$

where

Iv=intensity of vertically polarized emission

Ih=intensity of horizontally polarized emission

The maximum, or limiting value of polarization, for fixed, randomly oriented molecules is 0.5 (Po).

A second equation (the Perrin equation) defines polarization in terms of physical parameters and Po:

$$1/P-1/3=(1/Po-1/3)(1+3t/r) \quad (2)$$

where t=fluorescence lifetime, a constant r=rotational relaxation time

Rotation relaxation is further defined for spherical molecules as $$r=3nV/RT \quad (3)$$

where

R=gas constant

T=temperature, °K n=solution viscosity

V=volume of molecule

The rotational relaxation time is a measure of the rate at which a molecule will rotate when free in a solution. Note that the rotational relaxation time will typically be dependent primarily on the molecular volume and shape, since solution viscosity and temperature will be essentially constant in a normal assay. Thus, rotational relaxation time, and consequently, polarization, are affected only by the hydrodynamic properties of the molecule. The smaller a molecule is, the smaller its rotational relaxation time, and the faster it rotates (e.g., r=1 nsec for fluorescein, 100 nsec for large antibody complexes). For a constant, small, fluorescence lifetime (4 nsec for fluorescein), a small molecule retains little of the original polarization when irradiated by polarized light, because the molecule rotates rapidly and then fluoresces. On the other hand, a large molecule rotates slowly and for the same fluorescence lifetime, still retains a large degree of the original polarization when it fluoresces.

This dependency of polarization on molecular size can be used to determine the presence or amount of drug.

Using a fluorescent polarizing probe in a competitive binding immunoassay provides a type of FIA called a fluorescence polarization immunoassay (FPIA). In this type of assay, the smaller the molecule is, the smaller its rotational relaxation time and the faster it rotates. Typically, antibody molecules are much larger than drug or drug-probe molecules. For example, r=1 nsec for fluorescein and 57 nsec for gamma globulin.

When there is a large amount of drug present, there are very few binding sites available for the drug-probe. As a result, most of the probe (fluorescein) is in the form of small drug-probe molecules. As these molecules rotate randomly and rapidly, a low polarization value results. When there is a small amount of drug present, much of the drug-probe is bound to the large antibody molecules. These molecules rotate slowly, so the emitted light will be highly polarized.

The relationship between polarization and drug concentration can be determined by creating a standard, or calibration, curve. This is done by running an assay using a range of known drug concentrations, from the lowest to highest expected concentrations, and plotting the resulting values of polarization. Thereafter, for a given value of polarization, the drug concentration can be determined from the standard curve.

One advantage of the polarization technique is the elimination of a step to separate unbound probe. Although the unbound tracer is not physically eliminated from the samples in FPIA, its contribution is readily assessed by the polarization.

Another advantage in the FPIA technique is lack of dependence on intensity. In equation (1) above for calculating polarization using intensity, the ratio makes the polarization value unitless, or independent of variations in the intensity. Unlike most assays using a light measurement, in which it is the intensity of the light that is correlated to drug concentration (so any variations in source light intensity will directly affect the sensitivity of the assay), the sensitivity of FPIAs is independent of intensity variations. Conventional FPIAs require separate measurements of both blank and sample.

Theoretically, fluorometry is capable of being the most sensitive of all analytic tools as it is possible to detect single photon events. A problem which has plagued fluorescence immunoassays has been discriminating the fluorescent signal of interest from background radiation. The intensity of signal from background radiation may be up to 10,000 times larger than the intensity of the fluorescent signal of interest.

The problem of background detection is particularly pronounced in assay of biological samples. Many of the current fluorescence assays use the fluorescent molecule, fluorescein. Fluorescein has an excitation maximum of 493 nm, and there are numerous substances in biological fluids with overlapping excitation and emission similar to fluorescein. For example, in the analysis of blood plasma, the presence of a naturally occurring fluorescable material, biliverdin, causes substantial background radiation. Such compounds are highly fluorescent and contribute significant background signals which interfere with the label's signal, thus limiting the sensitivity of assays using fluorescein labels.

Earlier attempts to overcome the problem of background radiation have met with limited success. One technique for overcoming the problem involves discriminating against background radiation on the basis of wavelength. Filters have been used to reject detected radiation at all but a narrowly defined wavelength band. This technique has been less than successful principally because the background radiation may also be at the same wavelength as the desired fluorescence signal, accordingly, still be passed through the filter and detected.

It has been recognized that for analysis of biological fluids, it would be desirable to use a dye or label which is excitable at radiations of wavelengths of greater than background radiation. However, even though the background fluorescence of serum falls off at wavelengths approaching 600 nm, significant decrease does not occur until 650 nm or greater. Previous attempts to create dyes of such wavelengths have been unsuccessful. See, e.g., Rotenberg, H. and Margarfit, R., *Biochem. Journal* 229:197 (1985); and D. J. R. Laurence, *Biochem. Journal* 51:168 (1952).

A second technique attempting to discriminate the desired fluorescent signal from the background is the so called time gating approach. Here, the fluorescent signal is observed in a short time window after the excitation. The time window may be varied both in its length and in its starting time. Through the use of the variable time window, the detected radiation may be observed at the maximal time for detection sensitivity. Historically, this technique has used a fluorophore of very long decay time (such as 1,000 nanoseconds) to allow the background fluorescence to substantially decay before detection of the fluorescent signal of interest. Generally however, long decay time fluorophores require longer times for overall analysis. Due to the long decay time, the light source cannot be pulsed rapidly to collect data, thus requiring additional time for final analysis.

Historically, there have been two excitation pulse formats for transient state fluorescent analysis. One format utilizes a single, relatively high power pulse which excites the fluorophore. The transient state is typically monitored by a high speed photomultiplier tube by monitoring the analog signal representative of current as a function of time. Single pulse systems require sufficiently high power to excite a large number of fluorescent molecules to make detection reliable. The other principal format for transient state fluorescent analysis is a digital format which utilizes repetitive excitation pulses. Ordinarily, pulses of relatively short, typically nanosecond duration, light with power in the microwatt range are repetitively supplied to the sample at rates varying from 1 to 10,000 Hz. Ordinarily, the excitation source is a lamp, such as a Xenon-lamp. Frequently, the decay curve is measured digitally by determining the time to receipt of a photon. One commercially available system uses repetitive pulses (such as at 5,000 Hz) and pulses the photomultiplier tube at increasingly longer times after the flash in order to obtain a time dependent intensity signal. Detection in such systems has proved to be very time consuming and insensitive. A single analysis can take on the order of one hour, even at relatively high fluorescable dye concentrations (e.g., $10^{-6}$M).

Recently, significant advances have been made in the area of fluorescable dyes. In one aspect, dyes being excitable by longer wavelength radiation, such as in the red and infrared wavelengths, are now available. These dyes are described in two commonly assigned patent applications: Arrhenius, U.S. patent application Ser. No. 701,449, filed May 15, 1991, now U.S. Pat. No. 5,403,928 entitled, "Fluorescent Marker Components and Fluorescent Probes," (which is a continuation-in-part of U.S. patent application Ser. No. 523,601, filed May 15, 1990 now abandoned), and Dandliker and Hsu, U.S. patent application Ser. No. 701,465, filed May 15, 1991, now abandoned entitled "Fluorescent Dyes Free of Aggregation and Serum Binding" (which is a continuation-in-part of U.S. patent application Ser. No. 524,212, filed May 15, 1990 now abandoned). These applications are incorporated herein by this reference.

Further significant advancements have been made in increasing sensitivity through data collection and analysis techniques. As disclosed in Dandliker et al., U.S. Pat. No. 4,877,965, entitled "Fluorometer," which is incorporated herein by this reference, time gating techniques are used in conjunction with data collection and analysis techniques to obtain an improved signal relative to the background. Generally, the '965 Patent considers the detected intensity as a function of time to be composed of signals from various sources, including the desired signal source, and various undesired background sources. Optimization of the desired signal is achieved through data collection and analysis techniques.

Further significant advancements have been made in the ability to measure relevant materials in immunoassays. For example, using the technique described in Dandliker, et al., U.S. patent application Ser. No. 490,770, filed Mar. 6, 1990, now U.S. Pat. No. 5,302,349, entitled "Transient State Luminescence Assays," (which is a continuation-in-part of U.S. patent application Ser. No. 365,420, filed Jun. 13, 1989 now abandoned) incorporated herein by this reference, allows the bound and free form of materials in a homogeneous assay to be determined. Generally, the technique requires measurement of the time-dependent decay of the intensity of parallel and perpendicular polarization components. By measuring the time-dependent decay of various polarization states, it is possible to determine the bound and free forms of materials such as haptens, peptides, or small proteins in a homogeneous analysis format. Significantly, no separation of the bound and free materials is required.

Despite the significant and promising improvements made in the field of fluorescable dyes, and in the data analysis aspects, the actual methods and apparatus for achieving and detecting fluorescence have heretofore remained relatively unchanged. Utilizing even the most sensitive and best equipment, analysis can take an hour or more, even at high concentrations of materials. When fluorometry is used for immunoassay in a clinical context, time for analysis and proper diagnosis can be absolutely critical. Patient survival can depend on accurate, timely analysis. Additionally, rapid testing would permit retests of patients without having them wait significant periods of time, resulting in more rapid and accurate diagnosis. As to sensitivity, it is extremely desirable to be able to detect minute amounts of fluorescable material. However, as the amount of fluorescable material in a sample decreases, the ratio of the signal increases. Further, since the time for analysis depends on the amount of fluorescent radiation received from the detector, low concentrations generally require substantially more time to analyze.

Heretofore, the time required for analysis has been prohibitively high. Known methods and apparatus for FIAs have failed to provide rapid and accurate diagnosis and analysis of samples. This has been so despite the clear and known desirability of the use of FIAs. For example, the drug digoxin, which is used to treat congestive heart failure, has a narrow therapeutic range (i.e., serum levels of 0.5 to 2.5 ng/ml and is generally toxic at concentrations greater than 2.1 ng/ml. Present assays using fluorescence-based methodologies require an extracting process to remove interfering substances, such as proteins, in order to detect digoxin at its therapeutic levels. This additional extraction step increases the time, cost and equipment needed to perform the assay.

From the above discussion it can be seen that, although many different types of immunoassays currently exist, none is satisfactory for measuring small quantities of target analytes in biological fluids such as serum, plasma and, especially, whole blood. Accordingly, an object of the present invention is to provide improved processes for assay of antigenic substances. More specifically, the present invention provides fluorescence assays which allow the detection of low levels of antigenic substances in biological samples such as serum, plasma and whole blood. The present invention also provides homogeneous fluorescence assays which allow rapid and accurate determination of low levels of antigenic substances in biological samples.

SUMMARY OF THE INVENTION

The present invention is directed to methods for determining the presence or amount of a target analyte in a sample by using, as a label for the target analyte or a receptor which is capable of specifically recognizing the target analyte, a fluorophore moiety comprising a luminescent substantially planar molecular structure coupled to two stabilizing polyoxyhydrocarbyl moieties, one located on either side of the planar molecular structure. By "target analyte" is meant the antigenic substance being assayed, for example an antigen. By "receptor" is meant a molecule or molecular component capable of specifically recognizing the target analyte. For example, an antibody may be a receptor for an antigen.

Use of such detectable labels or marker components in immunoassays is advantageous in that these labels have substantially the same intensities of parallel and perpendicular components of transient state fluorescence emission in the presence and absence of biological fluids such as serum. Thus, assay methods using these labels are capable of detecting low concentrations of target analyte in biological fluids.

The methods of the present invention are particularly suitable for use with the improved fluorescence detection system described in commonly assigned U.S. patent application Ser. No. 07/855,238 filed Mar. 23, 1992,entitled "Fluorometer Detection System," now U.S. Pat. No. 5,323, 008.

In one aspect, the present invention is directed toward competitive inhibition assay procedures utilizing particular labels. In this aspect, the present invention is directed to a method of determining the presence or amount of a target analyte by contacting a sample suspected of containing the target analyte with a known quantity of added target analyte or analog thereof linked to a fluorescent probe which includes a detectably labeled marker component made up of a fluorophore moiety which includes a luminescent substantially planar molecular structure coupled to two solubilizing polyoxyhydrocarbyl moieties, one located on either side of the planar molecular structure; contacting the sample with a receptor capable of specifically recognizing the target ligand; and determining either the amount of fluorescent probe bound to receptor or free fluorescent probe. The amount of bound or free fluorescent probe in the unknown samples may be compared with blank samples and samples containing known amounts of target analyte.

In a preferred embodiment, the resultant mixture of sample, fluorescent probe and receptor is diluted before measurement of the amount of bound and/or free fluorescent probe. The dilution step allows for greater sensitivity of the assay. Particularly preferred are dilutions of 2-fold to 100-fold, preferably about 7-fold to about 50-fold, and more preferably about 35-fold.

In one aspect, the present invention provides an improvement in immunoassay procedures which utilize a label for either the target analyte (or analog thereof) or the receptor. The improvement is the use of a fluorophore moiety comprising a luminescent substantially planar molecular structure coupled to two solubilizing polyoxyhydrocarbyl moieties, one located on either side of the planar molecular structure. Assays using this type of label are advantageous in that they are free of serum binding and aggregation and are therefore, especially suitable for testing biological samples such as serum, plasma, whole blood and urine.

In another aspect, the present invention provides a method for performing a "sandwich" or "two-site" immunoassay comprising the steps of:

(a) contacting a sample suspected of containing a target analyte with a first receptor capable of specifically recognizing said target analyte to form a complex of said target analyte and said first receptor, said first receptor being labeled with a fluorescent probe which comprises a fluorophore moiety comprising a luminescent substantially planar molecular structure coupled to two solubilized polyoxyhydrocarbyl moieties, one located on either side of the planar molecular structure;

(b) contacting the complex with a second receptor capable of specifically recognizing said target analyte to, said second receptor being bound to a solid carrier, to form a complex of said first labeled receptor, said target analyte and said second receptor bound to said solid carrier; and (c) measuring either the amount of labeled first receptor associated with said solid carrier or the amount of unreacted labeled first receptor.

A sandwich-type assay may be either a heterogeneous assay or a homogeneous assay. If it is heterogeneous, it may incorporate the additional step of separating the solid carrier from the unreacted labeled first receptor. Homogeneous assays are generally preferred because they are more rapid.

In another embodiment, the assay may incorporate the additional step of relating the amount of labeled first receptor measured in the unknown sample to the amount of labeled first receptor measured in a control sample free of said target analyte, or to the amount of labeled first receptor measured in samples containing known quantities of target analyte.

In another aspect, the present invention provides a method for a simultaneous sandwich-type assay comprising a method for determining the presence or amount of a target analyte in a sample comprising the steps of:

(a) simultaneously contacting a sample suspected of containing a target analyte with first and second receptors capable of specifically recognizing said target analyte, said first receptor being labeled with a fluorescent probe which comprises a fluorophore moiety comprising a luminescent substantially planar molecular structure coupled to two solubilized polyoxyhydrocarbyl moieties, one located on either side of the planar molecular structure, and said second receptor being bound to a solid carrier, to form a complex of said first receptor, said target analyte, and said second receptor; and (b) measuring either the amount of labeled first receptor associated with said solid carrier or the amount of unreacted labeled first receptor.

In another aspect, the present invention provides a method for a simultaneous sandwich-type assay comprising a method further comprising the step of relating the amount of labeled first receptor measured to the amount of labeled first receptor measured for a control sample free of said target analyte, or relating to the amount of labeled first receptor measured with the amount of labeled first receptor measured in samples containing known amounts of target analyte.

In another aspect, the present invention provides a sandwich-type fluorescence immunoassay method for measurement of a target analyte which is capable of recognizing two different receptors independently without mutual interference. The method utilizes two receptors, each of which is labeled with a different dye. For example, one receptor is labeled with a first dye having absorption and emission maxima of 680 nm and 690 nm, respectively, and the other receptor is labeled with a second dye having absorption and emission maxima of 695 and 705 nm, respectively. Detection and quantitation of the analyte can be made using either steady state or transient state measurements. In either case, for the example given, excitation would be at 680 nm and detection would be at 705 nm. This type of assay is based on energy transfer and is advantageous in that it is homogeneous.

In preferred embodiments the present invention is directed to immunoassay of biological fluids, including serum, plasma, whole blood and urine. Preferably, red blood cells in whole blood are lysed prior to assay of whole blood samples. Preferred methods of lysing red blood cells include addition of stearyl-lysolecithin, palmitoyl-lysolecithin and myristoyl lysolecithin.

Depending on the type of immunoassay used, the target analyte may be an antigen, a hapten or an antibody; and the receptor may be an antigen or antibody. The antibody may be polyclonal or monoclonal. Preferably, the antibody is a monoclonal antibody. Monoclonal antibodies useful in the present invention may be obtained by the Kohler & Milstein method reported in *Nature* 256:495–497 (1975). Alternatively, they may be produced by recombinant methods. *Science* 246:1275–1281 (1989).

In one embodiment, the target analyte is a drug or a metabolite of a drug. The drug may be a steroid, hormone, antiasthmatic, antineoplastic, antiarrhythmic, anticonvulsant, antiarthritic, antidepressant, or cardiac glycoside. Examples of such drugs include digoxin, digitoxin, theophylline, phenobarbital, thyroxine, N-acetylprocainamide, primidone, amikacin, gentamicin, netilmicin, tobramycin, carbamazepine, ethosuximide, valproic acid, disopyramide, lidocaine, procainamide, quinidine, methotrexate, amitriptyline, mortriptyline, imipramine, desipramine, vancomycin, and cyclosporine. In a preferred embodiment, the drug is digoxin.

In another embodiment, the target analyte is a peptide, for example, a peptide hormone such as luteinizing hormone, follicle stimulating hormone, human choriogonadotropin, thyroid stimulating hormone, angiotensin I, angiotensin II, prolactin or insulin. The peptide may also be a tumor marker such as carcinoembryonic antigen. Or, the peptide may be a virus or portion thereof, for example, rubella virus or a portion thereof.

The methods of the present invention provide ways of measuring target analytes in concentrations of from about $1\times10^{-5}$M/L to about $1\times10^{-13}$M/L, and particularly in the concentration range of from about $1\times10^{-9}$M/L to about $1\times10^{-12}$M/L. For measurement of drugs and their metabolites, the present methods allow measurement in the range from about $5\times10^{-9}$M/L to about $5\times10^{-12}$M/L, and particularly, concentrations of from about $1\times10^{-10}$M/L to about $5\times10^{-10}$M/L. For measurement of peptides, the present methods allow measurement in the range of from about $1\times10^{-11}$M/L to about $1\times10^{-12}$M/L.

The measurement of amount of fluorescent probe—bound or free or both—can be determined by measuring steady-state fluorescence or by measuring transient state fluorescence. In a preferred embodiment, the wavelength of light measured is greater than about 500 nm, preferably greater than about 650 nm, and more preferably greater than about 680 nm or 690 nm. Because the transient state detection system utilizes a laser diode, it is necessary for the dyes to have excitation maxima matched to the diode output wavelengths. Dyes have been made available to match other commercially available laser diodes have output wavelengths of 680, 690, 720, 750, or 780 nm. Thus, the wavelength of the light measured may be greater than about 680 nm, 690 nm, 720 nm, 750 nm or 780 nm. The further into the red region of the spectrum one moves, i.e., the greater the wavelength, the greater signal enrichment there is over background.

In a preferred embodiment, detection and quantitation is performed using transient state measurement. Transient state energy transfer offers improved measurements due to optimization of the wavelengths of absorption and emission, as well as due to optimization of the decay times of the first and second dyes. Such optimization allows removal of Rayleigh and Raman scattering, and achieving the best compromise between efficiency of transfer and the undesired direct excitation of the second dye by the first dye.

In one aspect, the present invention is directed to immunoassays using detectably labelled marker components which comprise a fluorophore moiety which comprises a substantially planar macrocyclic multidentate ligand coordinated to a central atom and two solubilizing polyoxyhydrocarbyl moieties, one linked on either side of the plane of the multidentate ligand to the central atom.

In one preferred aspect, the present invention is directed to immunoassays using a marker component comprising a fluorophore moiety which comprises a substantially planar multidentate macrocyclic ligand coordinated to a central atom capable of coordinating with two axial ligands which are coordinated to the central atom on either side of the macrocyclic ligand.

Marker components used in the immunoassays of the present invention comprise a macrocyclic multidentate ligand having two solubilizing polyoxyhydrocarbyl moieties one located on either side of the plane of the multidentate ligand exhibit no detectable non-specific binding to serum components, and exhibit no detectable solvent sensitivity. These marker components also exhibit enhanced decay times which approach their natural (fluorescent) lifetimes.

Preferred are fluorophores which produce fluorescent light efficiently, i.e., which are characterized by high absorbitivity at the appropriate wavelength and high fluorescence quantum yields. For certain applications, preferred fluorophores have measured fluorescence decay times on the order of at least 2 nanoseconds and exhibit a high degree of fluorescence polarization.

Preferred solubilizing polyoxyhydrocarbyl moieties include water soluble carbohydrates such as glucose, sucrose, maltotriose, and the like; water soluble carbohydrate derivatives such as gluconic acid and mannitol and oligo saccharides; and water soluble polymers such as polyvinylpyrrolidone, poly(vinylalcohol), poly (ethylenimine), polyacrylic acid, polyacrylamide, ethylene oxide copolymers such as Pluronic (a propylene oxide copolymer, available from BASF) and Tetronic (BASF) polyol surfactants; and polyethers, including water soluble polyoxyalkylene polymers, particularly poly(ethylene glycol) ("PEG") and poly(ethylene glycol) derivatives such as poly(ethylene glycol) methyl ether, poly(ethylene glycol) silicon derived ethers and the like.

In one aspect, the present invention is directed to immunoassays using marker components comprising a fluorophore moiety which comprises a substantially planar, multidentate macrocyclic ligand coordinated to a central atom capable of coordinating with two axial ligands and two polyoxyhydrocarbyl moieties which are attached as axial ligands to the central atom. Suitable central atoms are those to which may coordinate two axial ligands and which are not of high enough atomic number to cause extensive fluorescence quenching by transition to the triplet state. Preferred elements for the central atom include silicon, germanium, phosphorus, and tin, especially preferred are silicon and germanium.

Depending on the type of immunoassay, these marker components may be used as labels for labelling an analyte, antigen, antibody or other molecule. These marker components may be optionally functionalized so as to include a linker arm which allows the marker component to be linked to the analyte, antigen, antibody or other molecule. A variety of linker arms which may be suited to this purpose. The marker component is linked to the analyte, antigen, antibody or other molecule using conventional techniques.

The present invention is also directed to the use of divalent peptide derivatives as analogs for large molecules in immunoassays. Preferably, a divalent hapten consisting of two epitopes of the same specificity connected by a linker about 10 nm long is used to bind to a single antibody molecule, requiring approximately 26 residues.

The present invention also includes assay methods of involving cellular receptors located on the plasma membrane or isolated from cytosols and synthetic ligand binders obtained by molecular imprinting.

Accordingly, it is a principal object of this invention to provide improved FIAs with greatly enhanced sensitivity. It is yet another object of this invention to provide FIA methods which allow rapid and accurate determinations, often within a matter of minutes.

It is an object of this invention to provide FIA methods which are capable of measuring extremely low concentrations of fluorescable material.

It is an object of this invention to provide FIA methods useful for the clinical setting in that they are rapid and accurate, of relatively low cost and capable of use with unmodified biological samples, such as whole blood.

It is a further object of this invention to provide FIA methods particularly adapted to exploit the improved fluorescence detection system, described in U.S. patent application entitled "Fluorometer Detection System," Lyon & Lyon Docket No. 195/129, referenced above.

It is a further object of this invention to provide homogeneous "mix and read" digoxin assay methods which can be used to determine the level of digoxin in serum, plasma or whole blood.

It is a further object of this invention to provide an assay for peptides, for example, for a rubella virus or a portion thereof.

The present invention also provides particular fluorescent probes for use in immunoassays, for instance, see Examples 3 and 11–18 below.

Definitions

As used herein, the following terms have the following meanings unless expressly stated to the contrary:

The term "target analyte" refers to the compound or compound to be measured in an assay which may be any compound for which a receptor naturally exists or can be prepared which is mono- or polyepitopic, antigenic or haptenic, a single or plurality of compounds which share at least one common epitopic site or a receptor. By "analog" of a target analyte is meant a compound or compounds capable of competing with the target analyte for binding to a receptor.

The term "axial ligand" refers to a substituent which, together with a macrocyclic ligand, forms a coordination complex with a central atom. The axial ligand lies normal to the plane described by the macrocyclic ligand.

The term "fluorescent probe" refers to a marker component comprising a fluorophore moiety which is bonded to or coordinates either directly or via a linker arm to an analyte, antigen, hapten, antibody or other molecule which is used in an assay, such as a fluoroimmunoassay to determine the presence of and/or quantitate a substance of interest.

The term "solvent sensitivity" refers to changes in the fluorescence behavior of a molecule depending on the solvent system in use, most notably referring to differences in fluorescence behavior in aqueous solution in comparison with organic solvents (such as DMF). Many fluorophores which exhibit high fluorescence intensity in organic solvents such as DMF show substantially decreased fluorescence intensity in aqueous solution.

Fluorescence intensity is related to sample concentration and the intensity of the exciting radiation. The fluorescence intensity of a particular dye can be correlated to its characteristic light absorptivity (extinction coefficient) and fluorescence quantum efficiency, as well as environmental factors.

The term "specific binding pair" refers to two different molecules (or compositions) wherein one of the molecules has an area on the surface or in a cavity which specifically recognizes and binds to a particular spatial and polar organization of the other molecule or molecular complex involving other molecules.

The term "binding partner" refers to a molecule or molecular complex which is capable of specifically recognizing or being recognized by a particular molecule or molecular complex.

The term "bound" refers to the condition in which a binding interaction has been formed between a molecule and its specific binding partner.

The term "decay time" is the time which must elapse in order for the concentration of excited molecules to decrease from its initial concentration to 1/e of that value.

The term "receptor" refers to a molecule or molecular complex which is capable of specifically recognizing or being recognized by a target analyte or analog thereof.

BRIEF DESCRIPTION OF THE DRAWINGS

FIG. 5 shows serum interactions of purified caged dicarboxy silicon phthalocyanine dye.

FIG. 10 depicts the structure of caged dicarboxy silicon phthalocyanine digoxin probe.

FIG. 22 depicts digoxin correlation—TDx® Serum vs. FAST-60 Whole Blood.

FIG. 23 depicts digoxin correlation—Stratus® Serum vs. FAST-60 Whole Blood.

FIG. 24 depicts digoxin correlation—FAST-60 Serum vs. FAST-60 Whole Blood.

DETAILED DESCRIPTION OF THE INVENTION

Figure 1:
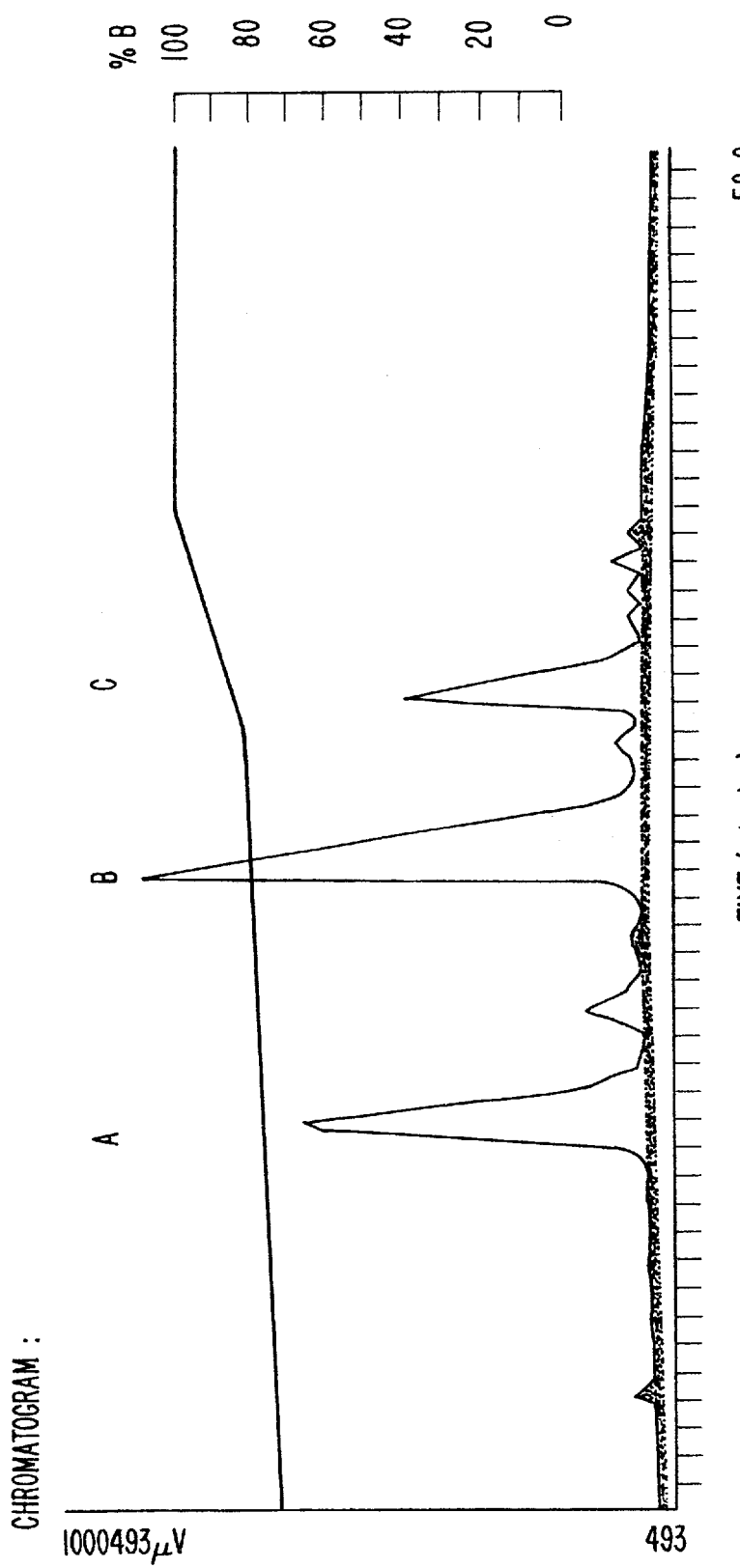
FIG. 1 depicts an HPLC analysis of crude caged dicarboxy silicon phthalocyanine dye preparation.

The present invention provides fluorescence immunoassay methods which have dramatic increases in sensitivity over previous methods, which can be easily performed because they require no separation step, and which can be used to detect and quantitate low levels of target analyte in biological samples such as serum, plasma, whole blood and urine. The FIAs of the present invention may be performed in small samples. For example, a digoxin assay may be performed on a 20 µl sample of serum, plasma or whole blood, and the assay may be performed in about five minutes. The ability to perform FIAs on whole blood samples is particularly significant because it allows assays to be performed at locations closer to the patient, such as physicians' offices and emergency rooms. The capability of performing FIAs rapidly is important because, in a clinical context, patient survival can depend on accurate, timely results.

The concept of sensitivity in fluorescence measurements can be usefully quantified by specifying the concentration of the fluorophore in question at which the fluorescence intensity from the fluorophore is equal to the intensity from the background. This manner of expressing sensitivity emphasizes the fact that the sensitivity of fluorescence measurements is almost always determined by the ability to discriminate between "signal" and "background" and not by the absolute number of photons available from the "signal."

The present invention provides methods for FIAs which solve the problem with discriminating against background radiation on the basis of wavelength. The probes used in the method of the invention have excitation (and emission) wavelengths greater than about 650 nm, preferably greater than 680 nm. This wavelength shift into the infra-red range decreases background fluorescence, i.e., increases signal-to-background ratio. This decrease in background fluorescence allows the use of fluorophore at far lower concentrations than previously used in homogeneous FIAs.

The probes used in the present assay methods have low dielectric constants, which applicants believe tend to increase the Van der Waal interactions and hydrogen bonding, thus accelerating the antigen/antibody reaction. In addition, applicants believe that these probes compete for the water of hydration, thus potentiating the antigen/antibody reaction. In other words, the probes not only substantially decrease non-specific bindings to serum components, but applicants believe that they potentiate the immunochemical reaction.

For fluorescence polarization assays, the present invention provides a further increase in sensitivity by measuring transient state fluorescence rather than the steady state signal. In the steady state mode the signal is constant over time enabling the determination of one experimental parameter, e.g., the polarization or the anisotropy, both of which are related to molecular rotational motion. In the transient state mode the signals vary in a systematic way with time. This variation represents a complex summation of the rates of decay and of molecular rotation as it changes from moment to moment in time.

The increase in sensitivity from transient state measurements stems from two sources. First, that portion of the background due to Rayleigh and Raman scattering disappears in about $10^{15}$ sec and so is cleanly removed before the transient state measurements start. This portion of background is normally an important part of the total in steady state measurements.

Above and beyond the removal of scattering, the transient state measurements provide an additional powerful means to discriminate between the desired signal and the remaining fluorescence portion of the background. This discrimination rests upon the time dependence of the polarized components in the fluorescence decay and makes it possible to extract the desired signal only, simultaneously on the basis of the rate of decay of the excited state and the rate of decay of the rotational distribution imprinted by the excitation. Thus, transient state methods allow signal to be distinguished from background in ways not possible with steady state information alone.

In addition to these features, the probes exhibit a high degree of polarization, necessary for mix and read (homogeneous) fluorescence polarization assays. This increase in polarization translates into increased sensitivity.

The methods of the present invention are particularly useful when used with a time-correlated transient state detection system, as described in commonly assigned Studholme, et al., U.S. patent application Ser No. 07/855, 238 filed Mar. 23, 1992, entitled "Fluorometer Detection System," now U.S. Pat. No. 5,323,008 That system features transient detection along with detection of the time-dependent polarization of the sample. The system uses a laser diode which can be modulated at very high frequencies, e.g., 10 MHz rate, and exhibits high output power. Typically the laser "on" time is approximately 2–3 nanoseconds. Photons from the solution are detected using a photomultiplier tube (PMT) operating in a single photon counting mode. The photon event along with the relative time of the photon event as compared with the laser pulse time is determined. By storing the individual photon event times a histogram of frequency of photons as a function of time is generated.

Data obtained in this manner can be analyzed as described in Dandliker et al., U.S. Pat. No. 4,877,965, entitled "Fluorometer" or as described by Studholme, et al., U.S. patent application Ser. No. 07/855,238, filed Mar. 3,1992, entitled, "Fluorometer Detection System," now U.S. Pat. No. 5,323, 008.

The methods of the present invention also include the use of divalent peptide derivatives as analogs for large molecules in immunoassays. Both polyclonal and monoclonal antibody molecules are divalent. Due to the "chelate effect," the binding of a low molecular weight mimic or analog of a larger molecule will be stronger and dissociation from the antibody will be slower if both antibody binding sites are utilized in the bonding. It is within the scope of the present invention to arrange the structure of the peptide analog to have two identical sequences joined together by a linker of suitable length so as to place the two peptide sequences, in their normal configuration in solution, in the most favorable position for reaction with the two sites on the same antibody molecule.

Preferably, several such unspecific, divalent analogs are used as a cocktail, rather than combining more than one epitope in the same analog molecule. The latter arrangement would permit cross linking of perhaps many antibody molecules which might be preferable in solid phase assays in which the formation of chains and cycles could aid in adhering to a surface. Conversely, having two identical epitopes on the same analog molecule may "inhibit" polymerization by strongly favoring, by proximity factors, reaction with two sites on the same molecule.

The use of divalent peptide derivatives as analogs for large molecules in immunoassays is preferred in solution, especially in conjunction with dilution jump, due to the tighter binding afforded by the "chelate effect," resulting in an increase in the sensitivity of the immunoassay.

Preferably, a divalent hapten consisting of two epitopes of the same specificity connected by a linker about 10 nm long is used to bind to a single antibody molecule. Taking into account the bond distances and angles for simple peptides (L. Pauling, *The Nature of the Chemical Bond*, Cornell University Press (1960), p. 498) and assuming a length of 0.380 nm per amino acid residue, this would require approximately 26 residues for a 10 nm length.

One approach for designing a divalent hapten with such a linker is to synthesize the epitope with a 13 residue linker terminating in a primary amino group. This peptide is then reacted with the bis (3-isocyanatopropyldimethylsilyl) derivative of dihydroxysilicon phthalocyanine. The resulting structure has the phthalocyaninine moiety with two axial substituents, one on either side of the molecular plane, each consisting of a thirteen residue peptide linker leading to the peptide epitope. The molecular plane of the dye moiety is perpendicular to the direction of the linker. After combination of the two peptide epitopes with the two binding sites of the same antibody molecule the dye moiety may be located midway between the two arms of the Y-shaped antibody molecule. The polarization changes obtainable with this type of structure may not be as great as if the dye were linked through a peripheral rather than an axial bond, and the absence of PEG may result in non-specific binding. However, if the dye moiety is held close to the antibody surface between the two Fab fragments after binding, it may prove to be quite protected and rotate with the longest rotational decay time of the antibody (since the molecular plane of the dye may lie parallel to the long axis of the antibody).

Alternatively, a divalent peptide hapten may be designed to utilize the PEG protected dye linked through a peripheral carboxyl to an amino group on the linker or on one of the peptide epitopes, e.g., the linkage could be the c-amino group of a lysine residue located approximately midway on an interconnecting chain between the two peptide epitopes.

Immunoassays, a class of ligand binding assays, depend upon the strong and selective binding of some analyte of interest to antibody specific for that analyte. Other molecular structures that have similar strong and selective binding for such an analyte can serve equally well in designing an assay and such structures may have some inherent advantages over antibody. For example, molecules which may have desirable properties in this context include cellular receptors located on the plasma membrane or isolated from cytosols and synthetic ligand binders obtained by a process known as "molecular imprinting."

The sensitivity of a ligand binding assay depends upon the binding affinity of association constant (K) of the reaction between the analyte and the binding molecule. For classical cytosolic steroid hormone receptors these Ks are of the order of $10^9$ $M^{-1}$. In recent work with molecular imprinting of synthetic polymers the binding constant for diazepam was found to be about $10^8$ $M^{-1}$ (Vlatakis et al., *Nature* 361: 645–647 (1993)). By contrast, the highest Ks for antibody binding are of the order of $10^{12}$ $M^{-1}$ for ligands such as fluorescein and digoxin.

The magnitude of these Ks suggest that antibodies bind far more tightly than do receptors or molecular imprints. Binding processes are symmetrical and the observed K depends upon both the "receptor" and the "ligand" and the distinction between the two is made for convenience. Applicants believe that because relatively few Ks have been measured for receptors or molecular imprints, there is no reason that the binding by these molecules should not be potentially as tight as by antibody. Molecular imprints also have the inherent advantage of being tailored for one specific molecule and the Ks can be improved by the proper placement of hydrophobic, polar and ionic groups in the binding sites. Moreover, because these molecules are synthetic, once the optimal structure is known large amounts should be readily obtainable.

Thus, the present invention includes methods of involving cellular receptors located on the plasma membrane or isolated from cytosols and synthetic ligand binders obtained by molecular imprinting.

I. PREFERRED MARKER COMPONENTS

The following is a brief description of the preferred marker components to be used in the fluorescence immunoassays of the present invention. A more complete discussion is found in commonly assigned U.S. patent applications Ser. Nos. 701,449 now U.S. Pat. No 5,403,928 and 701,465 now abandoned, which, as noted above, have been incorporated herein by reference.

A. Preferred Fluorophore Moieties

Suitable fluorophore moieties comprise a luminescent substantially planar molecular structure. Preferred are fluorophore moieties in which the luminescent substantially planar molecular structure comprises a substantially planar macrocyclic multidentate ligand which coordinates a central atom which may coordinate with two axial ligands, one on either side of the macrocyclic ligand (i.e. having a trans orientation).

Preferred central atoms are elements which may form octahedral coordination complexes containing two ligands with a trans or axial orientation, on either side and perpendicular to the planar macrocyclic ligand. For use as fluorescent marker components in certain applications the central atom should not have too high atomic number (about 30 or less) so that fluorescence is not diminished through coupling interaction with orbitals of the central atom.

Preferred multidentate ligands include nitrogen-containing macrocycles which have conjugated ring systems with pi-electrons. These macrocycles may be optionally substituted, including substitution on bridging carbons or on nitrogens. Suitable macrocycles include derivatives of porphyrins, azaporphyrins, corrins, sapphyrins and porphycenes and other like macrocycles which contain electrons which are extensively delocalized. In view of the fact that they incorporate many of the above-noted characteristics, an especially preferred class of macrocycles comprise porphyrin derivatives, and azaporphyrin derivatives (porphyrin derivatives wherein at least one of the bridging carbons is replaced by a nitrogen atom). Azaporphyrin derivatives include derivatives of mono-, di- and triazaporphyrin and porphyrazine. These macrocycles may optionally have fused aromatic rings. These azaporphyrin derivatives include phthalocyanine, benzotriazaporphyrin and naphthalocyanine and their derivatives. The preparation and fluorescent qualities of many of these compounds are known and some are available commercially. See U.S. patent application Ser. No. 701,465 now abandoned, and references cited therein, particularly, references 2–5 in that application.

For certain applications, such as fluorescence polarization assays, preferred are azaporphyrin derivatives which exhibit a high degree of polarization, that is, those which emit strongly polarized light. For these applications, preferred are macrocycles having lower degrees of symmetry, preferably having lower symmetry than $D_{4h}$. One preferred group includes macrocycles having at least one fused aromatic ring. Thus, preferred macrocycles include azaporphyrin derivatives having fused aromatic rings at positions which result in decreased symmetry. Preferred classes of azaporphyrin derivatives comprise derivatives of monoazaporphyrin, diazaporphyrin, and triazaporphyrin having lower than $D_{4h}$ symmetry.

B. Preferred Solubilizing Polyoxyhydrocarbyl Moieties

Preferred solubilizing polyoxyhydrocarbyl moieties include water soluble carbohydrates such as glucose, sucrose, maltotriose and the like; water soluble carbohydrate derivatives such as gluconic acid and mannitol, and oligosaccharides; polypeptides such as polysine and naturally occurring proteins; and water soluble polymers such as polyvinylpyrrolidone, poly(vinyl alcohol), poly (ethylenimine), polyacrylic acid, polyacrylamide, ethylene oxide copolymers such as Pluronic™ (a polyether) and Tetronic™ (BASF) polyol surfactants and, in particular, polyethers such as other polyoxyalkylenes including poly (ethylene glycol), or other water soluble mixed oxyalkylene polymers, and the like.

A particularly preferred class of solubilizing polyoxyhydrocarbyl moieties comprises poly(ethylene glycol) (PEG) and poly(ethylene glycol) derivatives, such as poly(ethylene glycol) monomethyl ether. Other suitable PEG derivatives include PEG-silicon derived ethers. Many of these polymers are commercially available in a variety of molecular weights. Others may be conveniently prepared from commercially available materials, such as by coupling of an amino-PEG to a haloalkyl silyl or silane moiety. When linked to a fluorophore moiety, these polyoxyhydrocarbyl moieties impart particularly advantageous qualities of solubility in aqueous solution with improved measured fluorescence decay time, and improved fluorescence intensity. Moreover, the resulting marker components are water soluble and show decreased non-specific binding, especially decreased binding to serum albumin which has heretofore been a problem with certain fluorophores, particularly porphyrin or phthalocyanine dyes which have been functionalized with groups such as sulfonate to impart increased water solubility to the molecule. Non-specific binding of fluorophore or marker component impairs the accuracy of the resulting immunoassay. These marker components which comprise fluorophore linked to PEG may also exhibit improved fluorescence intensity in aqueous solution with decreased quenching.

Suitable PEGs may vary in molecular weight from about 200 to about 20,000 or more. Choice of a particular molecular weight may depend on the particular fluorophore chosen and its molecular weight and degree of hydrophobicity, as well as the particular application for which the fluorophore-PEG complex is to be used.

C. Absorbance and Polarization Behavior of Preferred Marker Components

These marker components which comprise a central atom (for example, silicon) coupled to two PEG moieties may be characterized by measurements of transient state fluorescence. In such measurements the intensity of the two components polarized either parallel or perpendicular to the direction of polarization of the exciting pulse is monitored over a time period equal to about 3 times the decay time of the marker component. Such curves reflect extinction coefficient, quantum yield, decay time and state of polarization and supply sensitive indications on the chemical and physical condition of the marker component.

For example, if the excited state is being deactivated or converted to the triplet state the overall intensities are lowered and the decay times shortened. If the rotary brownian motion of the molecule is being altered by an increase in viscosity or by being bound to a large molecule, the ratio of the intensity of the parallel to the perpendicular component is increased.

Some marker components according to the present invention show, within experimental error of about 5%, the same intensities, decay time and polarization in DMF (an organic solvent) as in SAP (saline azide phosphate, an aqueous neutral buffer). To some extent these properties are shared by other marker component preparations. A distinctive and important property of the marker components of the present invention is a insensitivity to (and lack of binding to) the components in serum which is evidenced by a lack of any measured effect of serum on the intensities, decay time or relative magnitudes of the polarized components of the fluorescence. This property is crucial for the marker components to be useful for applications such as assays using biological materials.

D. Preparation Of Preferred Marker Components

According to one method of preparing the preferred marker components of the present invention, the appropriate fluorophore moiety having hydroxy or halide groups as axial ligands is reacted with a reactive form of the solubilizing polyoxyhydrocarbyl moiety in a ligand exchange reaction according to the general reaction scheme:

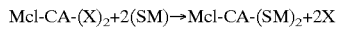

Mcl-CA-(X)$_2$+2(SM)→Mcl-CA-(SM)$_2$+2X wherein Mcl denotes the macrocyclic ligand, CA the central atom, X the displaced ligand and SM the solubilizing moiety. This reaction may be carried out neat or, if desired, in solvent. Suitable solvents include quinoline, THF, DMF, imidazole and the like. Suitable reaction temperatures may vary, depending on the nature of the macrocyclic starting material and the solubilizing group. The reaction is generally complete in about 2 minutes to about 24 hours. The reaction mixture can be conveniently heated under reflux or by means such as a sand bath. For convenience, the reaction may be carried out at ambient pressure.

It is believed that this reaction takes place in two steps, with one polyoxyhydrocarbyl group coordinating as an axial ligand at a time.

When used as fluorescent labels in fluorescence immunoassays, these marker components may be linked to one member of a specific binding pair ("labelled binding partner") or an analog of such a member. The marker component may be directly attached or conjugated thereto or attached or conjugated via a linker arm.

II. CAGED DICARBOXY SILICON PHTHALOCYANINE DYE

EXAMPLE 1

Preparation of a Caged Dicarboxy Silicon Phthalocyanine Dye

Unless otherwise stated, all chemicals used in the synthesis of phthalocyanine derivatives were purchased from Aldrich Chemical Co., Milwaukee, Wis. Amino-terminated polyethylene glycol and phthalocyanine derivatives were synthesized according to published procedures. See, e.g., Reference 18 of U.S. patent application Ser. No. 701,449.

A. Preparation of Diiminoisoindoline

In a three-neck, 100 ml round-bottom flask fitted with a reflux condenser and a gas inlet tube was placed phthalonitrile (12.8 g), and methanol (50 ml), and the mixture was stirred while ammonia gas was slowly introduced. In order to prevent the possible flow of the reaction mixture into the ammonia source, and in-line trap was employed. After the reaction mixture appeared to be saturated with ammonia, 0.33 g of dry potassium tert-butoxide was added with stirring.

Stirring was continued and the reaction mixture was heated to reflux for three hours with continued introduction of ammonia. Care was taken to avoid fouling of the gas inlet with the crystalline product. At the end of the reflux period a pale green solid had formed. The solid was collected by filtration and washed with a small volume of cold (4° C.) methanol. (This compound is appreciably soluble in methanol.) This material was dried and used for the next step without further purification. Yield was 7 g (about 50%).

B. Preparation of Dicyanodiiminisoindoline 1,2,4,5-Tetracyanobenzene (Pfaltz & Bauer, 0.5 g, 2.8 mMol) was suspended in methanol (10 ml) in a three-neck round-bottom flask fitted with a reflux condenser and a gas inlet tube. The mixture was stirred at 25° C. without external cooling while ammonia gas was rapidly introduced. During the first two minutes of ammonia introduction the temperature of the reaction mixture rose to greater than 50° C. and the suspended solid dissolved completely. Within 5 minutes a precipitate began to form. Stirring at 40°–50° C. with slow introduction of ammonia was continued for 1 hour. The precipitated solid was collected by filtration, washed with methanol, and dried. This product exhibited a very low solubility in methanol.

C. Preparation of Dicyanosiliconphthalocyanine Dichloride (Compound I)

In a dry 50 ml round-bottom flask was placed dicyanodiiminoisoindoline (350 mg, 1.8 mmol) along with diiminoisoindoline (1.0 g, 6.9 mMol) and quinoline (Fluka, 20 ml). The mixture was stirred at 25° C. while silicon tetrachloride (Aldrich, 2.0 ml, 18 mMol) was added dropwise over a period of 1 minute. The flask was then fitted with a reflux condenser (using teflon tape) and a calcium chloride drying tube and stirred for one minute at 25° C.

At this time the reaction flask was lowered into a large oil bath maintained at 180°–185° C. and efficient magnetic stirring was continued for 30 minutes. The oil bath was then removed and the contents of the flask were allowed to cool to room temperature.

The dark reaction mixture was carefully treated with water (5 ml) and then diluted with 45 ml of a 30% HCl solution. The resulting dark precipitate was collected by filtration on a 10 cm Buchner funnel. Washing with water and then acetone left a blue solid (1 gram) which was air dried and used without further purification for the next reaction step.

D. Hydrolysis of Dicyanosiliconphthalocyanine Dichloride (Compound II)

The crude dicyanophthalocyanine from step (C) (1 gram) was placed in a flask with a stir bar and 6 ml of concentrated sulfuric acid and stirred at 50° C. overnight. The mixture was then carefully diluted with 4 ml water and heated to 100° C. for an additional 20 hours. Cooling and dilution with water (20 ml) gave a blue precipitate which was collected by filtration and washed with water. The solid was then transferred to a flask along with a stir bar and 20 ml of a 1.0M potassium carbonate solution and stirred and heated at reflux for one hour. The suspension was then slowly and carefully acidified with concentrated HCl and then filtered and the resulting solid was washed with water and acetone and dried in a desiccator. This material (0.7 g) was used without further purification in the next step.

E. Preparation of 2,3-Dicarboxyphthalocyaninato-bis-[3-(1H-imidazol-1-ylcarbonyl)aminopropyldimethylsilanolato] silicon (Compound III)

The crude dicarboxy silicon phthalocyanine dihydroxide from step (D) (85 mg) was placed in a vial along with a stir bar and imidazole (160 mg, 2.3 mmol) and 1 ml of dry DMF. The mixture was stirred for 5 minutes at 25° C. and then 3-isocyanatopropyldimethylchlorosilane (Petrarch, 110 μl, 0.68 mMol) was added to the stirred mixture over a period of 0.5 minutes. The vial was capped in order to exclude moisture and stirring at 25° C. was continued for 20–40 hours. (A 40 hour reaction time appeared to result in an improved yield.) The vial was then opened and the dark blue mixture was diluted with methanol (4 ml) and filtered through #545 celite to remove solids. The filtrate was concentrated on a rotovap using high vacuum and a water bath maintained at 40° C. The dark residue was then slurried with silica gel (1–3 g) and methanol (5 ml) and the methanol was removed on a rotovap under aspirator pressure. The blue residue was then suspended in toluene and transferred to a silica gel column prepared from 15 ml 23–400 mesh silica gel (EM Science) and toluene. This column had been washed with 50% methanol in toluene.

Increasing the solvent polarity by increasing the methanol content of the solvent to 16% brought about the migration of a distinct band which was collected. This material was saved but not used for further transformations.

Increasing the solvent polarity by slowly increasing the methanol content of the eluant to 30% brought about the migration of a second blue band which was collected within a 20 ml volume of 30% methanol. This material was transferred to a round bottom flask. Removal of solvent on a rotovap under high vacuum at 25° C. left a residue which appeared to include an appreciable quantity of imidazole along with the blue dye. This material was used without further purification for the next step. The yield of compound III was approximately 3 mg.

F. Preparation of Amine-Terminated Polyethylene Glycol

Poly(ethylene glycol) monomethyl ether (Aldrich, average M.W. 2000, 10 g, 5 mMol) was placed in a 100 ml round-bottom flask along with a stir bar and 55 ml toluene. The flask was fitted with a short-path distillation apparatus and immersed in a heating bath. Toluene was slowly distilled at 760 mm Hg until the distillate was no longer cloudy. This required the removal of about 15 ml of toluene.

The relatively water-free PEG solution was allowed to cool to 40° C. When this temperature had been attained, carbonyldiimidazole (Aldrich, 1.2 g, 7.5 mmol) was added to the stirred solution in one portion. Stirring at 30°–40° C. was continued overnight with protection from atmospheric moisture.

Water (100 $\mu$l, 3.75 mMol) was then added to the reaction mixture and efficient magnetic stirring was continued until the evolution of $CO_2$ gas could no longer be observed (about 15 minutes).

Most of the toluene was removed on the rotovap at 30° C. under high vacuum leaving a viscous, colorless oil. This material was diluted with isopropanol (20 ml) and added to a stirred solution of 1,2 ethylenediamine (Fluka, 6.7 ml, 100 mMol) in isopropanol (15 ml) over a period of five minutes. After completion of the addition the clear solution was maintained at 40° C. for four hours.

At this time isopropanol (150 ml) was added to the reaction mixture. The diluted solution was allowed to stand at 4° C. overnight, resulting in the formation of a voluminous mass of white crystals. This solid was collected on a 10 cm Buchner funnel, and subsequently recrystallized from isopropanol.

Drying under high vacuum over sulfuric acid afforded 7 grams of the crude amine, suitable for use as a reagent. Structure of the product was confirmed by IR.

The amine content of polyethyleneglycol amine, prepared as outlined above, was determined to be >70 mole % by the following method:

25 ml of 10% solution of the amine in methanol was allowed to react with an equal volume of a 6% solution of maleic anhydride in THF. The reaction mixture was allowed to stand for 0.5 hours at 25° C. and was then diluted to 1.0 ml with methanol. A 5 $\mu$l aliquot of this final solution was injected on to an analytical RP18 reverse phase HPLC column using 30% methanol in water as the initial mobile phase. Using n-propylamine as an internal standard allowed for accurate-quantification of the UV-absorbing acyl-PEG derivative, which was eluted in 80% methanol and was detected at 254 nm.

Analysis of the infrared spectrum of amine-terminated PEG can also provide a convenient means of estimating the product yield.

G. Reaction of Compound III with Amine-Terminated Polyethylene Glycol (Compound IV)

The product of step (E) (Compound III) (3 mg, $5\times10^{-3}$ mMol), which had been obtained in partially purified form by chromatography on silica gel, was dissolved in methanol (1 ml). The mixture was stirred while amine-terminated PEG (product of step (F), 100 mg, $5\times10^{-2}$ mMol) was added. The resulting deep blue solution was heated to reflux for one hour.

Removal of methanol under aspirator pressure at 25° C. left a viscous blue oil which was taken up in water (0.5 ml) and applied to a small (10 ml wet volume) DEAE Sephadex anion ion exchange column (Pharmacia, 3.5 meq/g, 40–120 micron, basic form<1M $K_2CO_3$). The water-soluble blue dye was retained quantitatively by the column. The column was washed with water (15 ml) and the blue dye was then eluted in greater than 70% yield with 10–20 ml of a 15% aqueous acetic acid solution.

Water and acetic acid were removed under high vacuum and the blue residue was taken up in a small volume of methanol and applied to a C18 reverse phase semi-preparative HPLC column. The major product, detected at 675 nm as a single peak, eluted with 80% aqueous methanol (containing 0.6% acetic acid) and comprised about 50% of the sum of the material which was recovered from the column. Fractions containing the major product were combined and solvent was removed under high vacuum leaving a blue residue (approx. 0.5 mg, $10^{-7}$ mMol).

NMR ($DCCl_3$: $\delta$–2.85 (5, 12H), $\delta$–2.29 (m, 4H), $\delta$–1.30 (m, 4H), $\delta$1.80 (m, 4H), $\delta$3.6 (br.s, 300–400H), $\delta$8.39 (m, 6H), $\delta$9.68 (m, 6H), $\delta$10.56 (S, 2H). Note: Because the sample had been previously dissolved in $D_2O$, the acidic protons, RCOOH, were not observed.

Figure 2A:
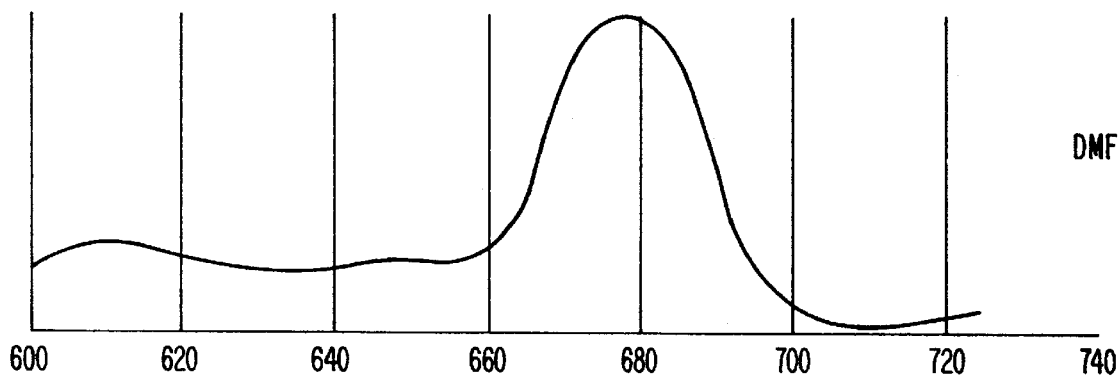
FIG. 2 shows the absorbance of caged dicarboxy silicon phthalocyanine dye in various solvents.
Figure 2B:
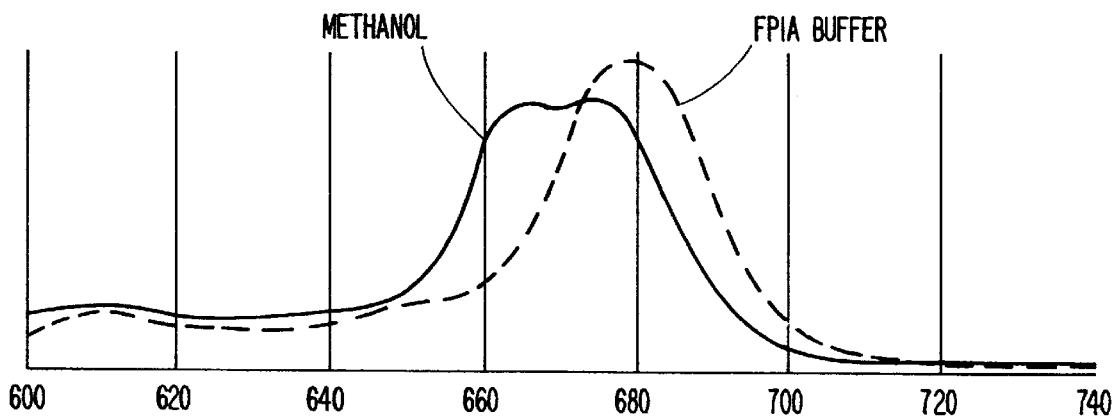

FIG. 1 is a typical HPLC chromatogram of this preparation (compound IV). The fraction containing compound IV, with retention time of approximately 25–26 minutes, was designated "B" fraction. The yields for a typical dye preparation range from 25–65% of this fraction. Fractions from several chromatographic runs were pooled, dried in vacuo and analyzed. The absorbance of the "B" fraction was measured in a Perkin-Elmer spectrophotometer using various solvents. As shown in FIG. 2, very little "solvent sensitivity" can be seen between methanol, dimethylformamide and FPIA buffer (100 nM phosphate pH 7.5 with 0.01% gamma globulin).

The fluorescence decay time for the "B" fraction was determined to be 4.3 nanoseconds. The measurements were made on the "Diatron Analog System". In the Diatron Analog System, transient-state fluorescence was detected using a high speed, "gateable" photo-multiplier tube (PMT). The combination of being able to rapidly change the PMT gain and the use of high power laser pulses enabled the viewing of the fluorescence decay of dyes with a single excitation pulse. In practice, many pulses were averaged to obtain improved data. These analog signals coming from the PMT were captured by a digitizer which took the analog signal and cut it into 512 time bins for analysis.

Figure 3:
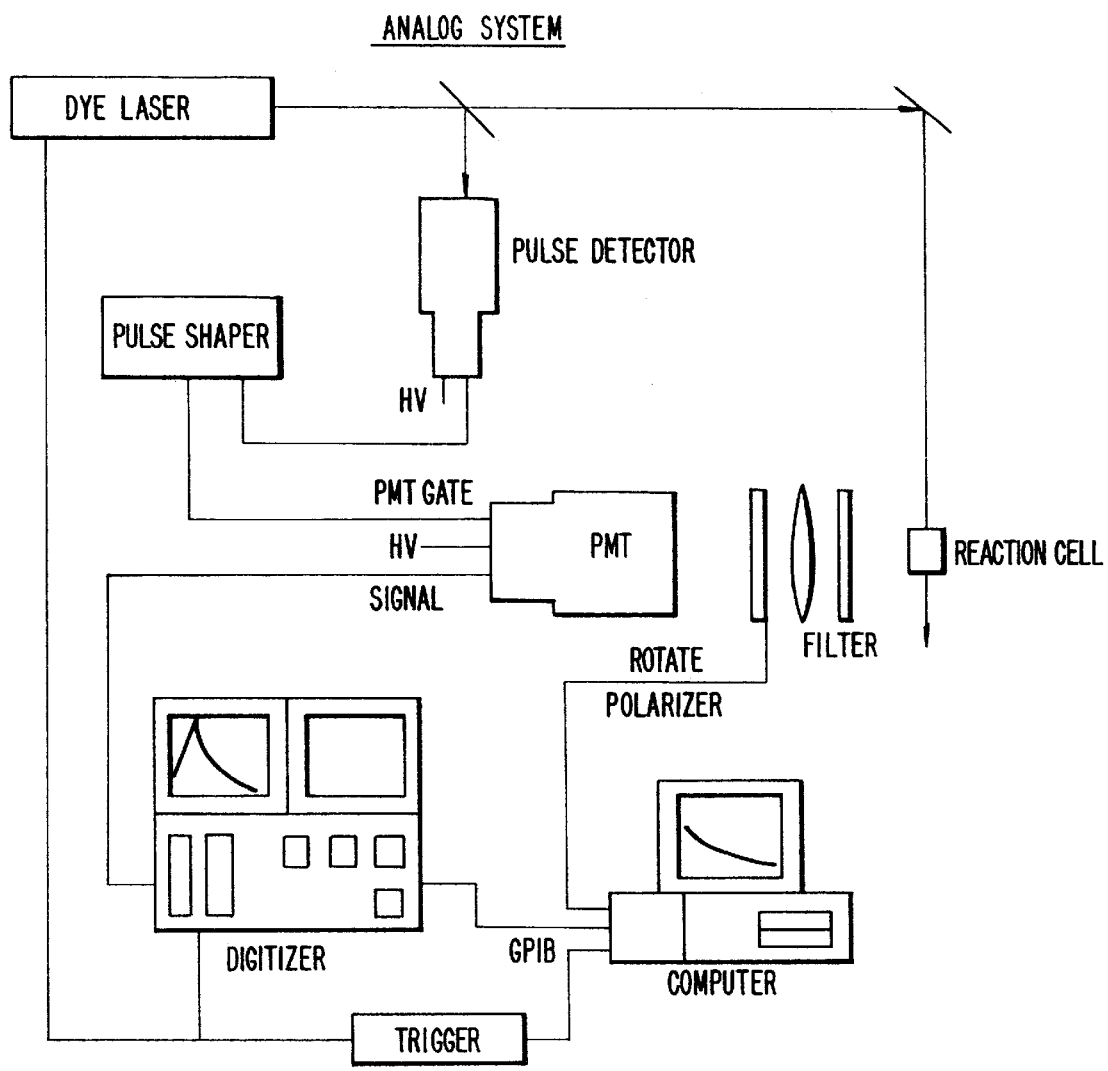
FIG. 3 describes the Diatron Analog System.

The Diatron Analog System is diagramed in FIG. 3. The tunable dye laser used was a PTI model PL2300 nitrogen laser with a dye laser module. By changing the laser dye and adjusting the dye laser grating, 600 picosecond pulses with peak power of near 40 KWatts could be generated at wavelengths from 340 to 900 nm.

A beam splitter was used to send a portion of each pulse to a pulse detector which consists of a high speed Hamamatsu photo diode. The resulting output of the photodiode was fed into a pulse shaper which converted the resulting 800 picosecond (ps) pulse into a 100 nanosecond (ns) pulse. This 100 ns pulse was then used as a gate for the Hamamatsu microchannel plate PMT whose gain was changed by 10,000 within a 2 ns time period. The PMT stayed at the high gain until the 100 ns was over.

The dye laser module, reaction cell and pulse detector was positioned and connected such that the PMT was gated to its high sensitivity state approximately 2 ns after the laser pulse passed through the reaction cell.

A filter was positioned in front of the PMT to guard against high scatter signals when required. A lens was used to image the fluorescence onto the PMT microchannel plate. Also, a rotatable polarizer was positioned in the output optical path to measure the time dependent polarization of the fluorescence.

High voltage from 1000 to 3400 volts was supplied to the PMT. The output of the PMT was connected to a Tektronix 7912AD Programmable Digitizer.

A computer was used to trigger the laser. The laser output was detected by the digitizer via a connection to the pulse detector (not shown). A programmable sweep on the digitizer set up the time spread to be measured after the laser pulse from 10 ns to as high as several seconds. Typically, the system was operated such that 512 data points were generated over a 20 ns time period.

Figure 4A:
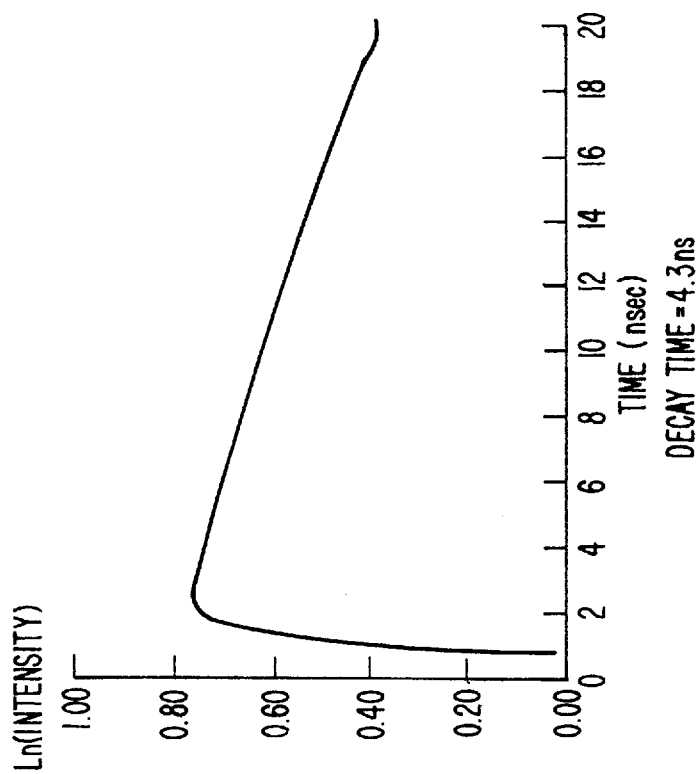
FIG. 4 depicts the decay time for caged dicarboxy silicon phthalocyanine dye.
Figure 4B:
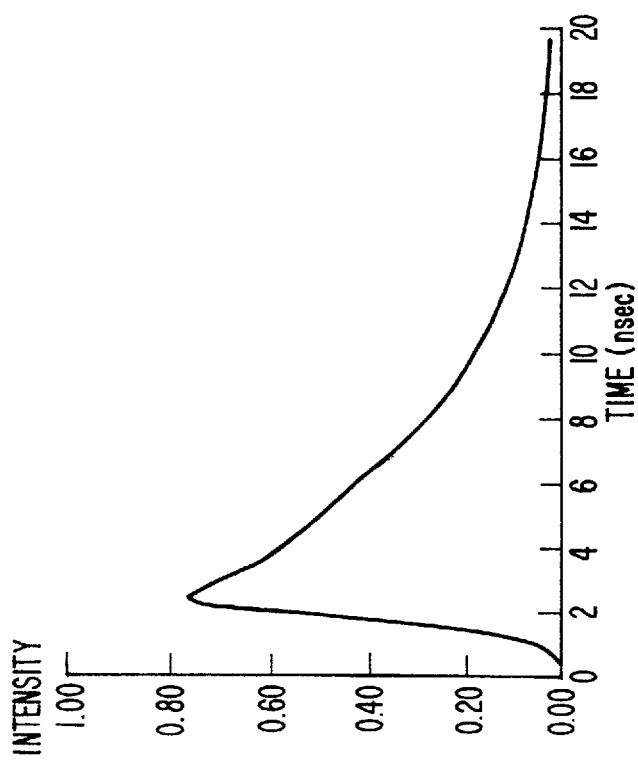

The natural log (ln) (intensity) of the dye preparations was plotted versus time and subjected to least square linear regression analysis. These data are shown in FIG. 4.

The dye preparations were analyzed for their interaction with serum protein. The dye preparations were adjusted to $5 \times 10^{-9}$ M/L in FPIA buffer. These dye preparations were added to the following solutions to a final dye concentration of $5 \times 10^{-11}$ M/L: FPIA buffer, 0.5% bovine gamma globulin, 5.0% bovine serum, 5.0% normal human serum, 5.0% pooled human serum and 5.0% whole blood lysate. These data are shown in FIG. 5. Typically, when a dye binds to a protein non-specifically (as can be seen with the "C" fraction), a significant increase in fluorescence polarization occurs. This makes it impossible to distinguish the specific polarization due to antibody binding from the non-specific due to protein-dye interaction. The "B" fraction showed only minimal interaction over buffer as determined by measurement of transient state polarization.

EXAMPLE 2

Linkers

In certain polarization assays, it is advantageous to use a spacer or linker. These linker or spacer arms are useful when different ligands are terminated by either a carboxyl or amino group. In addition, such compounds are important when the probe needs to be separated (stood off) from the molecule with the antibody binding epitope. This may be necessary to reduce the potential of non-radiated transfer of energy when antibody binds the specific epitope and/or to eliminate stearic hinderance. These linker/spacer arms are generally the same in both the ligand-probe and ligand-protein immunogen used to raise antibodies to the ligand, in order to create a specific binding pair. In polarization immunoassays, it is desirable that the spacer create a relatively inflexible linker moiety.

Because the caged dicarboxy silicon phthalocyanine is a carboxy-terminated dye, it is advantageous to have an amino terminated dye coupled to a carboxy terminated ligand. Various linkers (spacer arms) have been evaluated. Such compounds include piperazine, ethylenediamine, hexanediamine, 6-amino hexanoic acid, 5-aminobutanoic acid, 12-aminododecanoic acid, alanine and other amino acids.

The following methodology for preparation of the phthalocyanine-12 amino dodecanoic acid compounds is an example of the general reaction for such linkers: To 1.0 mg of caged phthalocyanine dye (the "B" fraction of step G of example 2) in 200 $\mu$l of 50% DMF in water was added 2 mg of 1-hydroxybenzotriazole (HOBT) and 1 mg 12-amino dodecanoic acid. The suspension was gently warmed until all ingredients were dissolved. This took from 1–2 hours. At this time 3.0 mg of 3-dimethylaminopropyl carbodiimide was added and mixed thoroughly. The reaction mixture was allowed to react overnight at 4° C. The reaction became slightly turbid and was clarified by centrifugation. The new abducts were purified on reverse phase C-18 columns by HPLC.

When 12-aminododecanoic acid was used as a linker, the polarization in glycerol of the dye increased from p=0.280 to p=0.340. Concomitantly, a 10 nm shift to 690 nm occurred, which matches commercially available 690 nm laser diodes. The change increased the dynamic range of the assay from 0.03 to greater than 0.30 millipolarization in buffer when bound to an antibody molecule. In addition, the 10 nm shift increased the signal-to-background ratio by moving away from the excitation maximum of fluorescing background molecules found in biological fluids.

Figure 6:
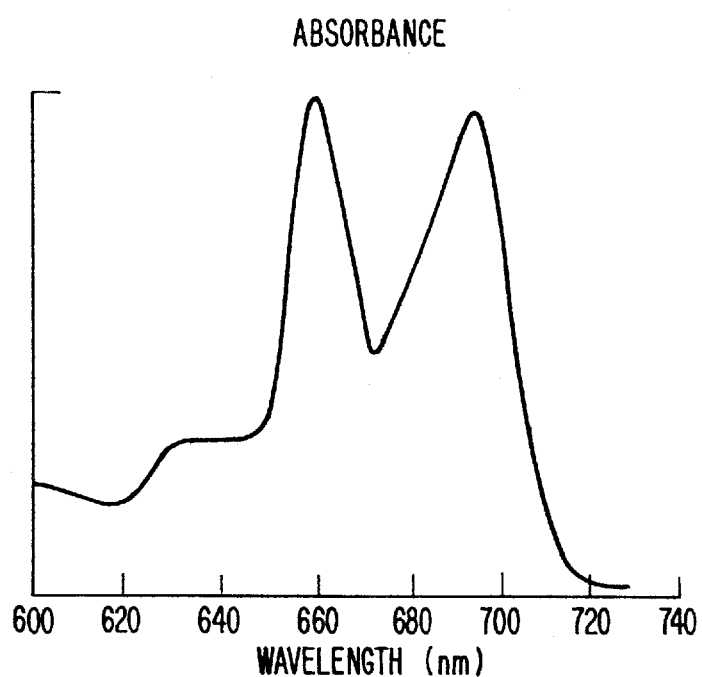
FIG. 6 depicts the absorbance spectrum of caged dicarboxy silicon phthalocyanine dye-C12 linker.
Figure 7A:
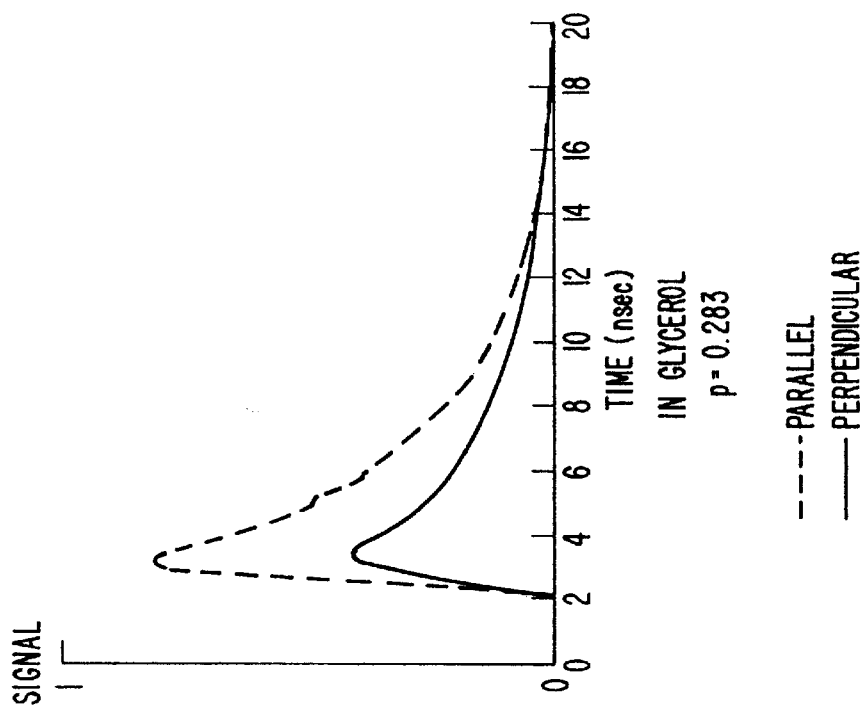
FIG. 7 depicts the polarization of caged dicarboxy silicon phthalocyanine dye-C12 linker at 680 nm.
Figure 7B:
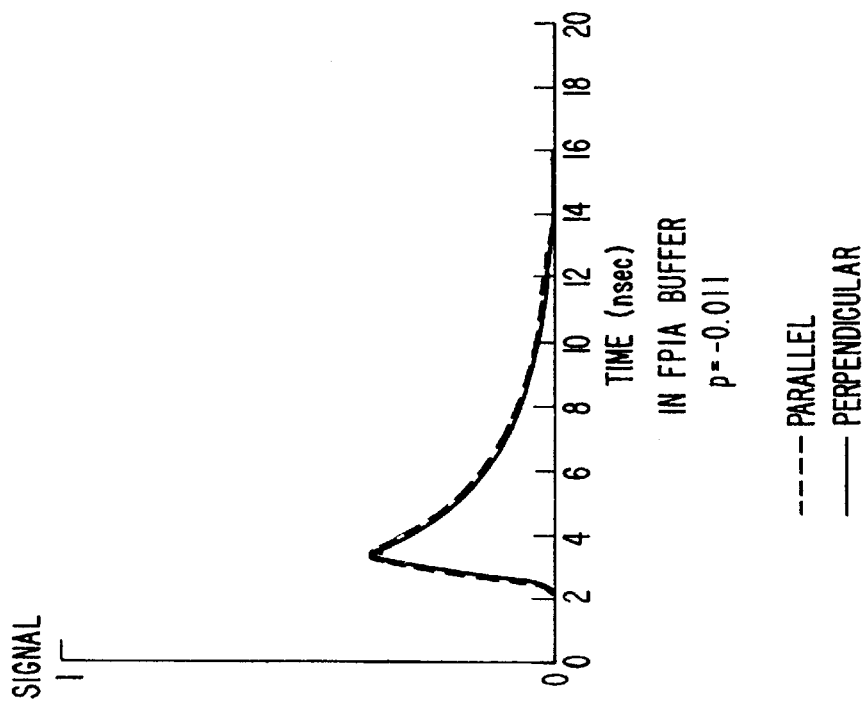
Figure 8:
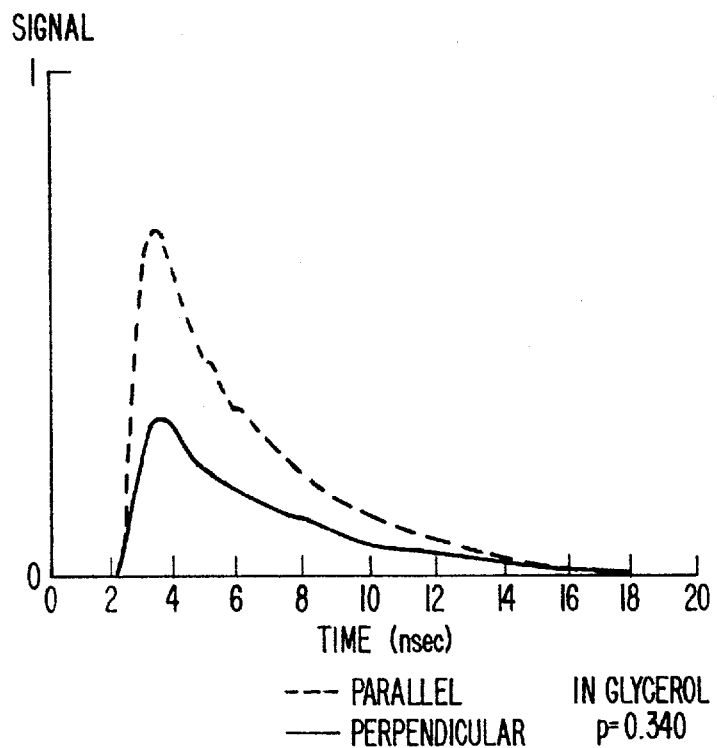
FIG. 8 depicts the polarization of caged dicarboxy silicon phthalocyanine dye-C12 linker at 690 nm.

The absorbance spectrum in methanol for the purified caged dicarboxy silicon phthalocyanine dye-linker is shown in FIG. 6. There is a 10 nm shift from 680 for the fraction "B" dye (FIG. 2), to 690 nm for the dye-linker. In addition, transient state fluorescence polarization was measured on the Diatron Analog System described in Example I, in FPIA buffer and glycerol at 680 nm and in glycerol at 690 nm. These data are shown in FIGS. 7 and 8.

III. SYNTHESIS OF CAGED DICARBOXY SILICON PHTHALOCYANINE DIGOXIN PROBE

Digoxin is a glycosylated steroid which, when cardiac output, decreases heart size, venous pressure and blood volume, and relieves edema. As noted above, digoxin has a very narrow therapeutic range (serum levels of 0.5 to 2.5 ng/ml) and is generally toxic at concentrations greater than 2.1 ng/ml. Accordingly, there is a need for a digoxin assay which can accurately and precisely determine digoxin concentrations at these levels.

EXAMPLE 3

Digoxin Probe Preparation: Caged Dicarboxy Silicon Phthalocyanine-Digoxigenin

A. Preparation of 3-Ketodigoxigenin

A mixture of 488 mg digoxigenin, 7.5 ml toluene, 3.75 ml cyclohexanone, and 550 mg aluminum isopropoxide was heated under reflux for 2.3 hours and then concentrated in vacuo to half of its original volume. Two hundred $\mu$l water was added and the mixture was evaporated in vacuo to dryness. The powdery solid was dried in vacuo over overnight. The dry residue was stirred in 25 ml methanol and the resulting mixture was filtered. The residue on the funnel was washed with 25 ml methanol. The filtrate and washing were combined and evaporated in vacuo affording 920 mg white solid.

B. Preparation of 3-Aminodigoxigenin

A mixture of 920 mg 3-ketodigoxigenin, 693 mg ammonium acetate, and 780 mg, NaBH$_2$CN was stirred in 48 ml methanol at room temperature overnight. Concentrated HCl (35 ml) in 20 ml methanol and 5 ml water were added. After gas evolution had subsided, the solvent was removed in vacuo. The residue was stirred in 15 ml water and then extracted with 2×20 ml methylene chloride. The water phase was gummy material was evaporated in vacuo and the residue was dried leaving a granular solid. This dry solid was extracted with 2×20 ml dimethylformamide (DMF) and the solution centrifuged. The clear DMF solution was evaporated in vacuo affording 684 mg white solid. The entire amount was dissolved in 25 ml methanol and the solution was stored at −20° C. overnight. A white crystalline material, which had deposited, was removed by filtration and washed with 300 µl cold methanol. The filtrate was applied to two washed EM 5766 silica TLC plates. After being developed in 90 ml chloroform+25 ml methanol the chromatogram showed 7 bands visible under 254 nm uv. Band Number 1, Rf=0.10, was removed from the plates, extracted with 4×40 ml methanol and the SiO$_2$ was centrifuged out. The supernates were combined and evaporated in vacuo affording 70 mg white solid.

C. Synthesis of Probe

The digoxin probe was prepared as follows: 4.2 mg of 3-aminodigoxigenin was placed in a 3.0 ml reaction vial and dissolved with 100 µl DMF. In a separate vial, 1.0 mg of caged dicarboxy silicon phthalocyanine (Compound IV from Example 1(G)) was dissolved in 400 ml DMF and then transferred to the reaction vial along with 200 µl of wash DMF for a total of 600 µl. 4.2 mg of 1-hydroxybenzotriazole (HOBT) was added to the reaction vial, which was then dissolved and mixed well. To make the final reaction mixture, 10.5 mg of 1-ethyl-3-(3-dimethylaminopropyl/carbodiimide)-HCl (EDAC) was added and mixed thoroughly. The reaction mixture containing digoxin-phthalocyanine probe was stored at 4.0°–8.0° C. overnight.

D. Purification of Probe

Figure 9:
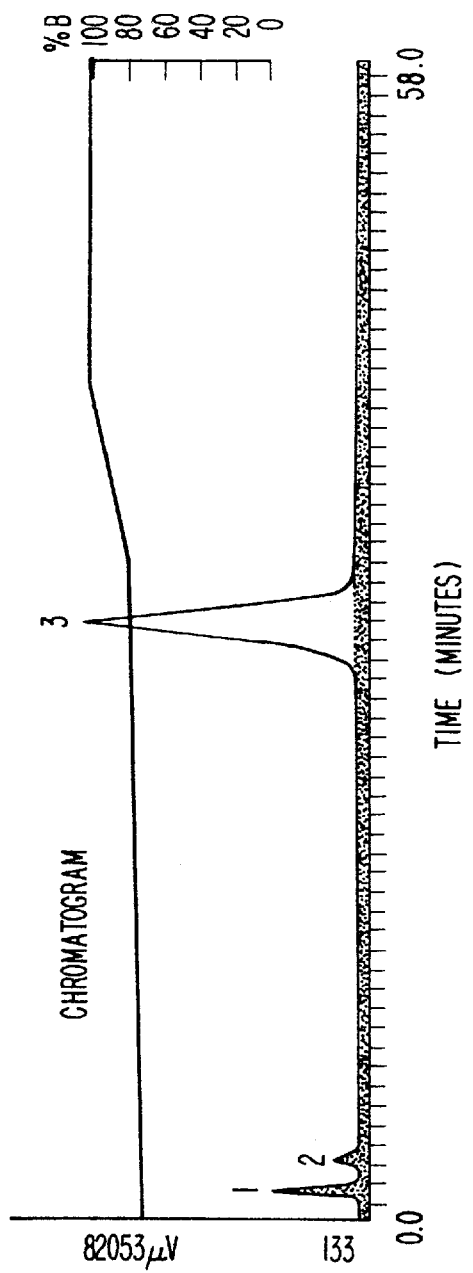
FIG. 9 depicts an HPLC Chromatograph of caged dicarboxy silicon phthalocyanine digoxin probe.

The digoxin-phthalocyanine probe was purified as follows: a slurry of 5 gm C-18 was made in acetone and poured into a 1×15 cm glass column. The acetone was removed by the application of light pressure, and the column was equilibrated by the addition of 4 column volumes of 70% methanol/30% water. The reaction mixture containing digoxin-phthalocyanine probe was applied to the column and flushed with 70% methanol/30% water. The probe was eluted with 80% methanol/20% water, concentrated by vacuum and further purified by two subsequent passes on HPLC. After the second chromatograph on HPLC, the probe was brought to dryness in vacuo. A portion was dissolved in methanol and a portion was dissolved in 100 mM NaPO$_4$ buffer containing 0.1% sodium azide and 1.0% bovine gamma globulin (pH 7.5). FIG. 9 depicts a chromatograph of the HPLC method semi-prep C-18 column with a mobile phase and gradient elution of methanol/water. FIG. 10 depicts the structure of the digoxin-phthalocyanine probe.

E. Analysis of Probe

Figure 11:
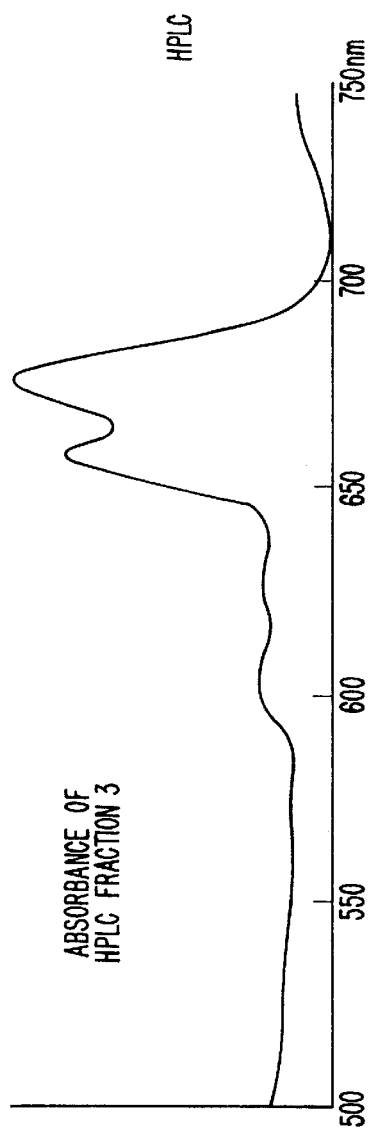
FIG. 11 shows the absorbance spectrum of caged dicarboxy silicon phthalocyanine digoxin probe in methanol.
Figure 12:
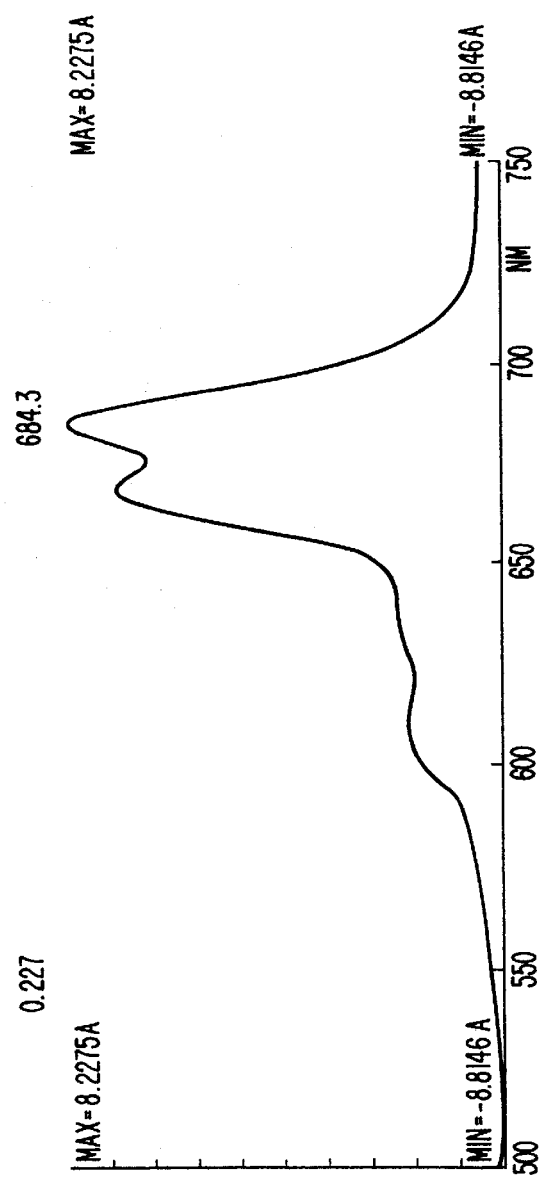
FIG. 12 shows the absorbance spectrum of caged dicarboxy silicon phthalocyanine digoxin probe in FPIA buffer.
Figure 13:
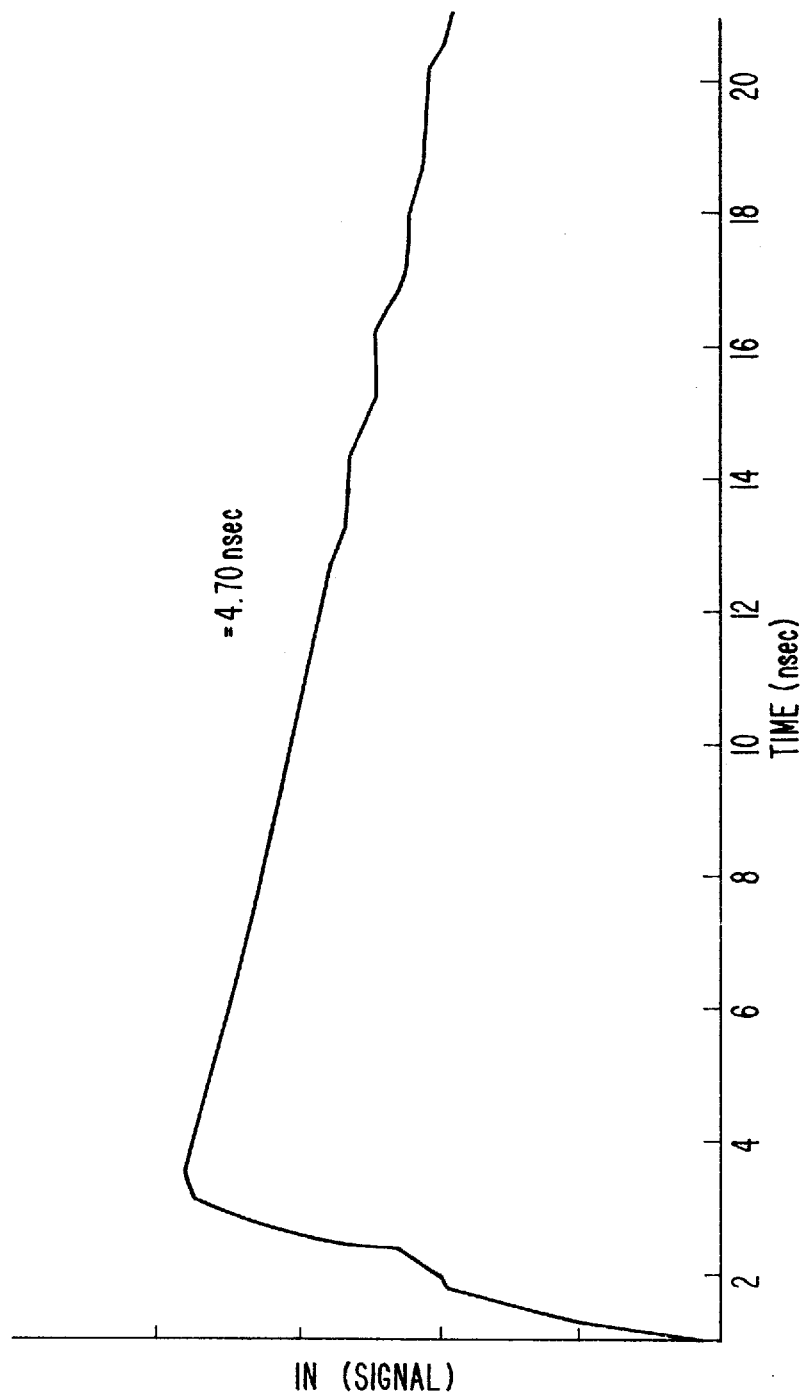
FIG. 13 shows the decay time for caged dicarboxy silicon phthalocyanine digoxin probe.

The probe was analyzed in a Perkin-Elmer spectrophotometer (Lambda 4 c) in two solvents, methanol and 100 mM phosphate, pH 7.5. FIGS. 11 and 12 are representative spectra. Fluorescence decay time was determined to be 4.7 ns using the Diatron Analog System described in Example 1 (FIG. 13).

F. Linearity in buffer and 1.0% bovine serum albumin

To determine the sensitivity and linearity of the transient state measurement system and development of a digoxin assay, it was necessary to determine the concentration of the phthalocyanine-digoxin probe. The probe was purified by one additional pass through HPLC for a total of three (3) passes through HPLC chromatography using reverse phase C18 columns. The probe was dried under vacuum and dissolved in a 100 mM phosphate buffer, pH 7.5 containing 0.01% bovine gamma globulin. The absorbance maximum was determined and the absorbance of the probe solution was measured. Concentration was determined using the following formula: A=αBC, where A=Absorbance, α=extinction coefficient, B=path length, and C=concentration. Thus, $$C = \frac{A}{\alpha B}$$

In this example: α=1.6×10$^5$, B=1 cm, and A=0.227. Accordingly, the concentration of the stock phthalocyanine-probe solution was=1.45×10$^{-6}$M/L.

Figure 14:
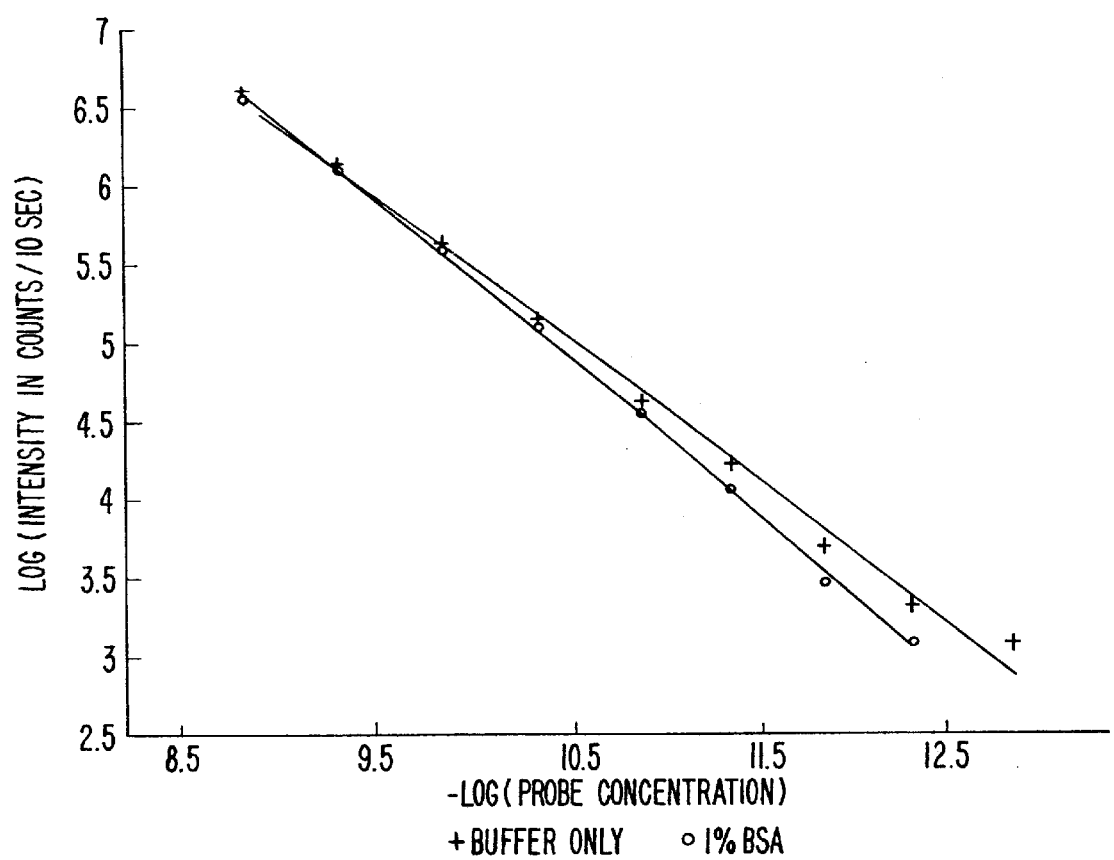
FIG. 14 shows the linearity of intensity for caged dicarboxy silicon phthalocyanine digoxin probe.

Based upon this value of 1.45×10$^{-6}$M/L, dilutions of appropriate concentrations were prepared in FPIA buffer and in 1.0% bovine serum albumin. The results are shown in FIG. 14.

The linearity of intensity of probe from 6.5×10$^{-9}$M to 1×10$^{-13}$M digoxin in both FPIA buffer and FPIA buffer with 1% BSA demonstrates the ability of the probe to function in a protein solution without interaction with binding components.

As can be seen from the data presented in Table 1, the polarizations of free dye ("B" fraction) and free probe in various sera are similar, with the polarizations being slightly higher for the digoxin probe. This is consistent with the increase in molecular size and asymmetry of the probe. In addition, the changes observed in buffer vs the serum solutions is consistent with a change in viscosity as defined by the following equation:

$$r = \frac{3nV}{RT}$$

where: R=gas constant, T=temperature (in °K), n=solution viscosity, and V=volume of molecules.

TABLE 1

Phthalocyanine Digoxin Probe: Serum Interactions
Comparison of milli-Polarization (mP)

|  | FPIA Buffer | 0.5% Gamma Globulin | 5.0% Bovine Serum | 5.0% Normal Human Serum |
| --- | --- | --- | --- | --- |
| "B" Fraction | 8.0 | 20.0 | 22.0 | 30.0 |
| Digoxin Probe | 28.1 | 51.7 | 38.5 | 40.5 |

G. Serum Urine Interactions

Figure 15:
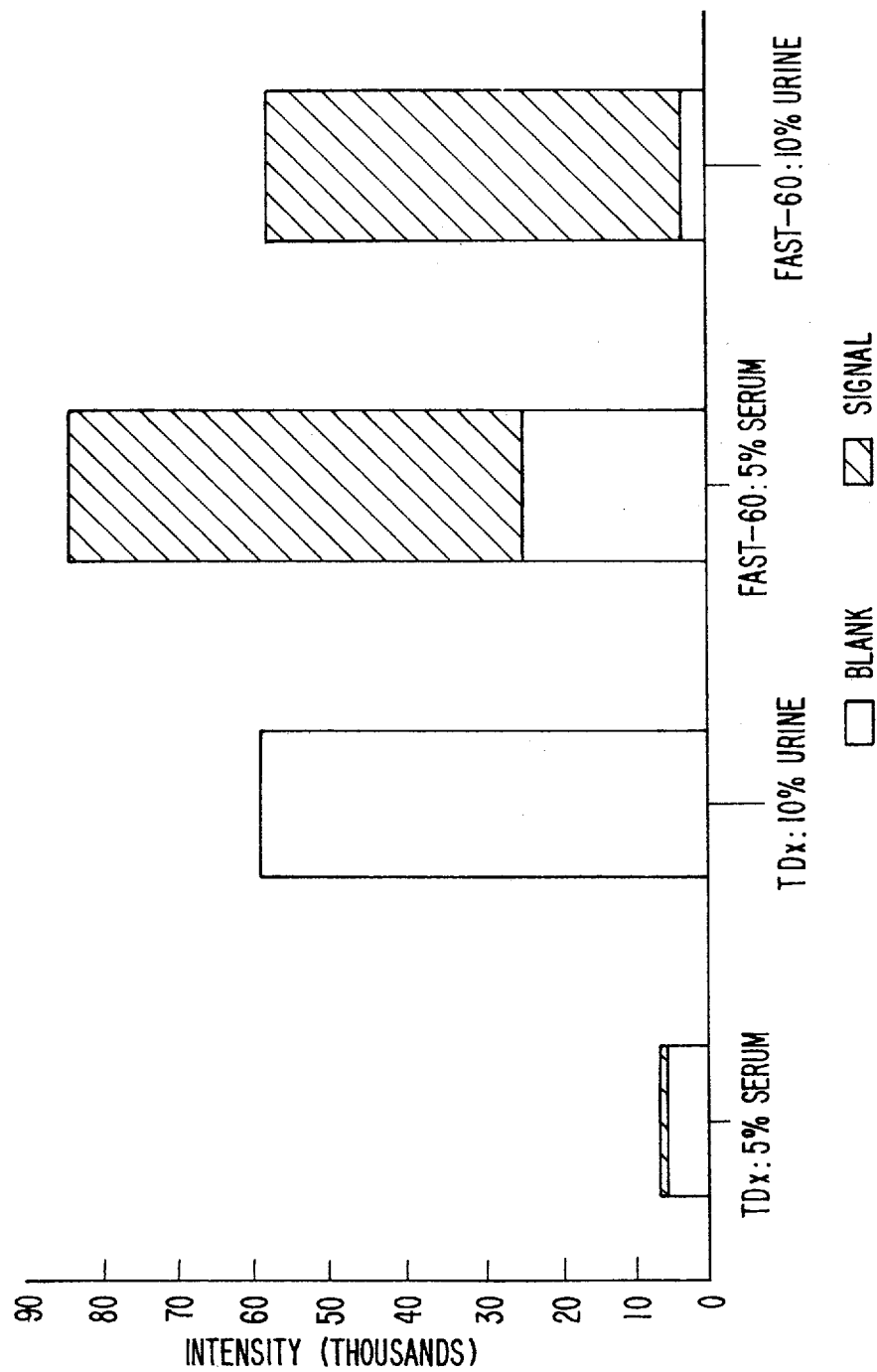
FIG. 15 shows serum/urine interactions for caged dicarboxy silicon phthalocyanine digoxin probe.

A comparison of a fluorescein-digoxin probe analyzed on the Abbott TDx® Fluorescence Polarization Analyzer and the phthalocyanine digoxin probe analyzed with the Diatron FAST-60 Analyzer is presented in FIG. 15. In this example, both probes were tested at the normal (working) concentration used when performing a digoxin assay with the TDx™ and FAST-60 analyzers (i.e., 2.5×10$^{-10}$ and 5.5×15$^{-11}$M/L). See Example 4 for a description of the Diatron FAST-60 Analyzer. In this figure, the intensity levels are plotted as background equivalents.

As can be seen from FIG. 15, the fluorescein probe is only slightly detectable above background in 5% serum and completely non-detectable in 10% urine. In contrast, the phthalocyanine digoxin probe is detectable at a very significant level above background in both the same serum and urine samples.

IV. DIGOXIN ASSAYS

EXAMPLE 4

Competitive Serum Assay For Digoxin: Sequential Binding Procedure

Digoxin reacts with serum albumin and other serum proteins at many reaction sites. Probes made with a fluorescent dye and digoxin will also react. "Nonspecific" binding or serum protein interactions were minimized in this procedure by the action of the cyclodextrin, which has an affinity for digoxin which exceeds digoxin's affinity for constituents in serum. Thus the cyclodextrin interferes with the binding of digoxin with serum constituents, but allows for binding of digoxin with digoxin antibody. Thus, the assay was designed to allow both the serum digoxin and the digoxin probe to react with the digoxin antibody.

100 $\mu$L of serum sample was mixed with 25 $\mu$L of rabbit antidigoxin and 500 $\mu$L Buffer1 (100 millimolar phosphate buffer, pH=7.6 with 0.01% bovine gamma-globulin, 0.5% gamma-cyclodextrin and 0.1% sodium azide). The mixture was incubated for 5 minutes. 25 $\mu$L of digoxin probe (as prepared according to Example 3) and 200 $\mu$L of Buffer2 (100 millimolar phosphate buffer, pH=7.6 with 0.01% bovine gamma-globulin and 0.1% sodium azide) were added and the mixture was incubated for 20 minutes.

In a study of 20 random human serum samples it was found that the serum-digoxin probe interaction would vary from sample to sample, and that the variation may be as much as 10–15 millipolarization units. The buffers in the present example were formulated to eliminate this variation to a relatively constant millipolarization of 70.

Transient state polarization was measured as described in Studholme, et al., patent application Ser. No. 071,855,238 filed Mar. 3, 1992 entitled "Fluorometer Detection System," now U.S. Pat. No. 5,323,008. The transient state optical system was installed in the Diatron "FAST-60 Analyzer," which contains a laser diode operating at 685 nm was pulsed at a 10 MHz rate. Typically, the laser "on" time was approximately 3 nanoseconds. Photons from the solution were detected using a photomultiplier tube (PMT) operating in a single photon counting mode. The photon event along with the relative time of the photon event as compared with the laser pulse time was determined. By storing the individual photon event times a histogram of frequency of photons as a function of time was generated.

The Diatron FAST-60 Analyzer includes a transient-state optical system installed in an automated fluorescence reader designed to measure fluorescence from immunoassay reactions. The reader contains the optical system, motor control for position reaction cuvettes in front of the optical system, thermal control to hold the system at 35° C. and a computer link to control the reader, analyze and display results and print those results. For immunoassay use, the results were formatted into transient-state polarization units or, by using a calibration curve, the results were transformed into concentration units of the analyte being measured.

Commercial serum calibrators for digoxin determination (obtained from Abbott Laboratories) were analyzed to obtain a standard curve. Sample blanks were prepared for each sample or calibrator by performing the same steps with the exception that buffer was added in place of the digoxin probe. The sample blank was measured and subtracted from the measurements for all reaction mixtures. The procedures were performed at 35° C.

Figure 16:
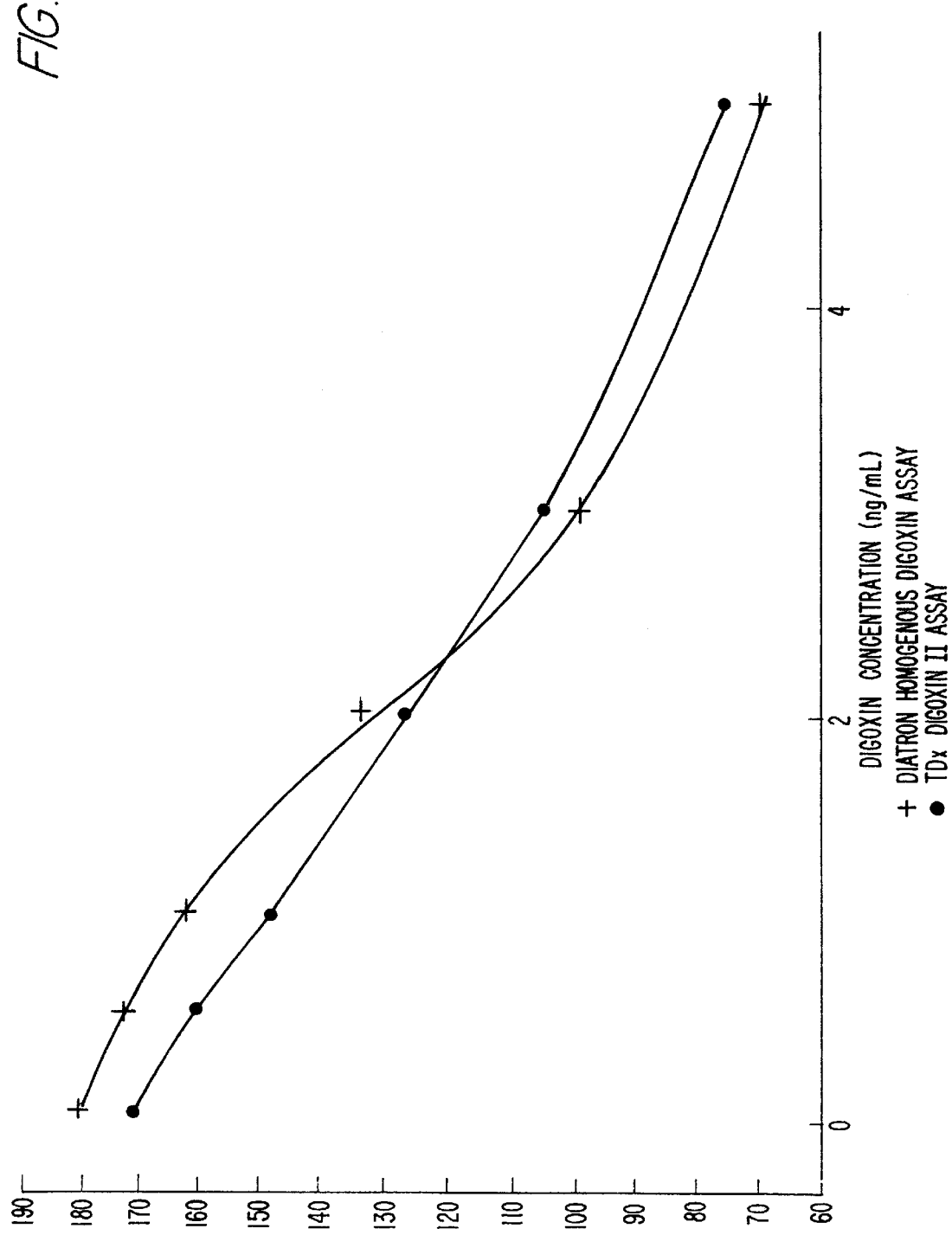
FIG. 16 depicts a comparison of TDx® and FAST-60 calibration curves.
Figure 17:
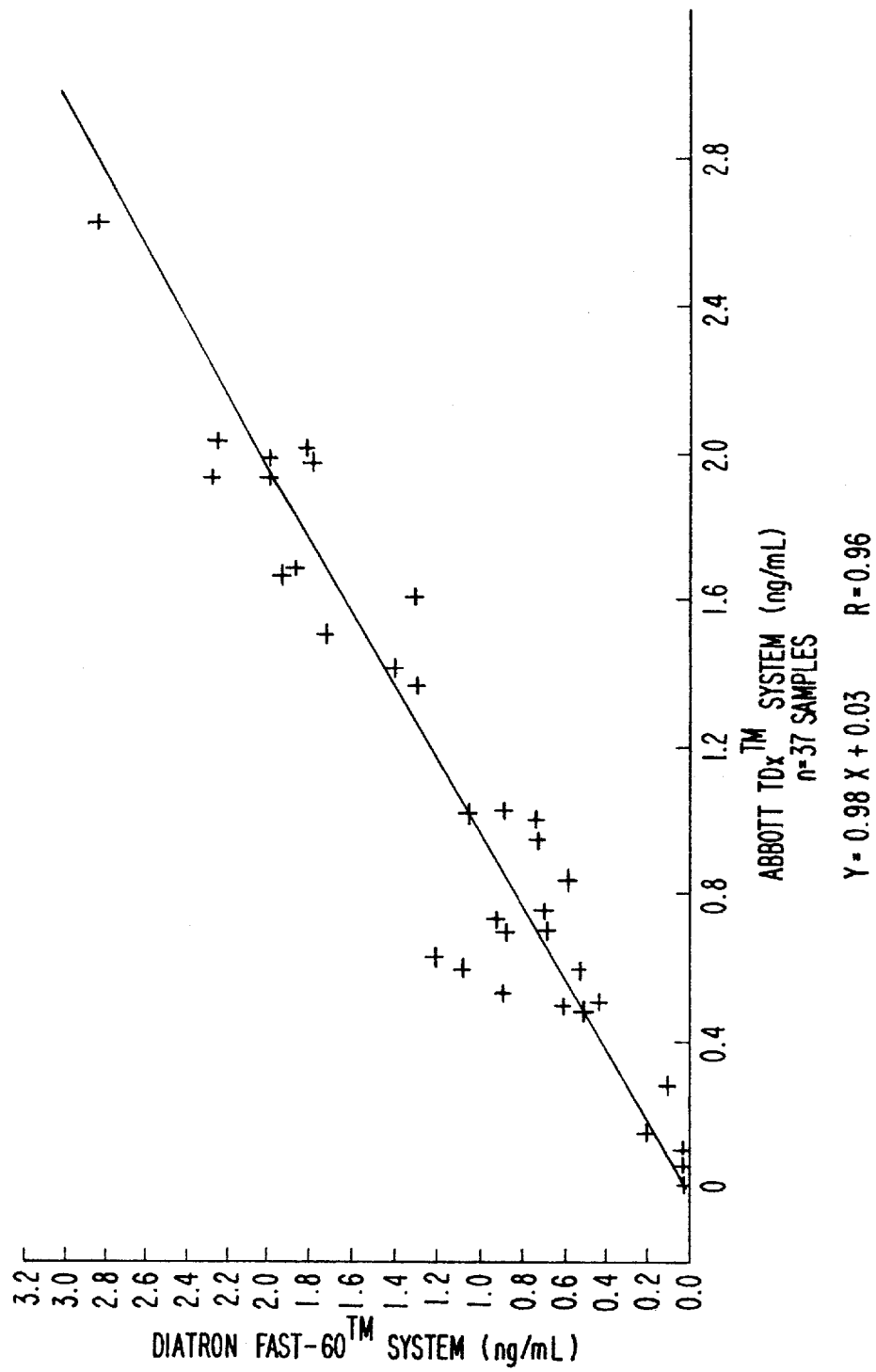
FIG. 17 depicts the correlation of digoxin samples assayed by TDx® and FAST-60.

FIG. 16 shows a comparison of digoxin calibration curves by a standard fluorescence polarization procedure (Abbott's TDx® Fluorescence Polarization Analyzer) and the homogeneous sequential binding assay procedure described in this Example. FIG. 17 displays a correlation plot of 37 serum samples assayed by a commercial digoxin test system manufactured by Abbott Laboratories (TDx® Digoxin II In Vitro Test, Product #9511-60) and assayed by the digoxin assay procedure described in this example. A correlation of 0.96 and a slope of 0.98 were determined. The slope and y-intercept indicate no systematic bias.

EXAMPLE 5

Competitive Serum Assay For Digoxin: Dilution Jump Procedure

The dilution jump procedure described in this Example allows the assay to be performed in the presence of high concentrations of serum, and was designed to reduce "nonspecific" interactions which compete with the antibody for binding to the digoxin and digoxin probe. While not wishing to be bound by any particular theory, applicants believe that when sample, antibody and digoxin probe are incubated in a small reaction volume, the "nonspecific" interactions initially compete with the antibody for binding to digoxin and digoxin probe. When the solution is diluted, the "nonspecific" protein interactions tend to disappear rapidly and only the specific antibody reaction remains.

To perform the dilution jump procedure, 200 $\mu$L of serum calibrator (Abbott Laboratories) or serum sample was mixed with 250 $\mu$L of antibody (rabbit anti-digoxin antibody), 250 $\mu$L of digoxin probe and 1000 $\mu$L FPIA buffer. The mixture was incubated for 30 minutes at 35° C. A variable volume of the reaction mixture was removed and added to 900 $\mu$L of FPIA buffer. For example 170 $\mu$L of reacted mixture in 900 $\mu$L of buffer provided a final probe concentration of $5 \times 10^{-11}$M.

Figure 18:
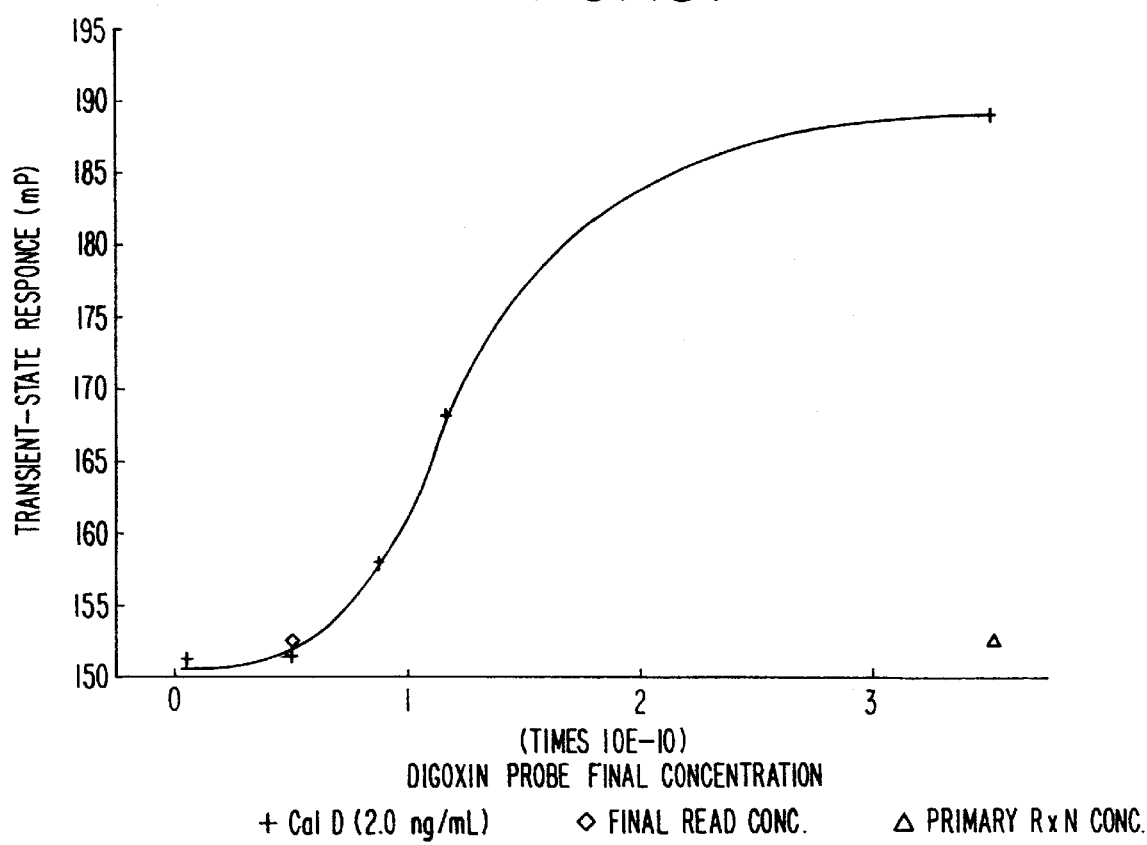
FIG. 18 depicts the effect of dilution jump on non-specific binding.

As the reaction mixture was diluted, the degree of non-specific binding decreased while the amount of specifically bound probe remained nearly constant. As shown by the results depicted graphically in FIG. 18, for non-diluted reaction mixture (probe concentration of $3.5 \times 10^{-10}$M), the resulting polarization was 189 mP. As the reaction mixture was diluted, the polarization decreased until it reached a limit (near 152 mP) at a 7-fold dilution of the reaction mixture.

An alternate dilution jump procedure was also done in which 20 $\mu$l of commercial serum calibrator or serum sample was mixed with 80 $\mu$l of lysing/buffer ($5 \times 10^{-5}$M/L stearyl-lysolecithin in 0.001M/L Tris HCl buffer at pH 8) diluent, and 10 $\mu$l of rabbit anti-digoxin was added and mixed. This mixture was allowed to incubate at 35° C. for 5 minutes. At this time, 25 $\mu$l of digoxin probe was added and incubated an additional 15 minutes. To this reaction mixture 1.0 ml of FPIA buffer was added (dilution jump), vortexed and the transient state polarization measurements were made in the Diatron FAST-60 Analyzer described in Example 4.

Figure 19:
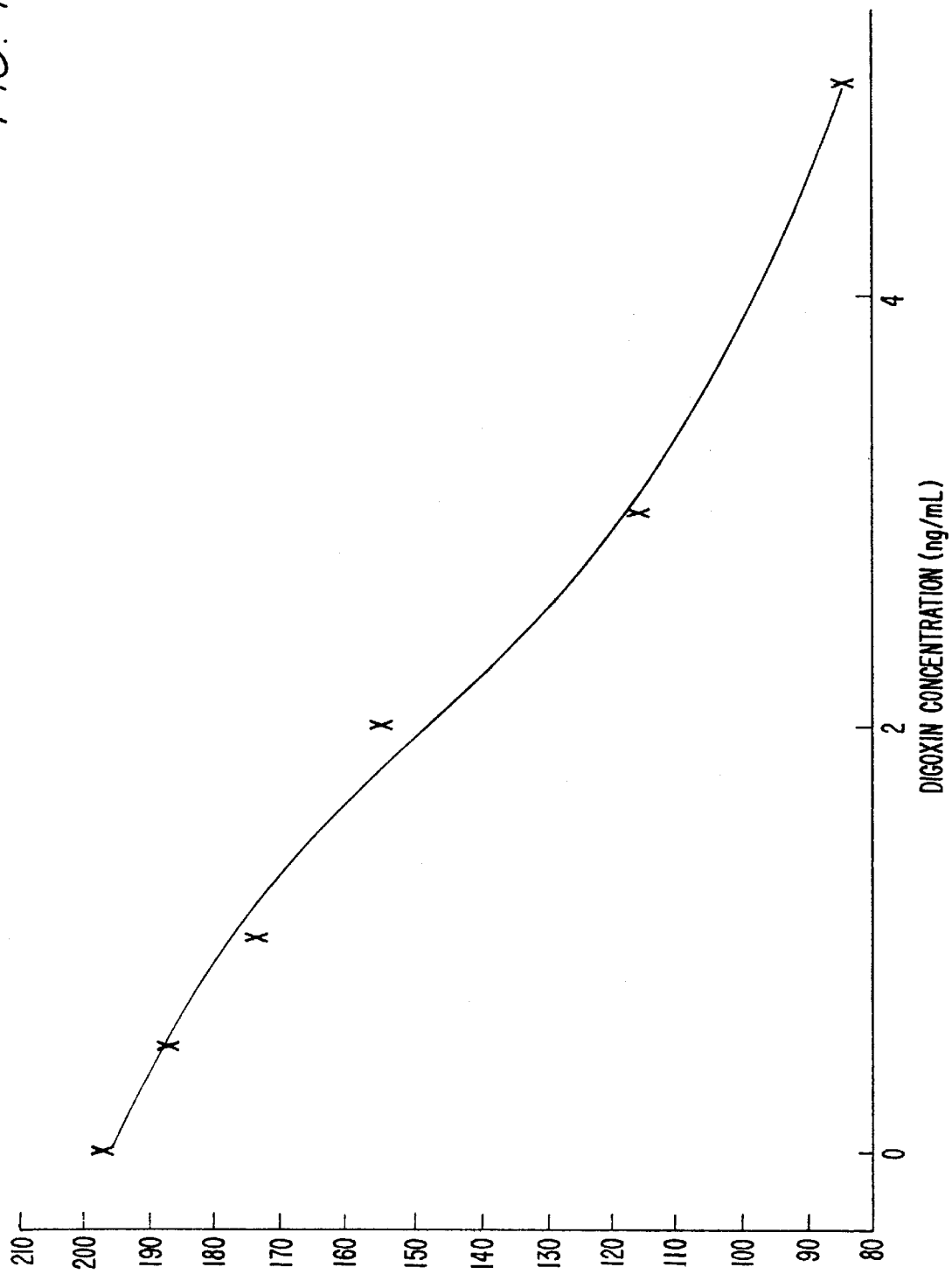
FIG. 19 depicts a digoxin probe-serum calibration curve.

The calibration curve using the dilution jump procedure is shown in FIG. 19.

EXAMPLE 6

Competitive Serum Assay For Digoxin: Signal-to-Background Comparisons for Transient-State and Steady-State Measurements The signal-to-background ratios for steady state and transient state measurement were determined as follows:

1. The steady state fluorescence intensity measurements were made on the Abbott TDx® Fluorescence Polarization Analyzer using the "Photo Check Mode." Both background and fluor measurements were taken by removing the reference solutions from the calibration carousel and substituting varying dilution of fluorescein from $1.7 \times 10^{-8}$M/L to $1.7 \times 10^{-12}$M/L in 1.0% bovine serum albumin.
2. The steady state fluorescence of the caged silicon phthalocyanine-digoxin probe was measured in a modified TDx® Fluorescence Polarization Analyzer. These modifications were made by replacement of the input filter with a 680, 10 mm ½ bandwidth filter and the output with a RG715 color glass filter. The concentrations of the probe solutions were determined in a similar manner as those determined in Example 3. Dilutions were prepared in 1.0% bovine serum albumin in concentrations of $1.4 \times 10-8$M/L to $1.4 \times 10^{-12}$M/L. The measurements were made as in 1 above.
3. The transient state measurements were made in the Diatron FAST-60 System using the same solutions as in 2 above, but at concentration of $1.4 \times 10^{-9}$M/L to $1.4 \ 10^{-14}$M/L.

The data are summarized in Table 2. The signal-to-background data is represented as a ratio (signal counts/ background count).

TABLE 2

Signal-to-Background Ratio Comparisons

| 680 nm Fluorophore | Probe Intensity (counts/15 sec) | Serum Calibrator Blank Intensity (counts/15 sec) | Probe/ Blank |
|---|---|---|---|
| Steady-State | 437,22 | 466,848 | 6.5 |
| Transient-State | 264,404 | 4,048 | 65.3 |

Thus, applicants have shown that steady state assays can be configured with acceptable signal-to-background ratios using the caged dicarboxy silicon phthalocyanine digoxin probe which is measured at 680 nm. There was an approximately 10-fold enhancement in this ratio when transient state techniques were used to time-discriminate against fast fluorescers within the background and scattering bands.

In immunoassays which measure analytes at very low concentrations, for example, digoxin at $5 \times 10^{-10}$ to $60 \times 10^{-10}$M/L, the concentration of fluorescent probe in the fluorescein steady assay system is $2.5 \times 10^{-10}$M/L. These assays require an extraction step to remove the digoxin bound to serum proteins (approximately 25–40%) and fluorescers bound to proteins that interfere in the measurement of fluorescence polarization. In serum, the background fluorescence is highly polarized due to this protein binding, which can mimic specific polarization due to antibody binding. These must be removed before the assay can be performed. Many of these fluorescers are excited by 493 nm light, which corresponds to the excitation maximum of these fluorescein based assay systems. In this example, the signal to background is at best 2.5:1. However, when unextracted serum is added as in a homogeneous assay using the fluorescein steady state measurement technique, the probe fluorescence is not detectable at the concentration of serum needed to run the assay (FIG. 15).

This principle can be illustrated by the data in Table 3. For a steady state fluorescein-based assay, the fluorophore concentration at which fluorophore signal equals background is $1.6 \times 10^{-9}$M/L. This is far above the concentration of fluorophore needed to perform an acceptable digoxin assay, i.e., an assay which can detect and quantitate digoxin at therapeutic levels. In other words, the fluor cannot be measured over fluorescence of background.

As can be seen from the data in Tables 2 and 3, there is approximately an 8-fold improvement in steady state caged dicarboxy silicon phthalocyanine measurement over steady state fluorescein measurement. This improvement increases an additional 10-fold when transient state measurements are made using the caged dicarboxy silicon phthalocyanine probe. Additionally, there is a clear 100-fold improvement of the transient state measurements over the currently used fluorescein steady state measurements.

TABLE 3

Signal-to-Background Comparison:
Fluorophore Concentration Where
Fluorophore Signal Equals Background

| Technology | Fluorophore Concentration |
|---|---|
| Steady State Fluorescein | $1.6 \times 10^{-9}$ M/L |
| Steady State Phthalocyanine Probe | $2.4 \times 10^{-10}$ M/L |
| Transient State Phthalocyanine Probe | $1.4 \times 10^{-11}$ M/L |

EXAMPLE 7

Competitive Serum Assay For Digoxin: High Sensitivity Assay

In this assay, the sensitivity of the digoxin assay described in Example 5 is increased by a factor of 10. The concentration of caged dicarboxy silicon phthalocyanine digoxin probe was determined by the procedure outlined in Example 3 to be $4.2 \times 10^{-12}$M/L. In this assay the total reaction volume was reduced by 50 percent and all reactants were reduced 10-fold. To increase the polarization values, the incubation times were increased to 5 and 15 minutes for the sequential addition, competitive binding format.

The procedure is as follows: 50 $\mu$l of lysing/buffer (see Example 5 above) diluent was mixed with 2.0 $\mu$l serum calibrator or serum, plasma or whole blood sample and 5.0 $\mu$l of rabbit anti-digoxin antibody. This mixture was incubated for 5 minutes and 2.5 $\mu$l of digoxin probe was added and incubated an additional 15 minutes. After this incubation, 1.0 ml FPIA buffer was added as a dilution jump. The transient state polarization measurements were made on the Diatron FAST-60 Analyzer described in Example 4.

Sample blanks were prepared for each sample or calibrator by performing the same steps, with the exception that buffer was added in place of the probe. The sample blank was then measured and subtracted from the measurements for the entire reaction mixtures.

Figure 20:
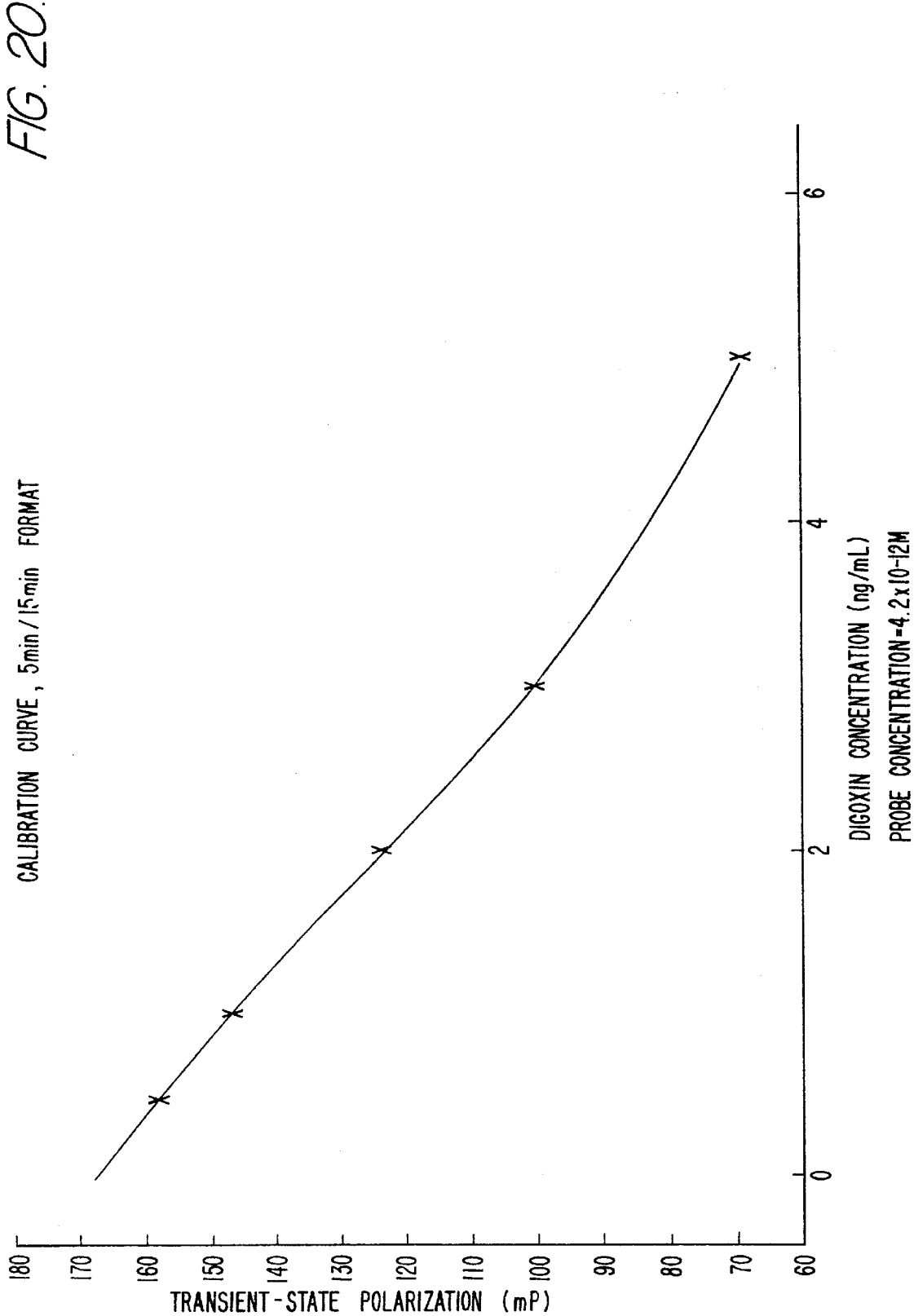
FIG. 20 depicts a calibration curve for a high sensitivity digoxin assay.

FIG. 20 displays a calibration curve for commercial serum calibrators containing known concentration of digoxin, which were assayed using the high sensitivity procedure.

EXAMPLE 8

Preparation of Whole Blood Calibrators

Whole blood was obtained from two donors by drawing blood into Vacutainer™ (Bector Dickinson) tubes containing EDTA anticoagulant. The tubes were mixed thoroughly on a standard laboratory sample rotator. Based on the average specific gravity of blood being 1.056, a series of six 2 ml volumes of whole blood were weighed using standard gravimetric technique. These samples were then spiked using a USP grade digoxin (200 ng/ml) to final concentrations of 0, 0.5, 1.0, 2.0, 3.0, and 5.0 ng/ml whole blood. The whole blood calibrators were stored at 4.0°–8.0 ° C. and were used within two weeks.

EXAMPLE 9

Whole Blood Digoxin Assay: Signal-to-Background Ratio, Serum Versus Whole Blood

Applicants determined the signal-to-background ratio of the whole blood preparations which were prepared as described in Example 8 and compared the whole blood (i.e., blank) intensity to the probe intensity. The resulting values comparing the whole blood and serum signal-to-background ratios are shown in Table 4. These measurements were made at working digoxin probe concentration of $5 \times 10^{-11}$M/L in the transient state system. It can be seen that the net probe intensities remained constant even when the background intensities fluctuated. In a typical steady state fluorescein digoxin assay where the digoxin is extracted by precipitation of proteins, the average signal-to-noise ratio is 2 to 1 at probe concentrations of $2.5 \times 10^{-10}$M/L, as contrasted with those found by homogeneous transient state fluorescence for serum and whole blood of 77.6:1 and 26.7:1, respectively.

TABLE 4

Signal-to-Background Ratio Comparisons
For Serum and Whole Blood

|  | Probe Intensity (counts/15 sec) | Blank Intensity (counts/15 sec) | Probe/Blank |
| --- | --- | --- | --- |
| Serum | 113,284 | 1,466 | 77.6 |
| Whole Blood | 100,258 | 3,757 | 26.7 |

EXAMPLE 10

Homogeneous Whole Blood Digoxin Assay— Clinical Study

Previous whole blood immunoassays have been limited by many factors. For example, separation steps are required in many assay systems, enzymes and other substances released from red blood cells cause interference in the assays, and the instrumentation is incapable of measuring analytes or reaction products through whole blood hemolysates. Applicants have developed a homogeneous whole blood assay system which offers the clinical laboratory and other testing facilities significant advantages over currently used methods, including decreased labor cost, and decreased sample manipulation. In addition, with a homogeneous 5 to 10 minute assay, the procedure can be brought much closer to the patient, for example, to the bedside, emergency care facilities clinics and satellite testing facilities.

Digoxin is widely distributed in body tissues. Serum and plasma have been the accepted samples for the assay of digoxin using the current commercially available test kits. Studies have shown a relative constant relationship between heart muscle and serum digoxin levels, thus validating the use of digoxin serum levels in monitoring patients receiving the drug (Doherty, J. E., et al., 1978, "Clinical Pharmacokinetics of Digitalis Glycosides." Progress in Cardiovascular Diseases, Vol. XXI, No. 2 (Sept./Oct.)). Because whole blood has not been routinely used as a medium for assay in digoxin therapy, the following study was undertaken to determine: (1) the distribution of digoxin in serum, plasma and red cell components of blood; (2) the percentage discrepancy, if any, in digoxin levels of serum, plasma and whole blood assays; and (3) correlation among two currently commercially available assays—the Abbott TDx® serum assay and the Dade Stratus® serum assay—and the assay of the present invention. The clinical study was conducted using 43 patient samples, collecting 1 EDTA tube for whole blood or plasma levels and 1 tube for serum levels. Each sample pair was analyzed for serum digoxin levels determined by the Abbott TDx®, Dade Stratus® and Diatron FAST-60 Systems. Plasma levels were analyzed by Abbott TDx® and Diatron FAST-60 Systems. Whole blood levels were analyzed by Abbott TDx® and Diatron FAST-60 Systems. The Abbott TDx® System used the TDx® Digoxin II In Vitro Test, Product #9511-60 (Abbott Laboratories). The Dade Stratus System used the Dade Stratus® Digoxin Fluorometric Enzyme Immunoassay (Dade Diagnostics Division of Baxter Healthcare Division, Miami, Fla.). The Diatron FAST-60 System used the methods described in Example 5 and the apparatus described in Example 4 and Studholme, et al., application Ser. No 07/855,238 now U.S. Pat. No. 5,323,008.

In this study, the primary concern was whether the whole blood digoxin values were similar to the serum values. Thus, to reduce the number of variables, the whole blood lysates were clarified by centrifugation before assay.

The study subjects were randomly selected patients currently on active digoxin therapy. The following samples were taken from each patient: (1) Red stopper Vacutainer™ tube (no EDTA) for serum collection (a minimum of 2 ml required); and (2) Purple stopper Vacutainer™ tube (EDTA) for whole blood assay and for plasma preparation (a minimum of 4 ml required). Both tubes drawn at the same time. All blood, serum and plasma was stored at 4° C. until assayed. All assays run within 24 hours after drawing. The Diatron FAST-60 Digoxin Assay System consisted of (1) caged dicarboxy silicon phthalocyanine digoxin probe in FPIA buffer with 1% bovine gamma globulin; (2) rabbit anti-digoxin in FPIA buffer with 0.1% bovine gamma globulin; (3) lysing/buffer diluent; and (4) FPIA buffer (100 mM phosphate buffer with 1% sodium azide and 0.01% bovine gamma globulin).

Figure 21:
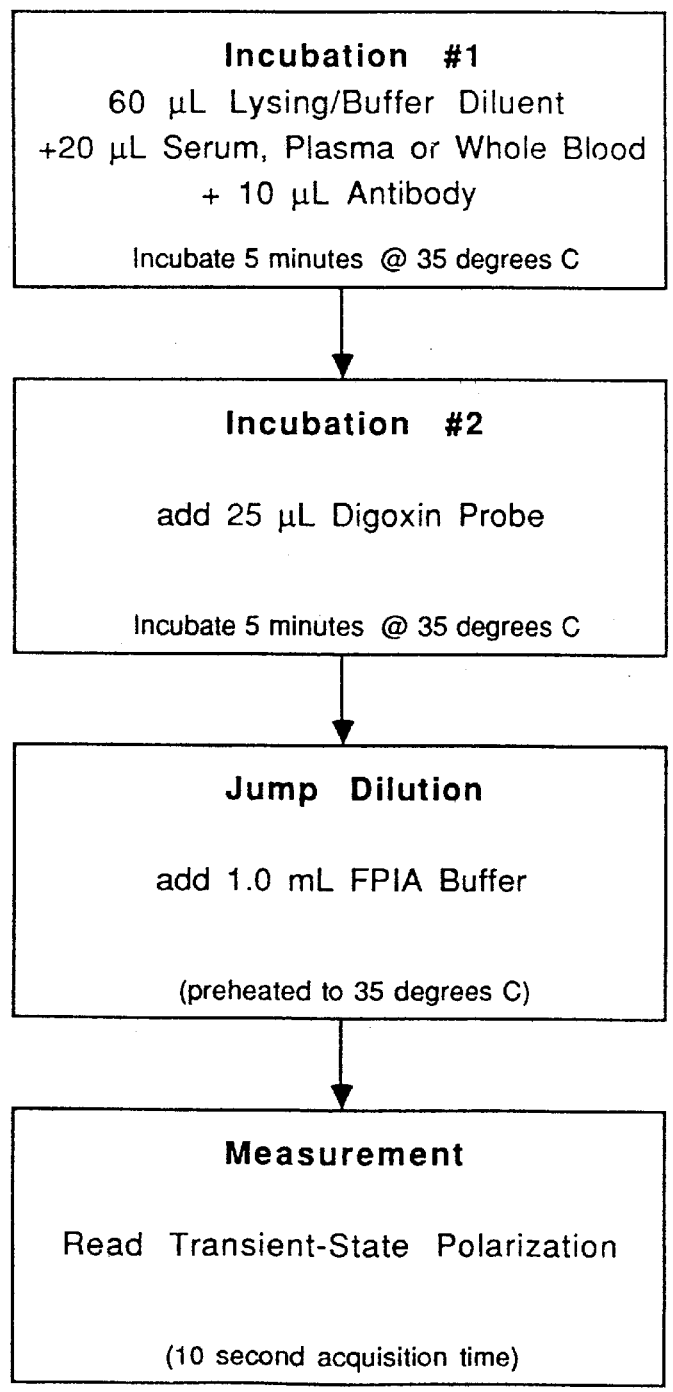
FIG. 21 describes the FAST-60 digoxin assay procedure.

Assay procedures were performed as follows:
1. Serum
   A. Abbott TDx® Digoxin II In Vitro Test—Performed according to manufacturer's instructions.
   B. Dade Stratus®—Performed according to manufacturer's instructions. Serum values performed by Pathology Medical Laboratories, 11180 Roselle Street, San Diego, Calif. 92121.
   C. Diatron FAST-60—See FIG. 21.
2. Plasma
   A. Abbott TDx® Digoxin II In Vitro Test—Performed according to manufacturer's instructions.
   B. Diatron FAST-60—See FIG. 21.
3. Whole Blood
   A. Abbott TDx® Digoxin II In Vitro Test— Performed according to manufacturer's instructions, except for the precipitation step. Digoxin extraction from whole blood was accomplished as follows: to 360 μl whole blood, an equal volume of Abbott Precipitation Reagent (Digoxin II) was added with immediate vortexing for 30 seconds. The conical tubes were centrifuged at 10,000 RPMs for two minutes. The slightly brownish supernate was removed very carefully with a Pasteur pipette and transferred to the sample cup, to avoid the transfer of small particles.

B. Diatron FAST-60—See FIG. 21.

Red blood cells were lysed prior to assay by addition of lysing buffer (0.001M/L Tris buffer, pH 8.0 containing $5\times10^{-5}$M/L stearyl-lysolecithin). Palmitoyl-lysolecithin and myristoyl-lysolecithin in Tris buffer are equally effective. These reagents are preferred in that they do not interfere with the immunoassay at this concentration, and that red cell ghost particle size is reduced in 30 to 60 seconds, thus reducing any effect of light scatter during the fluorescence measurements resulting in a homogeneous, non-separation whole blood assay.

The results of the testing are tabulated in Table 5. The values from the TDx® and Stratus® are the result of single point testing. Because the FAST-60 procedure used "manual pipetting" and automated instrumental analysis, the samples were run in duplicate and the raw values averaged.

Figure 25:
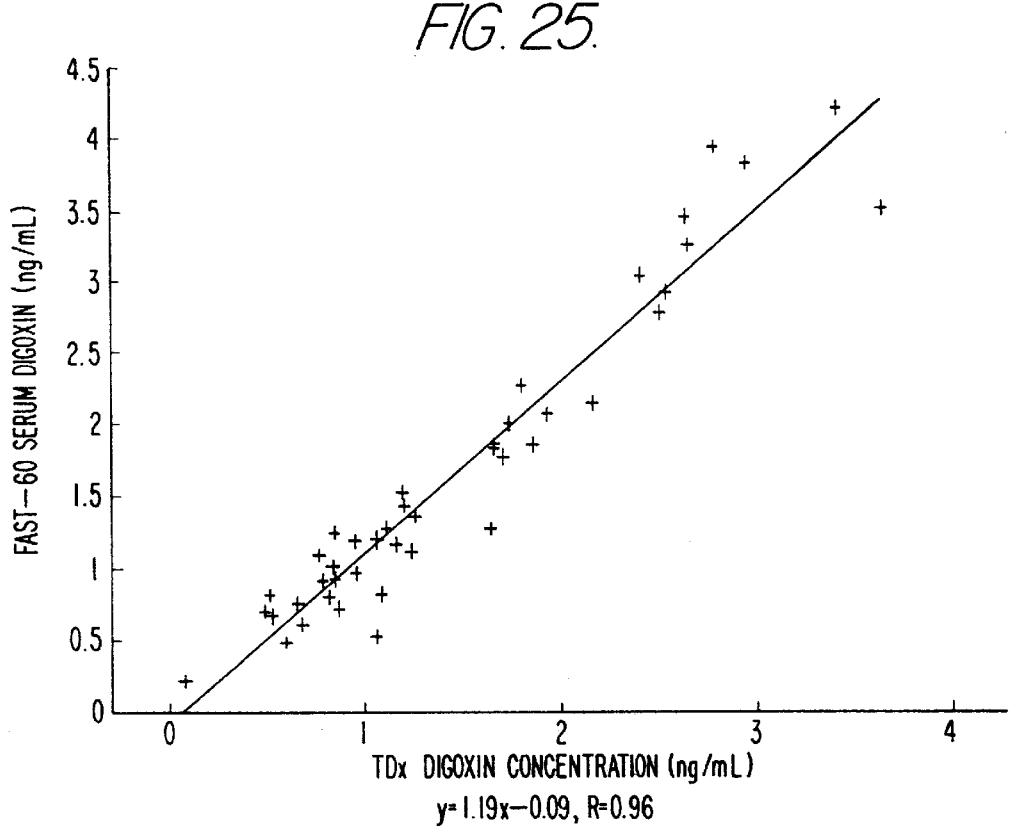
FIG. 25 depicts digoxin correlation—TDx® Serum vs. FAST-60 Serum.
Figure 26:
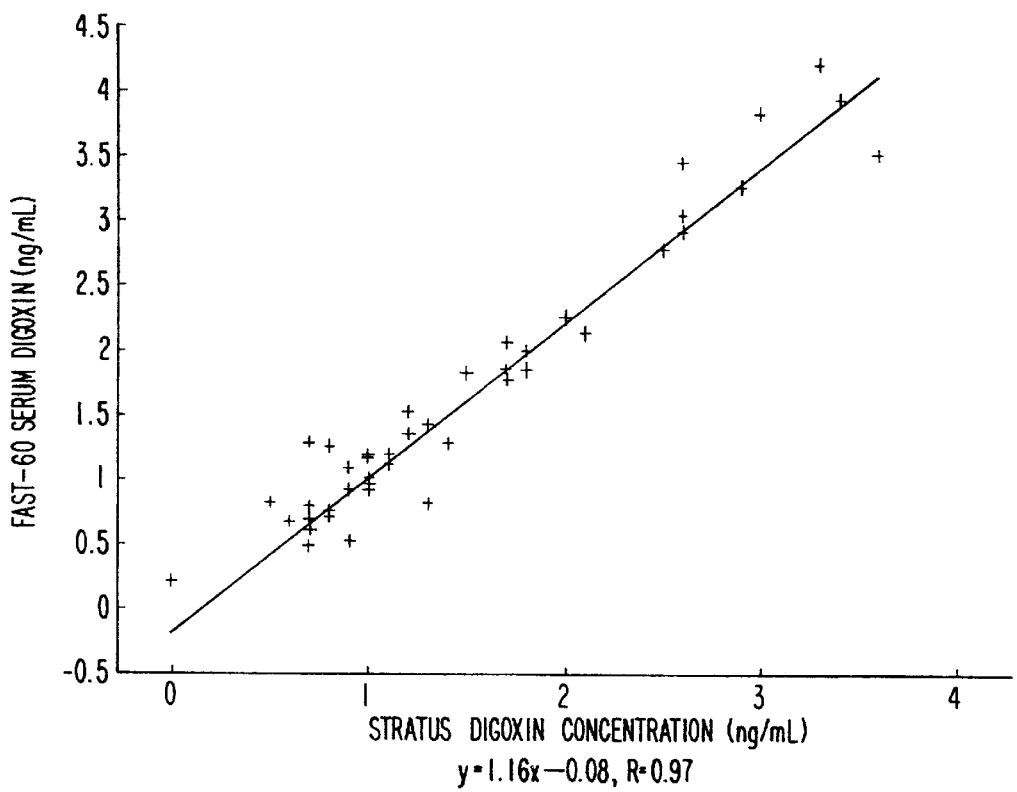
FIG. 26 depicts digoxin correlation—Stratus® Serum vs. FAST-60 Serum.

The correlation data are found in FIGS. 22 through 26. These include TDx® serum versus FAST-60 whole blood (FIG. 22), Stratus® serum versus FAST-60 whole blood (FIG. 23) FAST-60 serum versus FAST-60 whole blood (FIG. 24), TDx® serum versus FAST-60 serum (FIG. 25) and Stratus® serum versus FAST-60 serum (FIG. 26).

As can be seen in FIGS. 22 and 24, a high degree of correlation exists between TDx® serum versus FAST-60 whole blood, with R=0.96 and 0.97, respectively. When the correlation data in FIG. 24 is compared to FIG. 23, it can be seen that the data is system consistent within the FAST-60 System. FIGS. 25 and 26 show a comparison of TDx® serum versus FAST-60 serum and Stratus® serum versus FAST-60 serum assay data with correlations of R=0.96 and 0.97, respectively. Again, it could be interpreted that a slight system bias exists.

The raw digoxin values for the assays are found in Table 5. A comparison of the FAST-60 serum and FAST-60 whole blood systems with the TDx® and Stratus® Systems reveals only small differences between the mean values. This is surprising and remarkable when considering the differences inherent in the various methods used. A composite CV of 12.7% was found when comparing data for all assays.

TABLE 5

|  | Abbott TDx ng/mL Serum | Plasma | WB | Diatron FAST-60 ng/mL Serum | Plasma | WB | PML Stratus ng/mL Serum | Mean ng/mL All | % C.V All |
| --- | --- | --- | --- | --- | --- | --- | --- | --- | --- |
| 1 | 0.87 | 0.80 | 1.00 | 0.72 | 0.82 | 0.92 | 0.80 | 0.85 | 10.0 |
| 2 | 2.51 | 2.08 | 2.75 | 2.78 | 2.02 | 2.08 | 2.50 | 2.39 | 12.6 |
| 3 | 2.16 | 2.21 | 2.46 | 2.14 | 1.92 | 2.05 | 2.10 | 2.15 | 7.2 |
| 4 | 1.11 | 0.92 | 1.11 | 1.28 | 1.07 | 1.24 | 0.70 | 1.06 | 17.3 |
| 5 | 0.85 | 1.03 | 1.41 | 1.25 | 1.24 | 1.46 | 0.80 | 1.15 | 21.0 |
| 6 | 1.85 | 1.96 | 1.83 | 1.85 | 1.87 | 1.95 | 1.80 | 1.87 | 3.0 |
| 7 | 1.08 | 1.35 | 0.90 | 0.82 | 1.19 | 0.77 | 1.30 | 1.06 | 20.4 |
| 8 | 0.82 | 0.87 | 1.04 | 0.80 | 0.76 | 0.88 | 0.70 | 0.84 | 12.0 |
| 9 | 2.79 | 3.13 | 3.23 | 3.93 | 4.04 | 4.34 | 3.40 | 3.55 | 14.6 |
| 10 | 0.96 | 0.82 | 0.98 | 0.97 | 0.73 | 0.75 | 1.00 | 0.89 | 12.2 |
| 11 | 0.78 | 0.88 | 1.21 | 0.92 | 0.96 | 1.00 | 1.00 | 0.96 | 12.8 |
| 12 | 1.80 | 1.74 | 2.43 | 2.26 | 1.85 | 1.90 | 2.00 | 2.00 | 11.9 |
| 13 | 0.60 | 0.61 | 0.67 | 0.49 | 0.46 | 0.53 | 0.70 | 0.58 | 14.4 |
| 14 | 1.70 | 1.50 | 1.91 | 1.77 | 1.35 | 1.68 | 1.70 | 1.66 | 10.2 |
| 15 | 1.06 | 0.96 | 1.27 | 1.20 | 0.96 | 0.95 | 1.10 | 1.07 | 11.0 |
| 16 | 0.53 | 0.53 | 0.60 | 0.68 | 0.45 | 0.43 | 0.60 | 0.55 | 15.0 |
| 17 | 0.08 | 0.02 | 0.00 | 0.22 | 0.27 | 0.00 | 0.00 | 0.08 |  |
| 18 | 0.77 | 0.74 | 1.08 | 1.09 | 0.95 | 0.83 | 0.90 | 0.91 | 14.3 |
| 19 | 1.66 | 1.52 | 2.10 | 1.86 | 1.68 | 1.75 | 1.70 | 1.75 | 9.7 |
| 20 | 2.41 | 2.23 | 3.24 | 3.04 | 2.32 | 2.60 | 2.60 | 2.63 | 13.2 |
| 21 | 1.19 | 1.32 | 1.62 | 1.53 | 1.39 | 0.98 | 1.20 | 1.32 | 15.3 |
| 22 | 1.05 | 1.13 | 1.51 | 0.53 | 1.12 | 0.94 | 0.90 | 1.03 | 26.7 |
| 23 | 1.64 | 1.58 | 2.01 | 1.28 | 1.40 | 1.55 | 1.40 | 1.55 | 14.2 |
| 24 | 1.65 | 1.62 | 2.35 | 1.83 | 1.62 | 1.77 | 1.50 | 1.76 | 14.7 |
| 25 | 2.95 | 2.87 | 3.59 | 3.82 | 2.93 | 3.66 | 3.00 | 3.26 | 11.6 |
| 26 | 3.41 | 3.13 | 3.65 | 4.20 | 3.80 | 4.06 | 3.30 | 3.65 | 10.1 |
| 27 | 0.52 | 0.55 | 0.71 | 0.82 | 0.74 | 0.42 | 0.50 | 0.61 | 22.5 |
| 28 | 2.54 | 2.48 | 2.91 | 2.92 | 2.56 | 3.00 | 2.60 | 2.72 | 7.4 |
| 29 | 1.93 | 1.84 | 2.31 | 2.07 | 2.02 | 2.20 | 1.70 | 2.01 | 9.6 |
| 30 | 2.64 | 3.02 | 3.44 | 3.45 | 4.64 | 3.55 | 2.60 | 3.33 | 19.3 |
| 31 | 3.64 | 3.49 | 4.34 | 3.51 | 3.83 | 4.21 | 3.60 | 3.80 | 8.4 |
| 32 | 1.24 | 1.06 | 1.13 | 1.12 | 1.23 | 0.86 | 1.10 | 1.11 | 10.6 |
| 33 | 0.68 | 0.55 | 0.53 | 0.61 | 0.44 | 0.81 | 0.70 | 0.62 | 18.5 |
| 34 | 1.26 | 1.23 | 1.28 | 1.36 | 0.97 | 1.38 | 1.20 | 1.24 | 10.1 |
| 35 | 1.74 | 1.67 | 2.05 | 2.00 | 2.04 | 1.98 | 1.80 | 1.90 | 7.6 |
| 36 | 1.16 | 0.95 | 1.17 | 1.17 | 0.87 | 0.99 | 1.00 | 1.04 | 10.8 |
| 37 | 0.85 | 0.98 | 1.12 | 0.93 | 0.96 | 0.86 | 0.90 | 0.94 | 9.0 |
| 38 | 2.65 | 2.77 | 3.06 | 3.26 | 3.30 | 2.93 | 2.90 | 2.98 | 7.5 |
| 39 | 0.95 | 0.96 | 1.22 | 1.19 | 1.05 | 0.90 | 1.00 | 1.04 | 11.0 |
| 40 | 0.66 | 0.63 | 0.67 | 0.76 | 0.73 | 0.82 | 0.80 | 0.72 | 9.4 |
| 41 | 0.84 | 0.89 | 1.03 | 1.02 | 0.93 | 1.01 | 1.00 | 0.96 | 7.1 |
| 42 | 0.49 | 0.67 | 0.90 | 0.70 | 0.64 | 0.72 | 0.70 | 0.69 | 16.3 |
| 43 | 1.20 | 1.16 | 1.54 | 1.43 | 1.16 | 1.06 | 1.30 | 1.26 | 12.4 |
| Mean | 1.47 | 1.45 | 1.75 | 1.66 | 1.56 | 1.60 | 1.49 | 1.57 | 12.7 |
| % CV | 57.3 | 57.4 | 57.1 | 62.5 | 66.6 | 67.6 | 58.5 | 60.0 |  |

In addition, the digoxin values for whole blood, plasma and serum obtained on the FAST-60 system were extrapolated from a single composite calibration curve. Thus, it would appear that satisfactory digoxin values could be obtained using either specimen and extrapolation from only one calibration curve. In a clinical setting this is important in that less sample needs to be drawn from the patient, and also, any one of the blood specimen can be used in the measurement of digoxin. This saves the patient from a needless extra venipuncture and saves the laboratory time and additional cost for time and materials.

The above examples involve the preparation and use of a caged dicarboxy silicon phthalocyanine digoxin probe. Those skilled in the art will appreciate that other types of fluorescent digoxin probes which comprise a detectably labeled marker component which comprises a fluorophore moiety comprising a luminescent substantially planar molecular structure coupled to two solubilizing polyoxyhydrocarbyl moieties, one located on either side of the planar molecular structure, can be prepared. Those skilled in the art will also readily appreciate the fact that caged dicarboxy silicon phthalocyanine probes can be prepared for other analytes, as well. For example, small analytes such as amikacin, gentamicin, netilmicin, tobramycin, carbamazepine, ethosuximide, valproic acid, disopyramide, lidocaine, procainamide, quinidine, methotrexate, amitriptyline, mortripyline, imipramine, desipramine, vancomycin and cyclosporine are particularly suited for the assays described herein due to their size.

For example, as described in Examples 11–17 below, such probes were prepared for digitoxin, theophylline, phenobarbital, thyroxine, N-acetylprocainamide, primidone and phenytoin. Those skilled in the art will also recognize that caged dicarboxy silicon phthalocyanine probes can be prepared for peptides. For example, as described in Examples 18 and 19 below, such probes were prepared for rubella virus peptide.

EXAMPLE 11

Synthesis of Caged Dicarboxy Silicon Phthalocyanine-Digitoxin

A. Preparation of 3-aminodigitoxigenin 3-aminodigitoxigenin was prepared by procedures similar to those described in Example 3 above for the digoxin probe.

B. Preparation of Probe

The digitoxin probe was prepared as follows: 0.8 mg of 3-aminodigitoxigenin was placed in a 3.0 ml reaction vial and dissolved in 100 $\mu$l DMF. Caged dicarboxy silicon phthalocyanine (1.0 mg) was added to the reaction vial. Also added to the reaction vial were 0.5 mg HOBT and 2.0 mg EDAC and the resulting mixture was thoroughly mixed. The reaction mixture was stored overnight at about 4° to 8° C.

C. Purification of Probe

Figure 27:
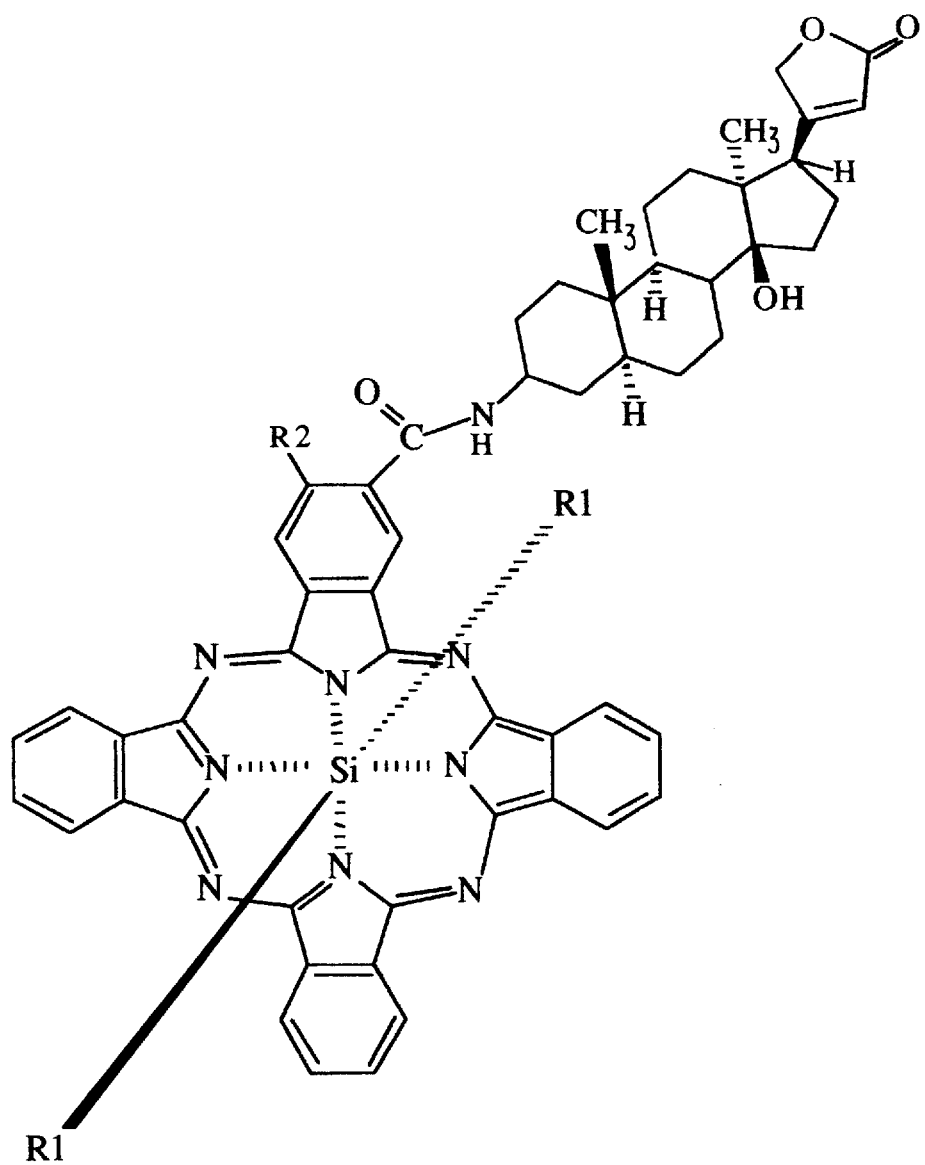
FIG. 27 depicts the structure of caged dicarboxy silicon phthalocyanine digitoxin probe.

The digitoxin probe was purified by procedures similar to those described in Example 3 for the digoxin probe. The structure of the caged dicarboxy silicon phthalocyanine-digitoxin probe is shown in FIG. 27.

EXAMPLE 12

Synthesis of Caged Dicarboxy Silicon Phthalocyanine-Theophylline

A. Preparation of Theophylline 8-Butyric Acid

A mixture of 31.3 g glutaric anhydride, 25 g 5.6-diamino-1,3-dimethyl uracil, and 300 ml N,N-dimethyl-aniline was heated under reflux for 4 hours. Upon cooling, the product crystallized from the dark, clear reaction mixture. The crystals were collected by filtration, washed with benzene, then with methanol, and dried affording 187 g light yellow solid.

B. Preparation of Theophylline-8-(N-2-aminoethyl) butyramide

To a stirred mixture of 453 mg theophylline-8-butyric acid, 6 ml DMF and 4 ml (THF) was added 240 $\mu$l triethylamine. The resultant solution was cooled in ice and 220 $\mu$l isobutylchloroformate was added. After 1 hour the slurry was added to 2 ml ethylenediamine cooled in ice. The reaction mixture was maintained at 0° C. for 6 hours and then concentrated to dryness. The residue, upon fractional crystallization from chloroform+ethanol provided 369 mg pure theophylline-8-(N-2-aminoethyl)butyramide.

C. Preparation of Probe

The theophylline probe was prepared as follows: 1.2 mg theophylline-8-(N-2-aminoethyl)butyramide was placed in a 3.0 ml reaction vial and dissolved in 100 $\mu$l DMF. In a separate vial, caged dicarboxy silicon phthalocyanine (1.0 mg) was dissolved in 400 $\mu$l DMF and then transferred to the reaction vial along with 200 $\mu$l of wash DMF (for a total of 600 $\mu$l DMF). To the reaction vial was added 6.1 mg of HOBT, dissolved and mixed well. To make the final reaction mixture, 7.0 mg EDAC was added and the resulting mixture mixed thoroughly. The reaction mixture was stored overnight at about 4° to 8° C.

D. Purification of Probe

Figure 28:
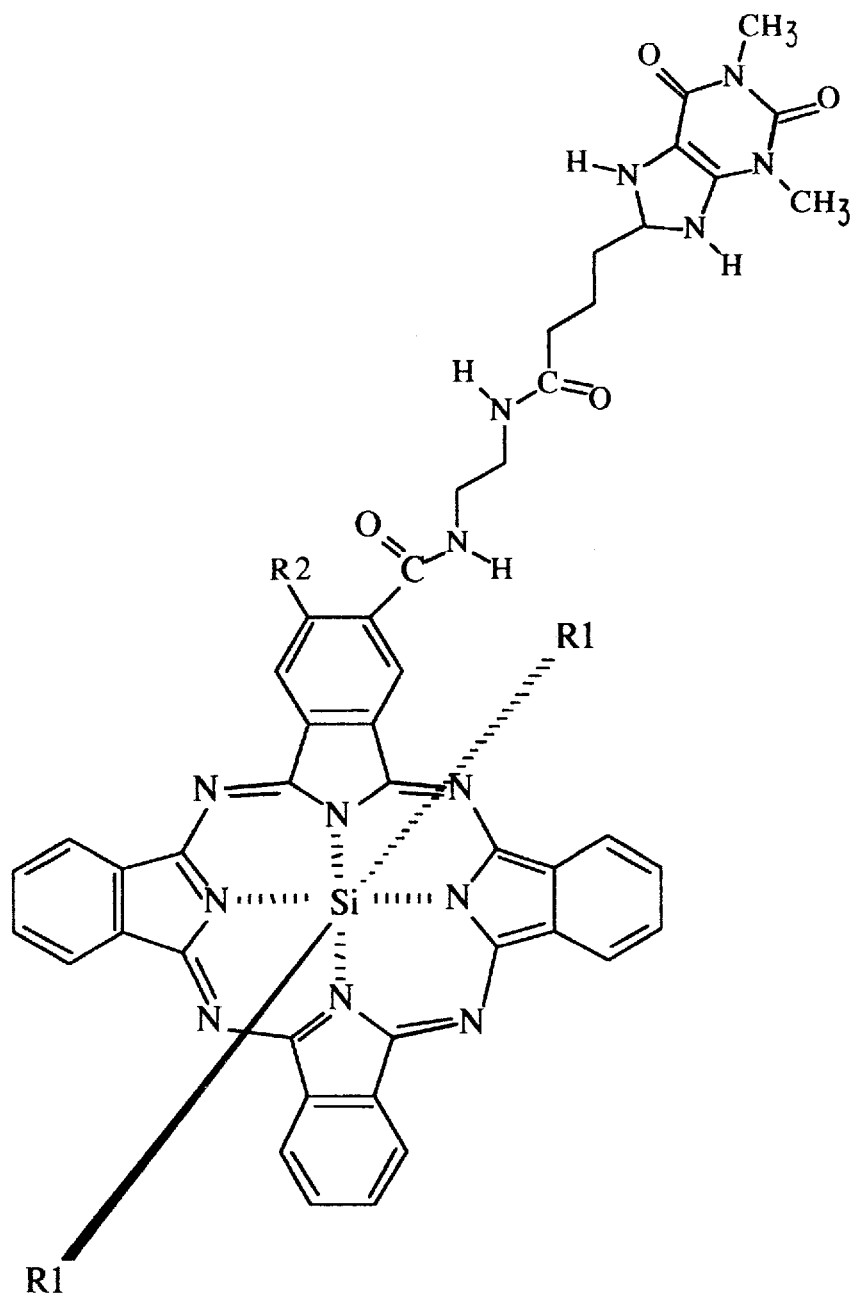
FIG. 28 depicts the structure of caged dicarboxy silicon phthalocyanine theophylline probe.

The theophylline probe was purified using procedures similar to those described in Example 3 for the digoxin probe. The structure of the caged dicarboxy silicon phthalocyanine-digoxigenin probe is shown in FIG. 28.

EXAMPLE 13

Synthesis of Caged Dicarboxy Silicon Phthalocyanine-Phenobarbital

A. Preparation of Nitrophenobarbital

Phenobarbital, 663 mg, was dissolved in 2.7 ml concentrated sulfuric acid cooled in ice. With stirring, a cold solution of 0.16 ml concentrated nitric acid in 0.65 ml concentrated sulfuric acid was added dropwise over a period of 4 minutes. After ½ hour in the cold, the reaction mixture was poured into ice water. The precipitate was collected, washed with water, and dried in vacuo affording 0.03 g white solid.

B. Preparation of Aminophenobarbital

Nitrophenobarbital (225 mg) was stirred in a mixture of 3 ml concentrated HCl, 2 ml acetic acid and 2.5 ml THF. To the slurry mixture was added a solution of 370 mg $SnCl_2$ in 1 ml concentrated HCl and 1 ml acetic acid. After stirring at room temperature for 2 hours, the reaction mixture was concentrated to give an oily residue. To this residue, $NaHCO_3$ solution was added until the pH was about 7. The precipitate was collected, washed with water and dried in vacuo leaving 449 mg white solid. This solid was stirred in 10 ml THF and centrifuged to remove the inorganic material. The supernatant liquid was evaporated and the residue was dried in vacuo affording 138 mg light yellow solid.

C. Preparation of Probe

The phenobarbital probe was prepared as follows: 1.2 mg of 5-ethyl-5-(aminophenyl)barbituric acid (P-aminophenobarbital) was placed in a 3.0 ml reaction vial and dissolved with 200 $\mu$l DMF. In a separate vial the caged dicarboxy silicon phthalocyanine (1.0 mg) was dissolved in 200 $\mu$l DMF and then transferred to the reaction vial. To the reaction vial was added 2.4 mg HOBT, dissolved and mixed well. To make the final reaction mixture, 2.8 mg of EDAC was added and mixed thoroughly. The reaction mixture was stored overnight at about 4° to 8° C.

D. Purification of Probe

Figure 29:
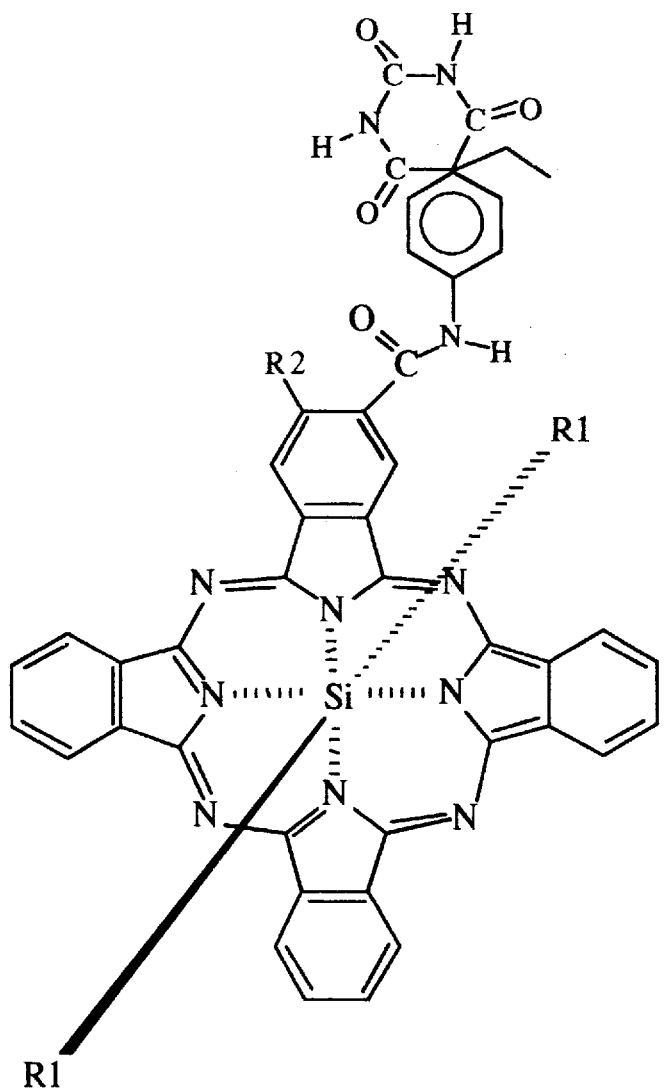
FIG. 29 depicts the structure of caged dicarboxy silicon phthalocyanine phenobarbital probe.

The phenobarbital probe was purified using procedures similar to those described in Example 3 for the digoxin probe. The structure of the caged dicarboxy silicon phthalocyanine probe is shown in FIG. 29.

EXAMPLE 14

Synthesis of Caged Dicarboxy Silicon Phthalocyanine-Thyroxine

A. Preparation of Thyroacetic Acid Ethylenediamine

To a stirred mixture of 100 mg thyroacetic acid in 15 ml pyridine was added 16 mg of N-hydroxysuccinimide and 27.6 mg N,N'-dicyclohexylcarbodiimide. The mixture was stirred for 2 hours at room temperature and transferred to 4° C. for 18 hours. The crystals were removed by filtration and 8.03 mg of ethylenediamine was added to the filtrate with stirring. This reaction was allowed to proceed an additional 24 hours at 4° C. and was dried in vacuo resulting in whitish-gray powder. The material was stored at −20° C. in a desiccator.

B. Preparation of Probe

The thyroxine probe was prepared as follows: 1.0 mg of tetraiodothyroacetic acid-ethylenediamine (Tetrac-EDA) was placed in a 3.0 ml reaction vial and dissolved in 100 µl DMF. In a separate vial, caged dicarboxy silicon phthalocyanine (1.0 mg) was dissolved in 400 µl DMF and then transferred to the reaction vial along with 200 µl of wash DMF for a total of 600 µl. To the reaction vial was added 1.8 mg HOBT, dissolved and mixed well. To the final reaction mixture, 1.5 mg EDAC was added and the resulting mixture mixed thoroughly. The reaction mixture was stored overnight at about 4° to 8° C.

C. Purification of Probe

Figure 30:
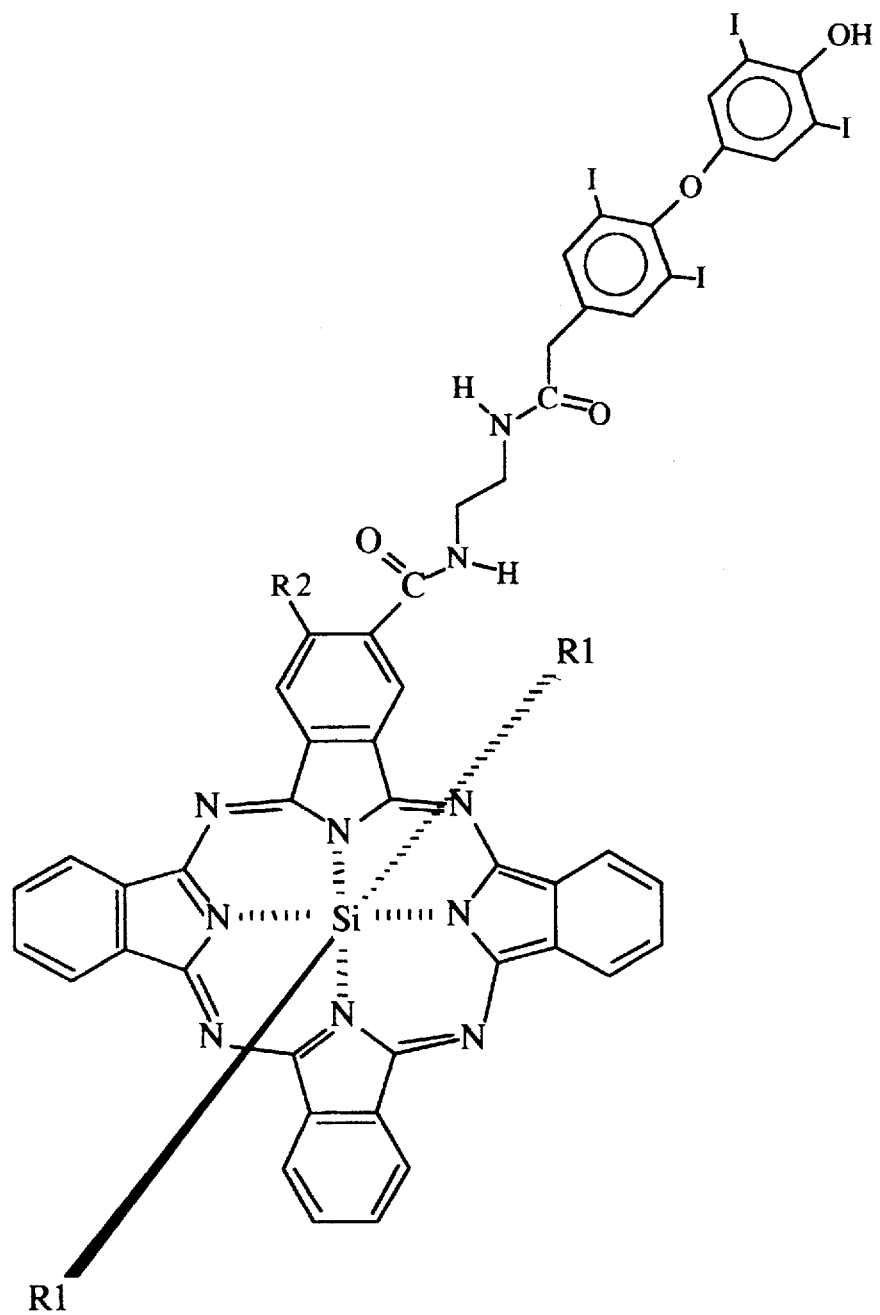
FIG. 30 depicts the structure of caged dicarboxy silicon phthalocyanine thyroxine probe.

The thyroxine probe was purified using procedures similar to those described in Example 3 for the digoxin probe. The structure of the caged dicarboxy silicon phthalocyanine-thyroxine probe is shown FIG. 30.

EXAMPLE 15

Synthesis of Caged Dicarboxy Silicon Phthalocyanine-N-Acetylprocainamide

A. Preparation of Desethyl-N-Acetylprocainamide

Desethyl-N-acetylprocainamide was prepared by dissolving 1.0 g of p-acetamidobenzoic acid and 0.7 g N-hydroxysuccinimide in 20 ml pyridine. To this solution was added 1.4 g of N,N'-dicyclohexylcarbodiimide. The reaction mixture was placed at 4° C. for 18 hours, at which time the crystals were removed by filtration. The filtration was brought to room temperature and with stirring, 0.51 g N-ethylethylenediamine ethylethylenediamine was added. Stirring continued for 3 hours, the solution was cooled to 4° C. and allowed to react for an addition 24 hours at 4° C. The second crop of crystals was removed by filtration, dissolved in 25 ml of distilled water. The pH was adjusted to 10 with sodium hydroxide to form a white precipitate of desethyl-N-acetylprocainamide. The resultant precipitate was dried in vacuo and stored at −20° C. in a desiccator.

B. Preparation of Probe

The N-Acetylprocainamide probe was prepared as follows: 1.0 mg desethyl-N-Acetylprocainamide was placed in a 3.0 ml reaction vial and dissolved with 100 µl DMF. In a separate vial, caged dicarboxy silicon phthalocyanine (1.0 mg) was dissolved in 400 µl DMF and then transferred to the reaction vial along with 200 µl of wash DMF for a total of 600 µl. To the reaction vial was added 4.2 mg HOBT, dissolved and mixed well. To make the final reaction mixture, 10.5 mg EDAC was added and mixed thoroughly. The reaction mixture was stirred overnight at about 4° to 8° C.

C. Purification of Probe

Figure 31:
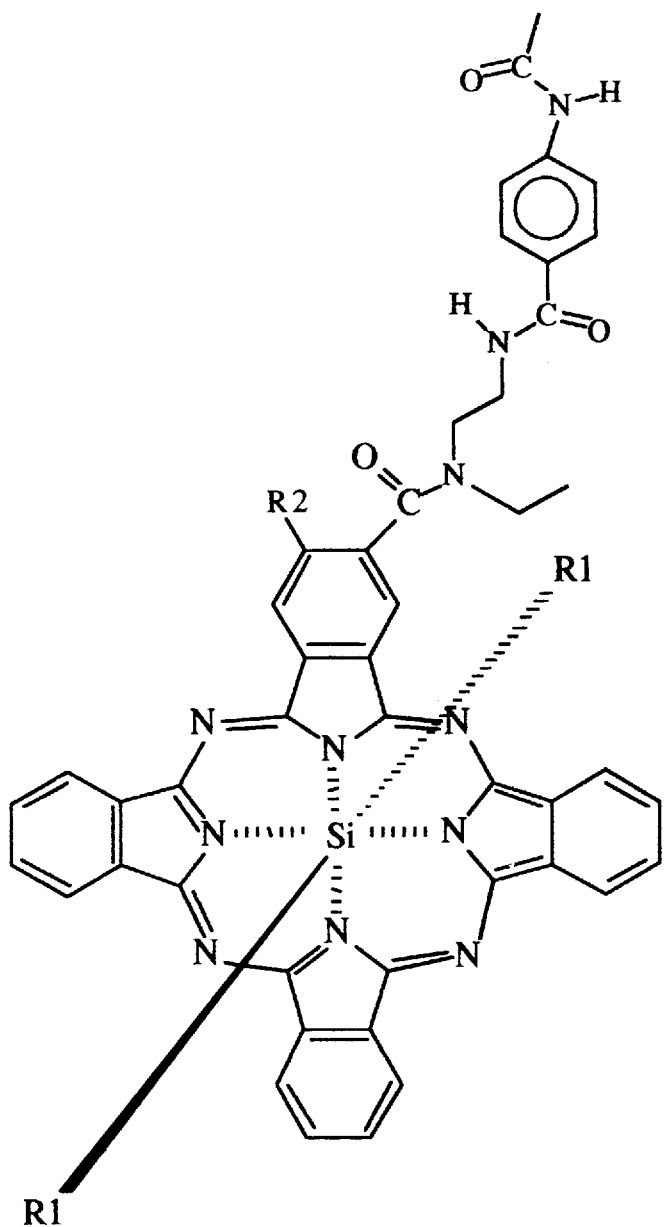
FIG. 31 depicts the structure of caged dicarboxy silicon phthalocyanine n-acetylprocainamide probe.
Figure 32:
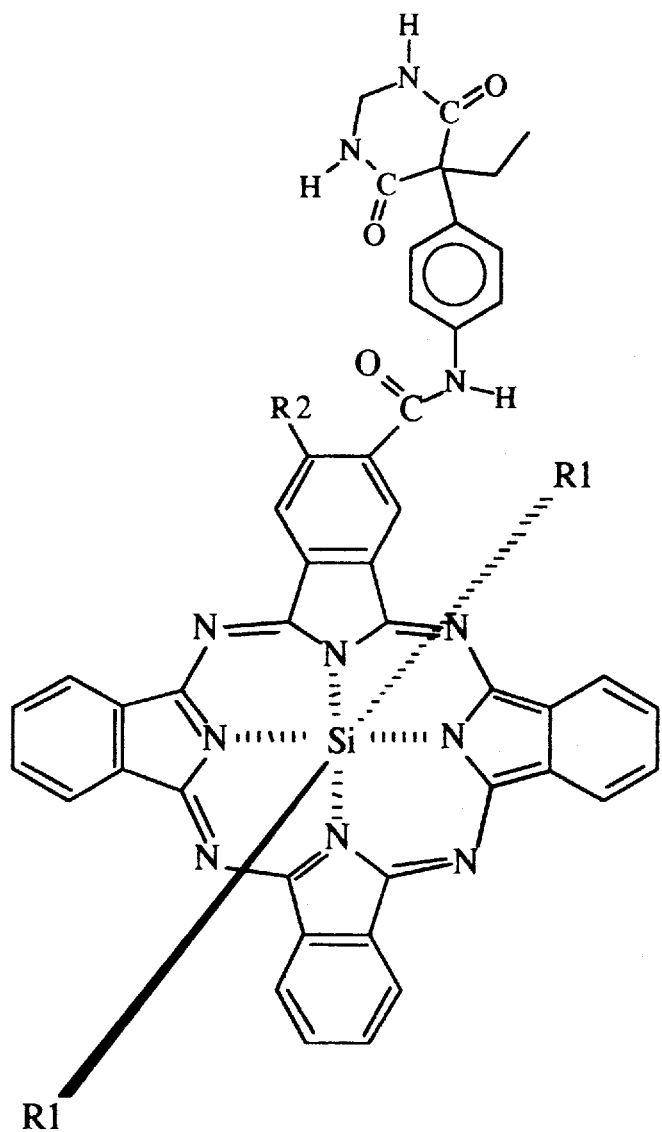
FIG. 32 depicts the structure of caged dicarboxy silicon phthalocyanine primidone probe.

The N-Acetylprocainamide probe was purified using procedures similar to those described in Example 4 for the digoxin probe. The structure of the caged dicarboxy silicon phthalocyanine-N-acetylprocainamide probe is shown in FIG. 31.

EXAMPLE 16

Synthesis of Caged Dicarboxy Silicon Phthalocyanine-Primidone

A. Preparation of Nitroprimidone

Primidone, 1.60 g, was dissolved with stirring in 8 ml concentrated sulfuric acid and cooled in ice. A cold solution of 485 µl concentrated nitric acid in 2 ml concentrated sulfuric acid was added over a period of 10 minutes. After 2 hours at 0° C. the reaction mixture was poured into ice water neutralized with cold sodium hydroxide. The precipitate was collected, washed with water and dried in vacuo affording 1.79 g white solid.

B. Preparation of Aminoprimidone

Nitroprimidone 1.79 g was dissolved with heating in 15 ml concentrated, HCl and 35 ml THF. The solution was allowed to cool to room temperature. A solution of 4.86 SnCl$_2$ in 3 ml concentrated HCl and 3 ml THF was added over a period of 10 minutes. After stirring at room temperature overnight, the reaction mixture was made basic with ammonium hydroxide. The THF layer was separated and evaporated to dryness. The residue was dried in vacuo, stirred in 10 ml THF and centrifuged to remove inorganic material. The clean THF solution was evaporated in vacuo to provide a residue which upon fractional crystallization from THF and petroleum either yielded 519 mg pure aminoprimidone.

C. Preparation of Probe

The primidone probe was prepared as follows: 0.8 mg 5-ethyl-5-(4-aminophenyl)hexahydropyrimidine-4,6-dione (p-aminoprimidone) was placed in 100 µl DMF in a 3.0 µl reaction vial. To the reaction vial was added 1.0 mg caged dicarboxy silicon phthalocyanine (1.0 mg) and 3.1 mg HOBT. To make the final reaction mixture, 3.9 mg EDAC was added along with 150 ml DMF and the resulting mixture mixed thoroughly. The reaction mixture was stored overnight at about 4°–80° C.

D. Purification of Probe

The primidone probe was purified using procedures similar to those described in Example 3 for the digoxin probe. The structure of the caged dicarboxy silicon phthalocyanine-primidone probe is shown in FIG. 37.

EXAMPLE 17

Synthesis of Caged Dicarboxy Silicon Phthalocyanine-Phenytoin

A. Preparation of Probe

The phenytoin probe was prepared as follows: 1.2 mg of diphenylglycine was placed in a 3.0 ml reaction vial and dissolved with 100 µl DMF. In a separate vial, dicarboxyphthalocyanine (3.0 mg) was dissolved in 400 ml DMF and then transferred to the reaction vial along with 200 µl of wash DMF for a total of 600 µl. To the reaction vial was added 6.1 mg of HOBT, dissolved and mixed well. To make the final reaction mixture, 7.0 mg of EDAC was added and mixed thoroughly. The reaction was stored at 4.0°–8.0° C. overnight.

B. Purification of Probe

Figure 33:
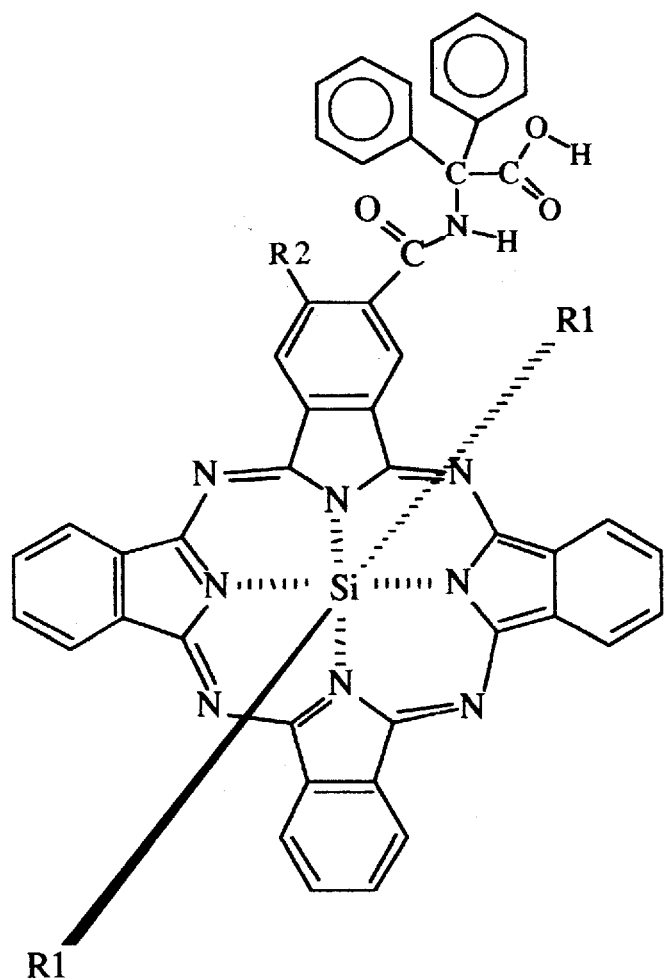
FIG. 33 depicts the structure of caged dicarboxy silicon phthalocyanine phenytoin probe.

The phenytoin-phthalocyanine probe was purified using procedures similar to those described in Example 3 for the digoxin probe. The structure of the caged dicarboxy silicon phthalocyanine-phenytoin probe is shown in FIG. 33.

EXAMPLE 18

Rubella Anti-IgG Probe

A. Labeling of Goat Anti-Human IgG

Caged dicarboxy silicon phthalocyanine dye (12 μ moles) prepared according to Example 1 and purified by DEAE Sephadex chromatography was mixed with 1 ml of pyridine-pyridinium chloride buffer made by mixing 5 ml 1M HCl with 0.5 ml pyridine. The solution was taken to dryness in a sublimation apparatus and the excess pyridine and pyridinium chloride was removed, thus assuring that all acetate ion present would be removed. The dry residual dye was dissolved in anhydrous dichloromethane to make a 3.5 mM solution.

The carboxylic acid groups of the dye were converted to the imidazolide by mixing 1 ml of 3.5 mM dye with 760 μl of 0.46M carbonyl diimidazole and allowing 1.5 hour at room temperature for reaction, after which the solvent was removed in vacuo.

DMF was scavenged free of water and reactive amines by adding carbonyl diimidazole to a final concentration of 0.1M.

To 100 μl of scavenged DMF was added 10 μl of $H_2O$ and 100 μl of this mixture was added in the cold to the dry activated dye. After 1 minute this mixture was added to a mixture of 600 μl IgG solution containing 6 mg of goat anti-human IgG and 100 μl of 100 mM phosphate, pH 7.6. The reaction was allowed to proceed for 4.5 hours at room temperature and overnight at 4° C. A portion of the reaction mixture was equilibrated with 10 mM phosphate, pH 7.6 by two treatments in a Minicon concentrator (Amicon Corporation, Danvers, Ma., USA) and passed through a hydroxylapatite column (Bio Rad Laboratories, Richmond, Calif., USA) equilibrated with 10 mM phosphate, pH 7.6. Free dye eluted at this stage and the labeled antibody was recovered by elution with 100 mM phosphate, pH 7.6.

B. Analysis of Probe

The labeled antibody was found by absorbance measurements at 280 nm and 682 nm to contain an average of 1.3 moles of dye/mole of IgG. It was shown to react specifically in a solid phase sandwich assay in which adsorbed rubella virus antigen was coated with human anti-rubella which enabled reaction with the labeled antibody. Transient-state fluorescence intensity measurements in the 680 nm region were used to quantify the bound labeled antibody. Specificity was further tested by correlation with a standard method. A series of 40 patient samples were run; 4 were negative by both methods, 35 were positive by both while one was positive by the standard method and negative transient state fluorescence.

Figure 34:
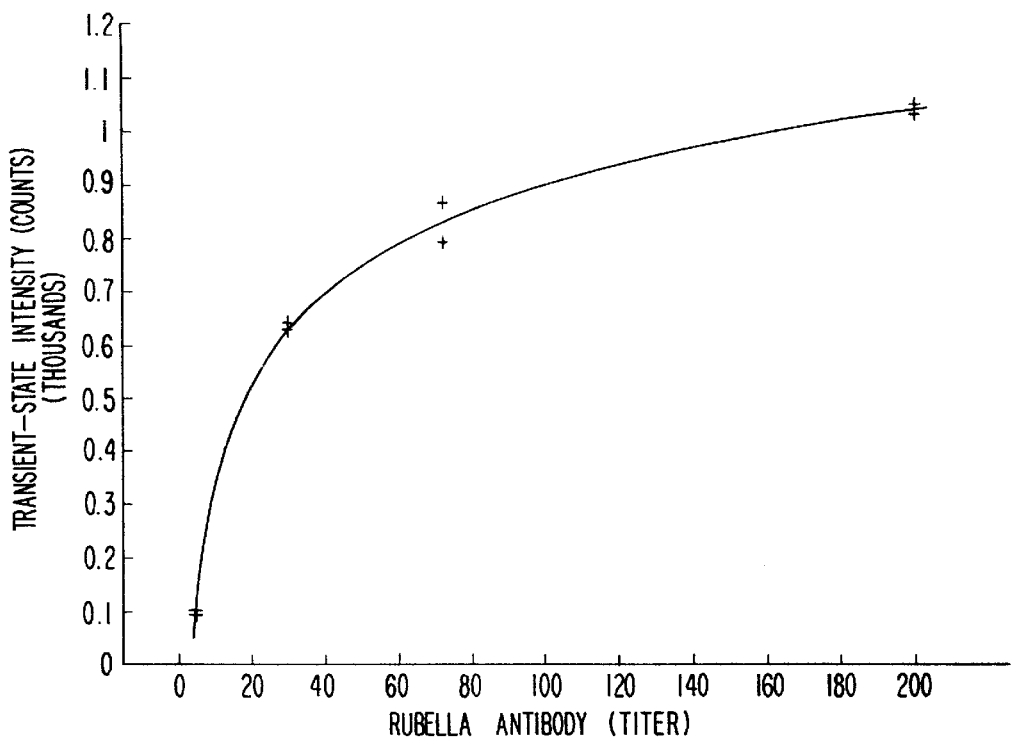
FIG. 34 depicts a rubella antibody calibration curve for a sandwich assay.

In clinical pathology and medical screening, specificity is defined as the proportion of individuals with negative test results for the disease that the test is intended to reveal, i.e., true negative results as a proportion of the total number of true negative and false positive results. In this example, by this definition, this assay demonstrated 100% specificity. In addition, sensitivity of a procedure can be defined as that proportion of individuals with a positive test result for the disease that the test intended to reveal, i.e., true positive results as a proportion of the total true positive and false negative results. These data indicate a 97.2% sensitivity for this assay system. Although we report a relatively small number of samples the performance of the assay demonstrates the use of an antibody labeled with the marker components in a sandwich assay. See FIG. 34.

EXAMPLE 19

Synthesis of Caged Dicarboxy Silicon Phthalocyanine Synthetic Rubella Peptide

A. Preparation of Probe

A synthetic rubella peptide, for example, a portion of the $E_1$ protein of the rubella virus (Therien strain), can be synthesized by standard peptide synthesis procedure. The coupling of caged dicarboxy silicon phthalocyanine (prepared according to Example 1) to the synthetic rubella peptide was a four step process:

1. Dye activation—Sufficient caged dicarboxy silicon phthalocyanine in dimethylformamide to give a molar ratio of caged dicarboxy silicon phthalocyanine dye to peptide of 1.3 was activated by adding 50 moles of carbonyldiimidazole per mole of dye in dichloromethane to form an imidazole.
2. Decomposition of excess carbonyldiimidazole—The dichloromethane was evaporated from the activation mixture and water was added to decompose the excess carbonyldiimidazole.
3. Coupling to Peptide—The solution was buffered by adding for each μ mole of carbonyldiimidazole used 1 μl of a mixture of 100 μl of pyridine, 2.38 ml water and 620 μl of 1M HCl. The resulting solution was added to the dry peptide. Alternatively, the carbonyldiimidazolide was reacted with the peptide in DMF.

B. Purification of Probe

Purificaiton of caged dicarboxy silicon phthalocyanine labelled peptide from the reaction mixture was carried out by high performance liquid chromatography on a reversed phase $C_{18}$ column using a water-methanol gradient.

EXAMPLE 20

Immunological Evaluation of Phthalocyanine-Rubella Probe

Two assay procedures were performed in order to evaluate the phthalocyanine-Rubella probe. The phthalocyanine-Rubella Probe was diluted in a 0.01 Tris buffer pH 8.0 containing 0.1% bovine serum and 0.025% Tween 20. The probe concentration was determined to be $1.1 \times 10^{-11}$M/L. Rubella peptide calibrators were made by diluting in the Tris buffer to the following concentrations: 0.0, $1.0 > 10^{-12}$, $2.7 \times 10^{-12}$, and $5.4 \times 10^{-12}$, $2.7 \times 10^{-11}$, and $5.4 \times 10^{-11}$. The antibody was made by hyper-immunizing a rabbit with the Rubella peptide. Dilutions were made in the Tris buffer described above.

A. Competitive Binding Assay (Sequential Format)

To a series of small conical test tubes was added 25 μl Tris buffer, 20 μl antibody solution and 10 μl antibody solution and 10 μl of each peptide calibrator. The tubes were incubated at 35° C. for 10 minutes. At this time, 15 μl of probe was added to each tube and incubated an additional 20 minutes at 35° C. After incubation 1.0 ml of Tris buffer was added and transient state polarization measurements were made.

Figure 35:
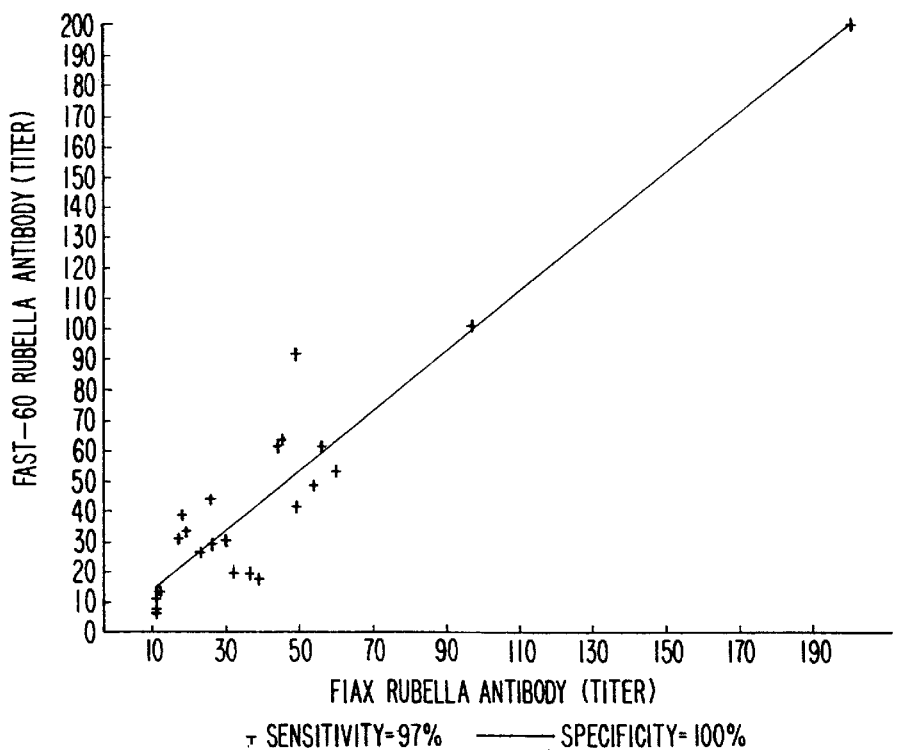
FIG. 35 depicts a rubella peptide calibration curve for an inhibition assay.

The typical inhibition curve is shown in FIG. 35. The data obtained clearly demonstrated a sensitivity of $1.0 \times 10^{-12}$M/L of peptide in a homogeneous fluorescence polarization assay.

B. Antibody Titration Curve

Figure 36:
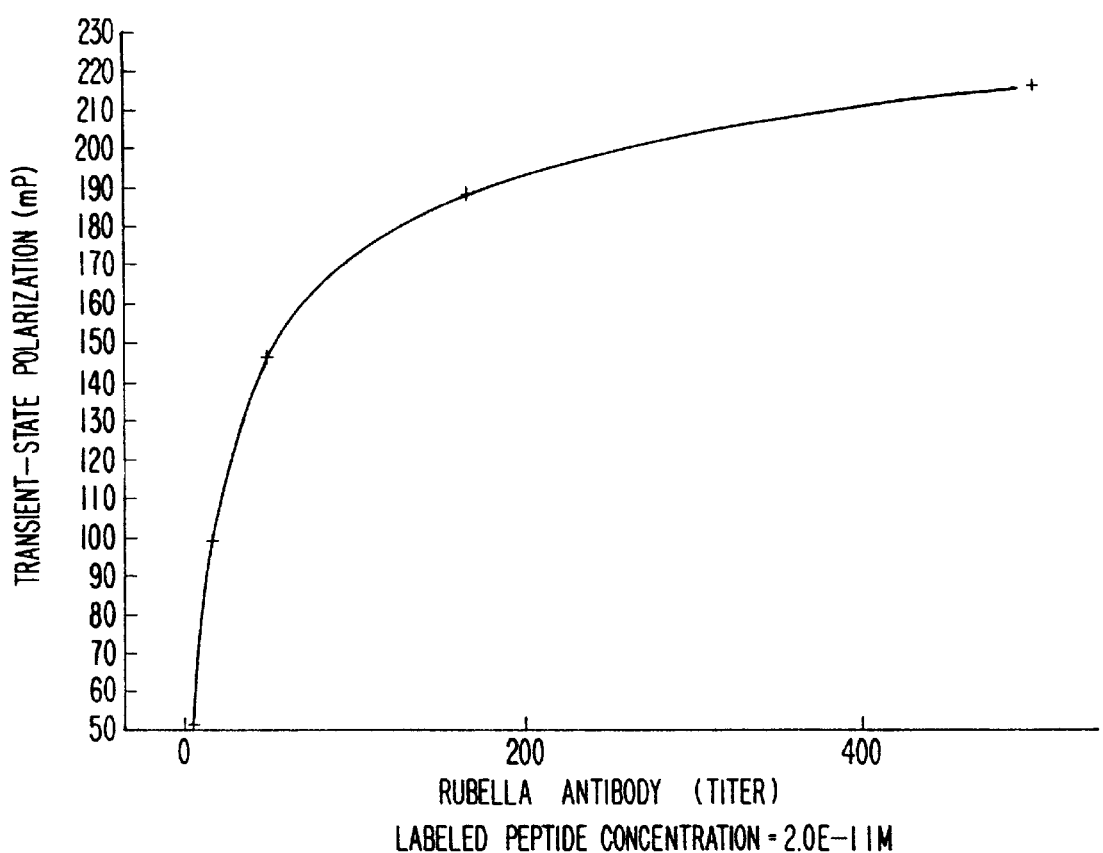
FIG. 36 depicts a rubella antibody calibration curve for direct polarization.

To a series of small conical test tubes, varying dilutions of rubella antibody (20 μl) was incubated with 20 μl Tris buffer and 15 μl probe for 20 minutes at 35° C. After incubation 1.0 ml of Tris buffer was added to each tube and the transient state polarization was measured. The data obtained are shown in FIG. 36.

A typical antibody was obtained at a probe concentration of $2.0 \times 10^{-11}$ M/L. As can be seen from the data, the probe when depolarized in buffer has a polarization of 51 millipolarization units (mP) and when bound to antibody exhibits a polarization of 215 mP, with a dynamic range of 164 mP. Thus, indicating the ability to use a homogeneous polarization assay for detection of rubella virus antibodies in human serum samples.

Those skilled in the art will recognize that the methods used in the above examples relating to rubella peptide are applicable to other peptides. For example, probes can be made for peptide hormones such as luteinizing hormone, follicular stimulating hormone, human choriogonadotropin, thyroid stimulating hormone. Angiotensin I, Angiotensin II, prolactin and insulin. Probes can be made for peptides such as tumor markers (for example, carcinoembryonic antigen) as well.

To assist in understanding the invention, the results of a series of experiments have been provided. The above examples relating to the present invention should not, of course, be construed as limiting the scope of the invention. Such variations of the invention, now known or later developed, which would fall within the purview of those skilled in the art are to be considered as falling within the scope of the invention as hereinafter claimed.

We claim:

1. A method for determining the presence or amount of a target analyte in a sample comprising the steps:
   (a) contacting a sample suspected of containing a target analyte with a known quantity of added target analyte or analog thereof linked to a fluorescent probe wherein said fluorescent probe comprises a detectably labeled marker component, wherein said detectably labeled marker component comprises a fluorescent porphyrin or azaporphyrin that is both: (i) coordinated to a central metal atom and (ii) coupled to two solubilizing polyoxyhydrocarbyl moieties, one located on either side of the planar molecular structure;
   (b) contacting said sample with a receptor capable of specifically recognizing said target analyte;
   (c) determining the amount of fluorescent probe linked to added target analyte bound to said receptor or the amount of fluorescent probe linked to added target analyte which is not bound to said receptor; and
   (d) comparing said amount of bound or unbound fluorescent probe with the amount of fluorescent probe in a standard sample free of said target analyte or containing said target analyte in a known amount.

2. The method of claim 1 further comprising diluting the resultant mixture from step (b) by an amount of from 2-fold to 100-fold.

3. The method of claim 2 wherein said diluting is by an amount of from about 7-fold to about 50-fold.

4. The method of claim 3 wherein said diluting is by an amount of from about 35-fold.

5. A method for determining the presence or amount of a target analyte in a sample comprising the steps:
   (a) contacting a sample suspected of containing a target analyte with a first receptor capable of specifically recognizing said target analyte to form a complex of said target analyte and said first receptor, said first receptor being labeled with a fluorescent probe which comprises a fluorescent porphyrin or azaporphyrin that is both: (i) coordinated to a central metal atom and (ii) coupled to two solubilizing polyoxyhydrocarbyl moieties, one located on either side of the planar molecular structure;
   (b) contacting the complex with a second receptor capable of specifically recognizing said target analyte, said second receptor being bound to a solid carrier, to form a complex of said first labeled receptor, said target analyte and said second receptor bound to said solid carrier;
   (c) measuring either the amount of labeled first receptor associated with said solid carrier or the amount of unreacted labeled first receptor; and
   (d) relating the amount of labeled first receptor measured to the amount of labeled first receptor measured for a control sample free of said target analyte, or relating the amount of labeled first receptor measured with the amount of labeled first receptor measured in samples containing known amounts of target analyte.

6. The method of claim 5 further comprising the step of separating said solid carrier from said sample and said unreacted labeled first receptor.

7. A method for determining the presence or amount of a target analyte in a sample comprising the steps of:
   (a) simultaneously contacting a sample suspected of containing a target analyte with first and second receptors capable of specifically recognizing said target analyte, said first receptor being labeled with a fluorescent probe which comprises a fluorescent porphyrin or azaporphyrin that is both: (i) coordinated to a central metal atom and (ii) coupled to two solubilizing polyoxyhydrocarbyl moieties, one located on either side of the planar molecular structure and said second receptor being bound to a solid carrier, to form a complex of said first receptor, said target analyte, and said second receptor;
   (b) measuring either the amount of labeled first receptor associated with said solid carrier or the amount of unreacted labeled first receptor; and
   (c) relating the amount of labeled first receptor measured to the amount of labeled first receptor measured for a control sample free of said target analyte, or relating the amount of labeled first receptor measured with the amount of labeled first receptor measured in samples containing known amounts of target analyte.

8. The method of claim 7 further comprising the step of separating said solid carrier from said sample and said unreacted labeled first receptor.

9. The method of claim 5 or 7 wherein said first receptor is labeled with a first fluorescent probe and said second receptor is labeled with a second fluorescent probe, the first fluorescent probe having a different absorption and emission than the second fluorescent probe, and wherein the absorption of one of the fluorescent probes overlaps with the emission of the other fluorescent probe.

10. The method of claim 1, 5 or 7 wherein said sample is a biological fluid.

11. The method of claim 10 wherein said biological fluid is plasma.

12. The method of claim 10 wherein said biological fluid is whole blood.

13. The method of claim 12 wherein red blood cells in said whole blood have been lysed.

14. The method of claim 13 wherein said red blood cells have been caused to lyse by use of a compound selected from the group consisting of stearyl-lysolecithin, palmitoyl-lysolecithin and myristoyl-lysolecithin.

15. The method of claim 10 wherein said biological fluid is urine.

16. The method of claim 1, 5, or 7 wherein said target analyte is selected from the group consisting of an antigen, a hapten, and an antibody, and said receptor is selected from the group consisting of an antigen and an antibody.

17. The method of claim 16 wherein said antibody is a monoclonal antibody.

18. The method of claim 1, 5 or 7 wherein said target analyte is a drug or a metabolite of a drug.

19. The method of claim 18 wherein said drug is a steroid, hormone, antiasthmatic, antineoplastic, antiarrhythmic, anticonvulsant, antiarthritic, antidepressant, or cardiac glycoside.

20. The method of claim 18 wherein said drug is digoxin.

21. The method of claim 18 wherein said drug is N-acetylprocainamide.

22. The method of claim 18 wherein said drug is phenobarbital.

23. The method of claim 18 wherein said drug is primidone.

24. The method of claim 18 wherein said drug is theophylline.

25. The method of claim 18 wherein said drug is thyroxine.

26. The method of claim 18 wherein said drug is digitoxin.

27. The method of claim 1, 5 or 7 wherein said target analyte is a peptide.

28. The method of claim 27 wherein said peptide is rubella virus peptide.

29. The method of claim 27 wherein said peptide is a portion of the $E_1$ viral protein of rubella virus peptide.

30. The method of claim 1, 5 or 7 wherein said method is capable of detecting target analyte in a concentration of from about $1 \times 10^{-5}$ M/L to about $1 \times 10^{-13}$ M/L.

31. The method of claim 1, 5 or 7 wherein said method is capable of detecting target analyte in a concentration of from about $1 \times 10^{-10}$ M/L to about $1 \times 10^{-12}$ M/L.

32. The method of claim 18 wherein said method is capable of detecting drug or metabolite in a concentration of from about $5 \times 10^{-9}$ M/L to about $5 \times 10^{-12}$ M/L.

33. The method of claim 32 wherein said method is capable of detecting drug or metabolite in a concentration of from about $1 \times 10^{-10}$ M/L to about $5 \times 10^{-10}$ M/L.

34. The method of claim 32 wherein said drug is digoxin.

35. The method of claim 33 wherein said drug is digoxin.

36. The method of claim 27 wherein said method is capable of detecting peptide at a concentration of from about $1 \times 10^{-10}$ M/L to about $1 \times 10^{-12}$ M/L.

37. The method of claim 36 wherein said peptide is rubella virus peptide or a portion thereof.

38. The method of claim 1, 5 or 7 wherein said determining of amount of fluorescent probe is by steady-state fluorescence measurement.

39. The method of claim 1, 5 or 7 wherein said determining of amount of fluorescent probe is by transient state fluorescence measurement.

40. The method of claim 1, 5 or 7 wherein said determining of the amount of fluorescent probe is made by measurement of light at a wavelength of greater than 500 nm.

41. The method of claim 40 wherein said determining of the amount of the fluorescent probe is made by measurement of light at a wavelength of greater than 650 nm.

42. The method of claim 40 wherein said determining of the amount of the fluorescent probe is made by measurement of light at a wavelength of 680 nm.

43. The method of claim 40 wherein said determining of the amount of the fluorescent probe is made by measurement of light at a wavelength of 690 nm.

44. The method of claim 40 wherein said determining of the amount of the fluorescent probe is made by measurement of light at a wavelength of greater than about 700 nm.

45. The method of claim 1, 5 or 7 wherein said luminescent substantially planar molecular structure comprises a macrocyclic multidentate ligand coordinated to a central atom.

46. The method of claim 1, 5 or 7 wherein one of said two solubilizing polyoxyhydrocarbyl moieties is linked on either side of the plane of the macrocyclic ligand to the central atom.

47. The method of claim 1, 5 or 7 wherein said two solubilizing polyoxyhydrocarbyl moieties comprise axial ligands which coordinate to the central atom.

48. The method of claim 47 wherein said solubilizing polyoxyhydrocarbyl moieties are selected from the group consisting of polyethers, polyols, water soluble carbohydrates, and water soluble carbohydrate derivatives.

49. The method of claim 47 wherein said central atom is capable of forming octahedral coordination complexes.

50. The method of claim 45 wherein said macrocyclic multidentate ligand has a conjugated $\pi$-electron system.

51. The method of claim 50 wherein said macrocyclic multidentate ligand comprises a nitrogen-containing macrocycle.

52. The method of claim 51 wherein said macrocyclic multidentate ligand is selected from the group consisting of a fluorescent porphyrin derivative, a fluorescent porphyrin derivative having one or more bridging carbons replaced by nitrogen, a fluorescent corrin derivative, a fluorescent saphyrin derivative, and a fluorescent porphycene derivative.

53. The method of claim 52 wherein said central atom is selected from the group consisting of silicon, germanium, phosphorus and tin.

54. The method of claim 51 wherein said macrocycle comprises a fluorescent porphyrin derivative wherein from 1 to 4 of the bridging carbon atoms is replaced by nitrogen.

55. The method of claim 48 wherein said solubilizing polyoxyhydrocarbyl moieties comprise polyethylene glycol or water soluble polyethylene glycol derivatives thereof.

56. The method of claim 55 wherein each said polyoxyhydrocarbyl moieties has a molecular weight of about 200 to about 20,000.

57. The method of claim 54 wherein said macrocycle comprises a fluorescent tetrabenzotriazaporphyrin derivative.

58. The method of claim 57 wherein said macrocycle is selected from the group consisting of tetrabenzotriazaporphyrin, 27-phenyltetrabenzotriazaporphyrin, and 27-(p-methylphenyl)tetrabenzotriazaporphyrin.

59. The method of claim 53 wherein the central atom is silicon.

60. The method of claim 54 wherein said macrocyclic ligand has a low degree of symmetry so as to enhance the polarization of emission parallel to polarization of absorption.

61. The method of claim 60 wherein said central atom is silicon or germanium.

62. The method of claim 61 wherein said macrocyclic ligand has a lower symmetry than $D_{4h}$.

63. The method of claim 62 wherein said macrocyclic ligand has at least one fused aromatic ring.

64. The method of claim 62 wherein said macrocyclic ligand comprises a fluorescent porphyrin derivative wherein 1 to 3 of the bridging carbon atoms is replaced by nitrogen.

65. The method of claim 63 wherein said macrocyclic ligand comprises a fluorescent phthalocyanine derivative.

66. The method of claim 63 wherein said macrocycle comprises a fluorescent tetrabenzotriazaporphyrin derivative.

67. The method of claim 1, 5 or 7 wherein said detectably labelled marker component comprises a fluorophore moiety coupled to two solubilizing polyoxyhydrocarbyl moieties which in the presence of serum components in aqueous solution is characterized by transient state fluorescence emission having parallel and perpendicular components of substantially the same intensities as without serum.

68. The method of claim 67 wherein said fluorophore moiety comprises a fluorescent tetrabenzotriazaporphyrin derivative.

69. The method of claim 67 wherein said fluorophore moiety comprises a fluorescent phthalocyanine derivative.

70. The method of claim 1, 5 or 7 wherein said fluorescent probe has a decay time in the range of from about 1 nanosecond to about 50 nanoseconds.

71. The method of claim 70 wherein said decay time is in the range of from about 5 nanoseconds to about 20 nanoseconds.

72. A method for determining the presence or amount of a target analyte in serum comprising the steps:

(a) contacting serum suspected of containing target analyte with a known quantity of added target analyte of analog thereof linked to a fluorescent probe wherein said fluorescent prove comprises a detectable labeled marker component, wherein said detectable labeled marker component comprises a fluorescent porphyrin or azaporphyrin that is both: (i) coordinated to a central metal atom and (ii) coupled to two solubilizing polyoxyhydrocarbyl moieties, one located on either side of the planar molecular structure;

(b) contacting said serum with a receptor capable of specifically recognizing said target analyte;

(c) determining the amount of fluorescent probe linked to added target analyte bound to said receptor or the amount of fluorescent probe linked to added target analyte which is not bound to said receptor; and (d) comparing said amount of bound or unbound fluorescent probe with the amount of fluorescent probe in a standard serum sample free of said target analyte or containing said target analyte in a known amount.

* * * * *